US00RE46170E

(19) United States
(12) Reissued Patent
Kodra et al.

(10) Patent Number: US RE46,170 E
(45) Date of Reissued Patent: Oct. 4, 2016

(54) INSULIN DERIVATIVES

(71) Applicant: Novo Nordisk A/S, Bagsvaerd (DK)

(72) Inventors: Janos Tibor Kodra, Koebenhavn Oe (DK); Patrick William Garibay, Holte (DK); Thomas Hoeg-Jensen, Klampenborg (DK); Ib Jonassen, Valby (DK); Peter Madsen, Bagsvaerd (DK); Tina Moeller Tagmose, Ballerup (DK)

(73) Assignee: Novo Nordisk A/S, Bagsvaerd (DK)

(21) Appl. No.: 14/315,955

(22) Filed: Jun. 26, 2014

Related U.S. Patent Documents

Reissue of:

(64) Patent No.: 8,476,228
Issued: Jul. 2, 2013
Appl. No.: 13/273,659
Filed: Oct. 14, 2011

U.S. Applications:

(63) Continuation of application No. 11/814,019, filed as application No. PCT/EP2006/050593 on Feb. 1, 2006, now Pat. No. 8,067,362.

(60) Provisional application No. 60/651,035, filed on Feb. 8, 2005.

(30) Foreign Application Priority Data

Feb. 2, 2005 (DK) ..... PA 2005 00157

(51) Int. Cl.
*A61K 38/28* (2006.01)
*C07K 14/62* (2006.01)

(52) U.S. Cl.
CPC ..... *A61K 38/28* (2013.01); *C07K 14/62* (2013.01)

(58) Field of Classification Search
None
See application file for complete search history.

(56) References Cited

U.S. PATENT DOCUMENTS

| | | | | |
|---|---|---|---|---|
| 3,528,960 | A | 9/1970 | Haas et al. | |
| 4,179,337 | A | 12/1979 | Davis et al. | |
| 5,750,497 | A | 5/1998 | Havelund et al. | |
| 5,898,067 | A | 4/1999 | Balschmidt et al. | |
| 5,905,140 | A | 5/1999 | Hansen | |
| 6,011,007 | A | 1/2000 | Havelund et al. | |
| 6,174,856 | B1 | 1/2001 | Langballe et al. | |
| 6,251,856 | B1 | 6/2001 | Markussen et al. | |
| 6,869,930 | B1 | 3/2005 | Havelund et al. | |
| 7,615,532 | B2 | 11/2009 | Jonassen et al. | |
| 8,003,605 | B2 | 8/2011 | Bayer et al. | |
| 8,067,362 | B2 * | 11/2011 | Kodra et al. | 514/6.3 |
| 2008/0076705 | A1 | 3/2008 | Kodra et al. | |
| 2008/0171695 | A1 | 7/2008 | Garibay et al. | |
| 2009/0074882 | A1 | 3/2009 | Havelund et al. | |
| 2009/0137454 | A1 | 5/2009 | Fynbo et al. | |
| 2009/0239785 | A1 | 9/2009 | Hubalek et al. | |
| 2010/0227796 | A1 | 9/2010 | Garibay et al. | |

FOREIGN PATENT DOCUMENTS

| | | | |
|---|---|---|---|
| EP | 894095 | | 2/1999 |
| EP | 0894095 | | 5/2003 |
| GB | 894095 | | 4/1962 |
| GB | 894095 | A | 4/1962 |
| GB | 1492997 | | 11/1977 |
| JP | 1254699 | | 5/1979 |
| JP | 57-67548 | | 4/1982 |
| JP | 57-67548 | | 10/1982 |
| JP | 1-254699 | | 9/1999 |
| WO | 91/12817 | A1 | 9/1991 |
| WO | 95/07931 | A1 | 3/1995 |
| WO | WO 95/07931 | | 3/1995 |
| WO | 96/29344 | | 9/1996 |
| WO | 97/31022 | A1 | 8/1997 |
| WO | WO 97/31022 | | 8/1997 |
| WO | 98/02460 | A1 | 1/1998 |
| WO | WO 98/02460 | | 1/1998 |
| WO | 02/094200 | A2 | 11/2002 |
| WO | 03/013573 | | 2/2003 |
| WO | 2005/005477 | A2 | 1/2005 |
| WO | WO 2005/005477 | | 1/2005 |
| WO | 2005/012347 | A2 | 2/2005 |
| WO | WO 2005/012347 | | 2/2005 |
| WO | 2005/047508 | A1 | 5/2005 |
| WO | 2006/008238 | A1 | 1/2006 |
| WO | 2006/082204 | | 8/2006 |
| WO | 2006/082205 | | 8/2006 |
| WO | 2007/074133 | A2 | 7/2007 |

(Continued)

OTHER PUBLICATIONS

Havelund, S et al., Pharmaceutical Research, The Mechanism of Protraction of Insulin Determir, a Long-Acting, Acylated Analog of Human Insulin, 2004, vol. 21, Part 8, pp. 1498-1505.

Hinds, K et al. Bioconjugate Chemistry. "Synthesis and Characterization of Poly(ethylene Glycol)-Insulin Conjugates." 2000. vol. 11. pp. 195-201.

Kochendoerfer, GG et al. Science. "Design and Chemical Synthesis of Homogeneous Polymer-Modified Erthropoiesis Protein." 2003. vol. 299(5608). pp. 884-887.

Tager H et al. Proceedings of the National Academy of Sciences of the USA. "Semisynthesis and Biological Activity of Porcine[LEUB24] Insulin and [LEUB25]Insulin." 1980. vol. 77(6). pp. 3182-3185.

English abstract of JP 1-254699; Sep. 21, 1999; Sagou Akira.

English abstract of JP 57-67548; Oct. 15, 1982; Harada Toshio.

Uchio, T. et al., Advanced Drug Delivery Reviews, vol. 35, p. 289-306 (1999).

Havelund, D.S. et al., Pharmaceutical Research, 2004, vol. 21, No. 8, pp. 1498-1504.

*Primary Examiner* — Bruce Campell

(74) *Attorney, Agent, or Firm* — Rosemarie R. Wilk-Orescan

(57) ABSTRACT

The present invention relates to insulin derivatives having a side chain attached either to the α-amino group of the N-terminal amino acid residue of the B chain or to the ϵ-amino group of a Lys residue present in the B chain of the parent insulin via an amide bond which side chain comprises at least one aromatic group; at least one free carboxylic acid group or a group which is negatively charged at neutral pH, a fatty acid moiety with 4 to 22 carbon atoms in the carbon chain; and possible linkers which link the individual components in the side chain together via amide bonds.

9 Claims, No Drawings

(56) References Cited

FOREIGN PATENT DOCUMENTS

| | | | |
|---|---|---|---|
| WO | 2007/096431 | A1 | 8/2007 |
| WO | 2007/128815 | A1 | 11/2007 |
| WO | 2007/128817 | A2 | 11/2007 |
| WO | WO 2007/128817 | | 11/2007 |
| WO | 2008/152106 | A1 | 12/2008 |
| WO | 2009/060071 | A1 | 5/2009 |
| WO | 2010/049488 | A1 | 5/2010 |
| WO | 2011/141407 | A1 | 11/2011 |

* cited by examiner

INSULIN DERIVATIVES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application is a continuation of U.S. application Ser. No. 11/814,019, filed Jul. 16, 2007, which is U.S.C. §371 National Stage application of International Application PCT/EP2006/050593, filed Feb. 1, 2006 (published as WO2006/082204), which claimed priority of Danish Patent Application PA 2005 00157, filed on Feb. 2, 2005; this application claims priority under 35 U.S.C. §119 of U.S. Provisional Application 60/651,035, filed Feb. 8, 2005; the contents of which are fully incorporated herein by reference.

FIELD OF THE INVENTION

The present invention relates to novel human insulin derivatives which are soluble at physiological pH values and have a prolonged profile of action. The invention also relates to methods of providing such derivatives, to pharmaceutical compositions containing them, to a method of treating diabetes and hyperglycaemia using the insulin derivatives of the invention and to the use of such insulin derivatives in the treatment of diabetes and hyperglycaemia.

BACKGROUND OF THE INVENTION

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of long acting insulin to cover the basal insulin requirement supplemented by bolus injections of a rapid acting insulin to cover the insulin requirement related to meals.

Long acting insulin compositions are well known in the art. Thus, one main type of long acting insulin compositions comprises injectable aqueous suspensions of insulin crystals or amorphous insulin. In these compositions, the insulin compounds utilized typically are protamine insulin, zinc insulin or protamine zinc insulin.

Certain drawbacks are associated with the use of insulin suspensions. Thus, in order to secure an accurate dosing, the insulin particles must be suspended homogeneously by gentle shaking before a defined volume of the suspension is withdrawn from a vial or expelled from a cartridge. Also, for the storage of insulin suspensions, the temperature must be kept within more narrow limits than for insulin solutions in order to avoid lump formation or coagulation.

Another type of long acting insulin compositions are solutions having a pH value below physiological pH from which the insulin will precipitate because of the rise in the pH value when the solution is injected. A drawback with these solutions is that the particle size distribution of the precipitate formed in the tissue on injection, and thus the release profile of the medication, depends on the blood flow at the injection site and other parameters in a somewhat unpredictable manner. A further drawback is that the solid particles of the insulin may act as a local irritant causing inflammation of the tissue at the site of injection.

Human insulin has three primary amino groups: the N-terminal group of the A-chain and of the B-chain and the ϵ-amino group of LysB29. Several insulin derivatives which are substituted in one or more of these groups are known in the prior art. Thus, U.S. Pat. No. 3,528,960 (Eli Lilly) relates to N-carboxyaroyl insulins in which one, two or three primary amino groups of the insulin molecule has a carboxyaroyl group.

GB Patent No. 1.492.997 (Nat. Res. Dev. Corp.) discloses insulin with a carbamyl substitution at NϵB29 with an alleged improved profile of hypoglycaemic effect.

JP laid-open patent application No. 1-254699 (Kodama Co., Ltd.) discloses insulin wherein a fatty acid is bound to the amino group of PheB1 or to the ϵ-amino group of LysB29 or to both of these. The stated purpose of the derivatisation is to obtain a pharmacologically acceptable, stable insulin preparation.

Insulins, which in the B30 position have an amino acid having at least five carbon atoms which cannot necessarily be coded for by a triplet of nucleotides, are described in JP laid-open patent application No. 57-067548 (Shionogi). The insulin analogues are claimed to be useful in the treatment of diabetes mellitus, particularly in patients who are insulin resistant due to generation of bovine or porcine insulin antibodies.

WO 95/07931 (Novo Nordisk A/S) discloses human insulin derivatives wherein the ϵ-amino group of LysB29 has a lipophilic substituent. These insulin derivatives have a prolonged profile of action and are soluble at physiological pH values.

GP 894095 discloses insulin derivatives wherein the N-terminal group of the B-chain and/or the &amino group of Lys in position B28, B29 or B30 has a substituent of the formula —CO—W—COOH where W can be a long chain hydrocarbon group. These insulin derivatives have a prolonged profile of action and are soluble at physiological pH values.

However, there is still a need for insulins having a more prolonged profile of action than the insulin derivatives known up till now and which at the same time are soluble at physiological pH values and have a potency which is comparable to that of human insulin.

SUMMARY OF THE INVENTION

The present invention is based on the recognition that the overall hydrophobicity of an insulin derivative molecule plays an important role for the in vivo potency of the derivative.

In one aspect the invention is related to insulin derivatives having a side chain attached either to the α-amino group of the N-terminal amino acid residue of the B chain or to an ϵ-amino group of a Lys residue present in the A or the B chain of the parent insulin moiety via an amide bond, which side chain comprises at least one aromatic group; at least one free carboxylic acid group or a group which is negatively charged at neutral pH, a fatty acid moiety with from 4 to 22 carbon atoms in the carbon chain; and possible one or more linkers linking the individual components in the side chain together via amide bonds, provided that the fatty acid moiety is not a divalent hydrocarbon chain of the formula $—(CH_2)_{v4}C_6H_4\ (CH_2)_{W1}—$ wherein v and w are integers or one of them is zero so that the sum of $v_4$ and $w_1$ is in the range of 6 to 30.

In one aspect the aromatic group is arylene or heteroarylene group which may be substituted with one or two groups selected from —COOH, —$SO_3H$, —$PO_3H_2$ and tetrazolyl.

In another aspect the aromatic group is a 5 to 7 membered heterocyclic ring system containing one or more heteroatoms selected from nitrogen, oxygen and sulphur.

In another aspect the aromatic group is 8 to 14 membered bi- or tricyclic heterocyclic ring system containing one or more heteroatoms selected from nitrogen, oxygen and sulphur.

In a further aspect the linker comprises 1-4 amino acid residues linked together via amide bonds of which at least one has a free carboxylic acid group or a group which is negatively charged at neutral pH.

In a further aspect the fatty acid moiety will have from 10-20, from 12-18 or from 14 to 18 carbon atoms.

In one aspect the insulin derivative according to the invention has the formula

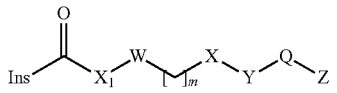

wherein Ins is the parent insulin moiety which via the α-amino group of the N-terminal amino acid residue of the B chain or an ϵ-amino group of an Lys residue present in the B chain of the insulin moiety is bound to the CO— group in the side chain via an amide bond;

$X_1$ is

—$(CH_2)_n$ where n is 1, 2, 3, 4, 5 or 6;

NR, where R is hydrogen or —$(CH_2)_p$—COOH; —$(CH_2)_p$—$SO_3H$; —$(CH_2)_p$—$PO_3H_2$; —$(CH_2)_p$—O—$SO_3H_2$; —$(CH_2)_p$—O—$PO_3H_2$; arylene substituted with 1 or 2-$(CH_2)_p$—O—COOH groups; —$(CH_2)_p$-tetrazolyl, where p is an integer in the range of 1 to 6;

—$(CR_1R_2)_q$—NR—CO—, where $R_1$ and $R_2$ independently of each other and independently for each value of q can be H, —COOH, or OH, q is 1-6 and R is defined as above;

—$((CR_3R_4)_{q1}$—NR—CO—$)_{2-4}$, where $R_3$ and $R_2$ independently of each other and independently for each value of $q_1$ can be H, —COOH, or OH, $q_1$ is 2-4 and R is defined as above; or a bond W is arylene or heteroarylene, which may be substituted with one or two groups selected from the group consisting of —COOH, —$SO_3H$, and —$PO_3H_2$ and tetrazolyl, or W is a bond;

m is 0, 1, 2, 3, 4, 5 or 6;

X is

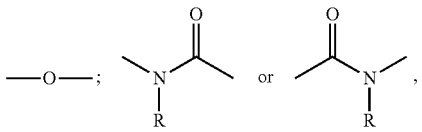

where R is defined as above; or a bond;

Y is

—$(CR_1R_2)_q$—NR—CO—, where $R_1$ and $R_2$ independently of each other and independently for each value of q can be H, —COOH, a bond or OH, and q is 1-6; and R is defined as above;

NR where R is defined as above;

—$((CR_3R_4)_{q1}$—NR—CO$)_{2-4}$—, where $R_3$ and $R_2$ independently of each other and independently for each value of $q_1$ can be H, —COOH, or OH, $q_1$ is 1-6 and R is defined as above; or a bond;

Q is

—$(CH_2)_r$— where r is an integer from 4 to 22;

a divalent hydrocarbon chain comprising 1, 2 or 3 —CH═CH— groups and a number of —$CH_2$— groups sufficient to give a total number of carbon atoms in the chain in the range of 4 to 22; or a divalent hydrocarbon chain of the formula $$—(CH_2)_s\text{-}Q_1\text{-}(C_6H_4)_{v1}\text{-}Q_2\text{-}(CH_2)_w\text{-}Q_3\text{-}(C_6H_4)_{v2}\text{-}Q_4\text{-}(CH_2)_t\text{-}Q_5\text{-}(C_6H_4)_{v3}\text{-}Q_6\text{-}(CH_2)_z—$$

wherein $Q_1$-$Q_6$ independently of each other can be O; S or a bond; s, w, t and z independently of each other are zero or an integer from 1 to 10 so that the sum of s, w, t and z is in the range from 4 to 22, and $v_1$, $v_2$, and $v_3$ independently of each other can be zero or 1, provided that when W is a bond then Q is not a divalent hydrocarbon chain of the formula —$(CH_2)_{v4}C_6H_4(CH_2)_{w1}$— wherein $v_4$ and $w_1$ are integers or one of them is zero so that the sum of $v_4$ and $w_1$ is in the range of 6 to 22; and Z is:

—COOH;

—CO-Asp;

—CO-Glu;

—CO-Gly;

—CO-Sar;

—$CH(COOH)_2$;

—$N(CH_2COOH)_2$;

—$SO_3H$

—$PO_3H_2$;

O—$SO_3H$;

O—$PO_3H_2$;

-tetrazolyl or where $W_1$ is arylene or heteroarylene substituted with one or two groups selected from —COOH, —$SO_3H$, and —$PO_3H_2$ and tetrazolyl;

provided that if W is a bond and $v_1$, $v_2$ and $v_3$ are all zero and $Q_{1-6}$ are all bonds, then Z is —O—$W_1$ and any $Zn^{2+}$ complex thereof.

In one aspect of the invention, the side is attached to the α-amino group of the N-terminal amino acid residue of the B chain of the parent insulin.

In another aspect of the invention, the side chain is attached to the ϵ-amino group of a Lys residue present in the B chain of the parent insulin. In a further aspect, the side chain is attached to the &amino group of a Lys residue present in position 28 or 29 of the B chain.

In one aspect W is phenylene. If the phenylene group comprises substituents such substituents can be attached in the 1,4; the 1,3 or the 1,2 positions.

In a further aspect W is isophtatalic acid or a derivatives thereof.

In another aspect W is 5-7 membered heterocyclic ring system comprising nitrogen, oxygen or sulphur or a 5 membered heterocyclic ring system comprising at least one oxygen such as furan.

Non limiting examples of heterocyclic ring systems are furylene, thienylene, pyrrolylene, oxazolylene, thiazolylene, imidazolylene, isoxazolylene, isothiazolylene, 1,2,3-triazolylene, 1,2,4-triazolylene, pyranylene, pyridylene, pyridazinylene, and pyrimidinylene.

In one aspect n is 1 or 2. In another aspect q is 1, 2 or 3. In a further aspect m is 1 or 2.

In one aspect Q is —$(CH_2)_r$— where r is an integer from 4 to 22, 8 to 20, 12 to 20, 12-16, 10-16; 10-20, 14-18 or 14-16.

In another aspect Q is a divalent hydrocarbon chain comprising 1, 2 or 3-CH═CH— groups and a number of —$CH_2$— groups sufficient to give a total number of carbon atoms in the chain in the range of 4 to 22, 8 to 20, 12 to 20, 12-16, 10-16; 10-20, 14-18 or 14-16.

The fatty diacid will typically comprise from 4 to 18, from 6 to 18, from 8 to 16, from 8 to 22, from 8 to 17, from 8 to 15, from 10 to 18, from 10 to 16 and from 6 to 17 carbon atoms in the carbon chain.

Non limiting examples of the fatty diacid moiety are diacids with the formula HOOC—$(CH_2)_{r1}$—COOH, where $r_1$ is from 4 to 22

In one aspect $Q_1$-$Q_6$ are all a bond and the sum of s, w, t and z is from 6 to 18.

In another aspect $Q_1$-$Q_6$ are all a bond, the sum of s and z is from 6 to 18, and w and t are zero.

In another aspect $Q_1$-$Q_6$ are all a bond, $v_1$ is zero, the sum of s and z is from 6 to 18, and w and t are zero.

In another aspect two of $Q_1$-$Q_6$ are oxygen and the other Q's are a bonds.

In one aspect $Q_1$, $Q_2$, $Q_5$ and -$Q_6$ are all a bond, $v_2$ is 1 and $v_1$ and $v_3$ are zero.

In another aspect $Q_1$, $Q_2$, $Q_5$ and -$Q_6$ are all a bond, $v_2$ is 1 and $v_1$ and $v_3$ are zero and $Q_3$ and $Q_4$ are oxygen.

In one aspect R is hydrogen or —$(CH)_p$ where p is 1-3.

In one aspect $X_1$ is —$(CH_2)_{1-4}$—NH—CO—.

In another aspect $X_1$ and Y are a bond and X is

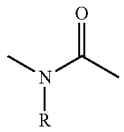

where R is —$(CH_2)_p$—COOH, where p is 1-4 or 1-2.

In another aspect X is a bond or α- or γ-Glu.

In one aspect Z is —COOH

In another aspect Z is —CO-Asp.

In another aspect Z is —CO-Glu.

In another aspect Z is —CO-Gly.

In another aspect Z is —CO-Sar.

In another aspect Z is —$CH(COOH)_2$.

In another aspect Z is —$N(CH_2COOH)_2$.

In another aspect Z is —$SO_3H$.

In another aspect Z is —$PO_3H$.

In another aspect Z is O—$SO_3H$;

In another aspect Z is O—$PO_3H_2$;

In another aspect Z is tetrazolyl.

In another aspect Z is —$OC_6H_4COOH$.

DETAILED DESCRIPTION OF THE INVENTION

The present insulin derivatives are characterized by having a side chain attached to a Lys group in either the B or the A chain or to the N-terminal amino group in the B-chain of the parent insulin molecule which side chain comprises an aromatic group and a fatty diacid moity.

The insulin derivative according to the invention is furthermore characterized in having at least one free carboxylic acid group in the side chain and may comprise up to 2 or three free carboxylic acid group or a group which is negatively charged at neutral pH.

The insulin derivatives will only contain one lysine residue. This lysine residue may either be in position B29 as in human insulin or in one of position B3, B30 or B23 to B28.

The insulin moiety—in the present text also referred to as the parent insulin—of an insulin derivative according to the invention can be a naturally occurring insulin such as human insulin or porcine insulin. Alternatively, the parent insulin can be an insulin analogue.

In one group of parent insulin analogues, the amino acid residue at position A21 is Asn.

In another group of parent insulin analogues, the amino acid residue at position A21 is Gly. Specific examples from this group of analogues are $Gly^{A21}$ human insulin, $Gly^{A21}$ des(B30)human insulin; and $Gly^{A21}Arg^{B31}Arg^{B32}$ human insulin.

In another group of parent insulin analogues, the amino acid residue at position B1 has been deleted. A specific example from this group of parent insulin analogues is desB1 human insulin.

In another group of parent insulin analogues, the amino acid residue at position B30 has been deleted. A specific example from this group of parent insulin analogues is desB30 human insulin.

In another group of parent insulin analogues, the amino acid residue at position B28 is Asp. A specific example from this group of parent insulin analogues is $Asp^{B28}$ human insulin.

In another group of parent insulin analogues, the amino acid residue at position B28 is Lys and the amino acid residue at position B29 is Pro. A specific example from this group of parent insulin analogues is $Lys^{B28}Pro^{B29}$ human insulin.

In another group of parent insulin analogues the amino acid residue in position B30 is Lys and the amino acid residue in position B29 is any codable amino acid except Cys, Met, Arg and Lys. An example is an insulin analogue where the amino acid residue at position B29 is Thr and the amino acid residue at position B30 is Lys. A specific example from this group of parent insulin analogues is $Thr^{B29}Lys^{B30}$ human insulin.

In another group of parent insulin analogues, the amino acid residue at position B3 is Lys and the amino acid residue at position B29 is Glu. A specific example from this group of parent insulin analogues is $Lys^{B3}Glu^{B29}$ human insulin.

Examples of insulin derivatives according to the invention are the following compounds:

$N^{\epsilon B29}$—[N..(HOOC$(CH_2)_{14}$CO)—N-(carboxyethyl)-$CH_2$-para $C_6H_4$CO] desB30 human insulin;

$N^{\epsilon B29}$—[N—(HOOC$(CH_2)_{13}$CO)—N-(carboxyethyl)-$CH_2$-para $C_6H_4$CO] desB30 human insulin;

$N^{\epsilon B29}$—[N—(HOOC$(CH_2)_{15}$CO)—N-(carboxyethyl)-$CH_2$-para $C_6H_4$CO] desB30 human insulin;

$N^{\epsilon B29}$—[N—(HOOC$(CH_2)_{16}$CO)—N-(carboxyethyl)-$CH_2$-para $C_6H_4$CO] desB30 human insulin;

$N^{\epsilon B29}$—[N—(HOOC$(CH_2)_{14}$CO)—N-(carboxymethyl)-para $C_6H_4$CO] desB30 human insulin;

$N^{\epsilon B29}$—[N—(HOOC$(CH_2)_{14}$CO)—N-(carboxyethyl)-$CH_2$-(2,5-furanylene)CO] desB30 human insulin;

$N^{\epsilon B29}$—[N—(HOOC($CH_2$)$_{14}$CO)—N-(carboxyethyl)-$CH_2$-meta-$C_6H_4$CO] desB30 human insulin;

$N^{\epsilon B29}$—[N—(HOOC($CH_2$)$_{14}$CO)—N-(carboxyethyl)-$CH_2$-ortho $C_6H_4$CO] desB30 human insulin;

$N^{\epsilon B29}$—[N—(HOOC($CH_2$)$_{14}$CO)—NH—$CH_2$-para-$C_6H_4$CO-gamma-Glu] desB30 human insulin;

$N^{\epsilon B29}$-[5-N—(HOOC($CH_2$)$_{14}$CO)NH-(3-COOH—$C_6H_3$CO)]desB30 human insulin;

$N^{\epsilon B29}$-[5-N..(HOOC($CH_2$)$_{16}$CO)NH-(3-COOH—$C_6H_3$CO)]desB30 human insulin;

$N^{\epsilon B29}$-[5-N—(HOOC($CH_2$)$_{16}$CO)—N-(carboxyethyl-Gly)-N-(3-COOH—$C_6H_3$CO)]desB30 human insulin and $N^{\epsilon B29\epsilon}$-[3-Carboxy-5-(octadecandioyl-N-carboxyethyl-Gly)amino-benzoyl] desB30 human insulin.

Insulin derivatives according to the invention may be provided in the form of essentially zinc free compounds or in the form of zinc complexes. When zinc complexes of an insulin derivative according to the invention are provided, two $Zn^{2+}$ ions, three $Zn^{2+}$ ions or four $Zn^{2+}$ ions can be bound to each insulin hexamer. Solutions of zinc complexes of the insulin derivatives will contain mixtures of such species.

In a further aspect of the invention, a pharmaceutical composition comprising a therapeutically effective amount of an insulin derivative according to the invention together with a pharmaceutically acceptable carrier can be provided for the treatment of type 1 diabetes, type 2 diabetes and other states that cause hyperglycaemia in patients in need of such a treatment. An insulin derivative according to the invention can be used for the manufacture of a pharmaceutical composition for use in the treatment of type 1 diabetes, type 2 diabetes and other states that cause hyperglycaemia.

In a further aspect of the invention, there is provided a pharmaceutical composition for treating type 1 diabetes, type 2 diabetes and other states that cause hyperglycaemia in a patient in need of such a treatment, comprising a therapeutically effective amount of an insulin derivative according to the invention in mixture with an insulin or an insulin analogue which has a rapid onset of action, together with pharmaceutically acceptable carriers and additives.

In a further aspect of the invention, there is provided a method of treating type 1 diabetes, type 2 diabetes and other states that cause hyperglycaemia in a patient in need of such a treatment, comprising administering to the patient a therapeutically effective amount of an insulin derivative according to the invention together with a pharmaceutically acceptable carrier and pharmaceutical acceptable additives.

In a further aspect of the invention, there is provided a method of treating type 1 diabetes, type 2 diabetes and other states that cause hyperglycaemia in a patient in need of such a treatment, comprising administering to the patient a therapeutically effective amount of an insulin derivative according to the invention in mixture with an insulin or an insulin analogue which has a rapid onset of action, together with a pharmaceutically acceptable carrier and pharmaceutical acceptable additives.

In a further aspect of the invention, there is provided a use of an insulin derivative according to the invention for the manufacture of a medicament for blood glucose lowering.

In a further aspect of the invention, there is provided a use of an insulin derivative according to the invention for the manufacture of a medicament for treatment of diabetes.

In a further aspect, the present invention relates to insulin derivatives which have an overall hydrophobicity which is essentially similar to that of human insulin.

In one aspect, the insulin derivatives of the present invention have a hydrophobic index, k'rel, which is in the range from about 0.02 to about 10, from about 0.1 to about 5; from about 0.5 to about 5; or from about 0.5 to about 2.

In another aspect, the invention relates to a pharmaceutical composition comprising an insulin derivative according to the invention which is soluble at physiological pH values.

In another aspect, the invention relates to a pharmaceutical composition comprising an insulin derivative according to the invention which is soluble at pH values in the interval from about 6.5 to about 8.5.

In another aspect, the invention relates to a pharmaceutical composition with a prolonged profile of action which comprises an insulin derivative according to the invention.

In another aspect, the invention relates to a pharmaceutical composition which is a solution containing from about 120 nmol/ml to about 2400 nmol/ml, from about 400 nmol/ml to about 2400 nmol/ml, from about 400 nmol/ml to about 1200 nmol/ml, from about 600 nmol/ml to about 2400 nmol/ml, or from about 600 nmol/ml to about 1200 nmol/ml of an insulin derivative according to the invention or of a mixture of the insulin derivative according to the invention with a rapid acting insulin analogue.

The starting product for the acylation, the parent insulin or insulin analogue or a precursor thereof can be produced by either well-know organic synthesis or by well known recombinant production in suitable transformed microorganisms. Thus the insulin starting product can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture. As an example desB(30) human insulin can be produced from a human insulin precursor B(1-29)-Ala-Ala-Lys-A(1-21) which is produced in yeast as disclosed in U.S. Pat. No. 4,916,212. This insulin precursor can then be converted into desB30 human insulin by ALP cleavage of the Ala-Ala-Lys peptide chain to give desB30 human insulin which can then be acylated to give the present insulin derivatives.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the parent insulin may suitably be of genomic or cDNA origin, for instance obtained by preparing a genomic or cDNA library and screening for DNA sequences coding for all or part of the polypeptide by hybridisation using synthetic oligonucleotide probes in accordance with standard techniques (see, for example, Sambrook, J, Fritsch, E F and Maniatis, T, Molecular Cloning: A Laboratory Manual, Cold Spring Harbor Laboratory Press, New York, 1989). The DNA sequence encoding the polypeptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. The DNA sequence may also be prepared by polymerase chain reaction using specific primers, for instance as described in U.S. Pat. No. 4,683,202 or Saiki et al., Science 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the parent insulin in a variety of host cells are well known in the art, cf. for instance Sambrook et al., supra.

The DNA sequence encoding the parent insulin may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the parent insulin, the promoter and optionally the terminator and/or secretory signal sequence, respectively, and to insert them into suitable vectors containing the information necessary for replication, are well known to persons skilled in the art (cf., for instance, Sambrook, J, Fritsch, E F and Maniatis, T, Molecular Cloning: A Laboratory Manual, Cold Spring Harbor Laboratory Press, New York, 1989).

The host cell into which the DNA sequence or the recombinant vector is introduced may be any cell which is capable of producing the parent insulin and includes bacteria, yeast, fungi and higher eukaryotic cells. Examples of suitable host cells well known and used in the art are, without limitation, E. coli, Saccharomyces cerevisiae, or mammalian BHK or CHO cell lines.

The parent insulin molecule is then converted into the insulin derivatives of the invention by introducing of the relevant side chain in either the B1 position or in the chosen Lys position in the B-chain. The side chain can be introduced by any convenient method and many methods are disclosed in the prior art for acylation of an amino group. More details will appear from the following examples.

Pharmaceutical Compositions

Pharmaceutical compositions containing an insulin derivative according to the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. Further options are to administer the insulin nasally or pulmonally, preferably in compositions, powders or liquids, specifically designed for the purpose.

Injectable compositions of the insulin derivatives of the invention can be prepared using the conventional techniques of the pharmaceutical industry which involve dissolving and mixing the ingredients as appropriate to give the desired end product. Thus, according to one procedure, an insulin derivative according to the invention is dissolved in an amount of water which is somewhat less than the final volume of the composition to be prepared. An isotonic agent, a preservative and a buffer is added as required and the pH value of the solution is adjusted..if necessary..using an acid, e.g. hydrochloric acid, or a base, e.g. aqueous sodium hydroxide as needed. Finally, the volume of the solution is adjusted with water to give the desired concentration of the ingredients.

In a further aspect of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative aspect of the invention.

In a further aspect of the invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further aspect of the invention the preservative is present in a concentration from 0.1 mg/ml to 20 mg/ml. In a further aspect of the invention the preservative is present in a concentration from 0.1 mg/ml to 5 mg/ml. In a further aspect of the invention the preservative is present in a concentration from 5 mg/ml to 10 mg/ml. In a further aspect of the invention the preservative is present in a concentration from 10 mg/ml to 20 mg/ml. Each one of these specific preservatives constitutes an alternative aspect of the invention. The use of a preservative in pharmaceutical compositions is well-known to the skilled person. For convenience reference is made to Remington: The Science and Practice of Pharmacy, $19^{th}$ edition, 1995.

In a further aspect of the invention the formulation further comprises an isotonic agent which may be selected from the group consisting of a salt (e.g. sodium chloride), a sugar or sugar alcohol, an amino acid (e.g. glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one aspect the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one aspect the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one aspect, the sugar or sugar alcohol concentration is between about 1 mg/ml and about 150 mg/ml. In a further aspect of the invention the isotonic agent is present in a concentration from 1 mg/ml to 50 mg/ml. In a further aspect of the invention the isotonic agent is present in a concentration from 1 mg/ml to 7 mg/ml. In a further aspect of the invention the isotonic agent is present in a concentration from 8 mg/ml to 24 mg/ml. In a further aspect of the invention the isotonic agent is present in a concentration from 25 mg/ml to 50 mg/ml. Each one of these specific isotonic agents constitutes an alternative aspect of the invention. The use of an isotonic agent in pharmaceutical compositions is well-known to the skilled person. For convenience reference is made to Remington: The Science and Practice of Pharmacy, $19^{th}$ edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid) and sodium phosphate.

A composition for nasal administration of an insulin derivative according to the present invention may, for example, be prepared as described in European Patent No. 272097 (to Novo Nordisk A/S).

Compositions containing insulins of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the insulin derivative of this invention be determined for each individual patient by those skilled in the art in a similar way as for known insulin compositions.

Where expedient, the insulin derivatives of this invention may be used in mixture with other types of insulin, e.g. insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly & Co.).

In a further aspect of the present invention the present compounds are administered in combination with one or more further active substances in any suitable ratios. Such further active agents may be selected from antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic β-cells eg potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

DEFINITIONS

With "desB30" or "B(1-29)" is meant a natural insulin B chain or an analogue thereof lacking the B30 amino acid residue and "A(1-21)" means the natural insulin A chain or an analogue thereof. The C-peptide and its amino acid sequence are indicated in the three letter amino acid code. DesB30, desB29 human insulin is a human insulin lacking B29 and B30.

With "B1", "A1" etc. is meant the amino acid residue in position 1 in the B chain of insulin (counted from the N-terminal end) and the amino acid residue in position 1 in the A chain of insulin (counted from the N-terminal end), respectively. The amino acid residue in a specific position may also be denoted as e.g. $Phe^{B1}$ which means that the amino acid residue in position B1 is a phenylalanine residue.

With "Insulin" as used herein is meant human insulin with disulfide bridges between $Cys^{A7}$ and $Cys^{B7}$ and between $Cys^{A20}$ and $Cys^{B19}$ and an internal disulfide bridge between $Cys^{A6}$ and $Cys^{A11}$, porcine insulin and bovine insulin.

By "insulin analogue" as used herein is meant a polypeptide which has a molecular structure which formally can be derived from the structure of a naturally occurring insulin, for example that of human insulin, by deleting and/or substituting at least one amino acid residue occurring in the natural insulin and/or by adding at least one amino acid residue. The added and/or substituted amino acid residues can either be codable amino acid residues or other naturally occurring amino acid residues or purely synthetic amino acid residues.

The insulin analogues may be such wherein position 28 of the B chain may be modified from the natural Pro residue to Asp, Lys, or Ile. Lys in position B29 may also be modified to Pro. Furthermore B30 may be Lys in which case B29 is different from Cys, Met, Arg and Lys.

Also, Asn at position A21 may be modified to Ala, Gln, Glu, Gly, His, Ile, Leu, Met, Ser, Thr, Trp, Tyr or Val, in particular to Gly, Ala, Ser, or Thr and in particular to Gly. Furthermore, Asn at position B3 may be modified to Lys or Asp. Further examples of insulin analogues are des(B30) human insulin, insulin analogues wherein one or both of B1 and B2 have been deleted; insulin analogues wherein the A-chain and/or the B-chain have an N-terminal extension and insulin analogues wherein the A-chain and/or the B-chain have a C-terminal extension. Further insulin analogues are such wherein one or more of B26-B30 have been deleted.

By "insulin derivative" as used herein is meant a naturally occurring insulin or an insulin analogue which has been chemically modified, e.g. by introducing a side chain in one or more positions of the insulin backbone or by oxidizing or reducing groups of the amino acid residues in the insulin or by acylating a free amino group or a hydroxy group.

The expression "a codable amino acid" or "a codable amino acid residue" is used to indicate an amino acid or amino acid residue which can be coded for by a triplet ("codon") of nucleotides.

hGlu is homoglutamic acid.

α-Asp is the L-form of —HNCH(CO—)$CH_2$COOH.

β-Asp is the L-form of —HNCH(COOH)$CH_2$CO—.

α-Glu is the L-form of —HNCH(CO—)$CH_2CH_2$COOH.

γ-Glu is the L-form of —HNCH(COOH)$CH_2CH_2$CO—.

α-hGlu is the L-form of —HNCH(CO—)$CH_2CH_2CH_2$COOH.

δ-hGlu is the L-form of —HNCH(COOH)$CH_2CH_2CH_2$CO—.

β-Ala is —NH—$CH_2$—$CH_2$—CO—.

Sar is sarcosine (N-methylglycine).

The expression "an amino acid residue having a carboxylic acid group in the side chain" designates amino acid residues like Asp, Glu and hGlu. The amino acids can be in either the L- or D-configuration. If nothing is specified it is understood that the amino acid residue is in the L configuration.

The expression "an amino acid residue having a neutral side chain" designates amino acid residues like Gly, Ala, Val, Leu, Ile, Phe, Pro, Ser, Thr, Cys, Met, Tyr, Asn and Gln.

With "activated acid" is meant a carboxylic acid in which an activated leaving group has been attached to the acyl carbon enabling reaction with an amino group under formation of an amide bond and release of the leaving group. Activated fatty acids may be activated esters of fatty acids, activated amides of fatty acids and anhydrides or chlorides. Activated fatty acid includes derivatives thereof such as N-hydroxybenzotriazole and N-hydroxysuccinimide.

With "fatty acid" is meant a linear or branched carboxylic acids having at least 2 carbon atoms and being saturated or unsaturated. Examples of fatty acids are capric acid, lauric acid, tetradecanoic acid (myristic acid), pentadecanoic acid, palmitic acid, heptadecanoic acid, and stearic acid.

The term "arylene" as used herein is intended to include divalent, carbocyclic, aromatic ring systems such as 6 membered monocyclic and 9 to 14 membered bi- and tricyclic, divalent, carbocyclic, aromatic ring systems. Representative examples are phenylene, biphenylylene, naphthylene, anthracenylene, phenanthrenylene, fluorenylene, indenylene, azulenylene and the like. Arylene is also intended to include the partially hydrogenated derivatives of the ring systems enumerated above. Non-limiting examples of such partially hydrogenated derivatives are 1,2,3,4-tetrahydronaphthylene, 1,4-dihydronaphthylene and the like.

The term "heteroarylene" as used herein is intended to include divalent, aromatic, heterocyclic ring systems containing one or more heteroatoms selected from nitrogen, oxygen and sulfur such as 5 to 7 membered monocyclic and 8 to 14 membered bi- and tricyclic aromatic, heterocyclic ring systems containing one or more heteroatoms selected from nitrogen, oxygen and sulfur. Representative examples are furylene, thienylene, pyrrolylene, oxazolylene, thiazolylene, imidazolylene, isoxazolylene, isothiazolylene, 1,2,3-triazolylene, 1,2,4-triazolylene, pyranylene, pyridylene, pyridazinylene, pyrimidinylene, pyrazinylene, 1,2,3-triazinylene, 1,2,4-triazinylene, 1,3,5-triazinylene, 1,2,3-oxadiazolylene, 1,2,4-oxadiazolylene, 1,2,5-oxadiazolylene, 1,3,4-oxadiazolylene, 1,2,3-thiadiazolylene, 1,2,4-thiadiazolylene, 1,2,5-thiadiazolylene, 1,3,4-thiadiazolylene, tetrazolylene, thiadiazinylene, indolylene, isoindolylene, benzofurylene, benzothienylene, indazolylene, benzimidazolylene, benzthiazolylene, benzisothiazolylene, benzoxazolylene, benzisoxazolylene, purinylene, quinazolinylene, quinolizinylene, quinolinylene, isoquinolinylene, quinoxalinylene, naphthyridinylene, pteridinylene, carbazolylene, azepinylene, diazepinylene, acridinylene and the like. Heteroaryl is also intended to include the partially hydrogenated derivatives of the ring systems enumerated above. Non-limiting examples of such partially hydrogenated derivatives are 2,3-dihydrobenzofuranylene, pyrrolinylene, pyrazolinylene, indolinylene, oxazolidinylene, oxazolinylene, oxazepinylene and the like.

The term "optionally substituted" as used herein means that the groups in question are either unsubstituted or substituted with one or more of the substituents specified. When the groups in question are substituted with more than one substituent the substituents may be the same or different.

When an insulin derivative according to the invention is stated to be "soluble at physiological pH values" it means that the insulin derivative can be used for preparing insulin compositions that are fully dissolved at physiological pH values. Such favourable solubility may either be due to the inherent properties of the insulin derivative alone or a result of a favourable interaction between the insulin derivative and one or more ingredients contained in the vehicle.

The following abbreviations and methods have been used in the specification and examples:

Bzl=Bn: benzyl

DIPEA=DIEA: N,N-diisopropylethylamine

DMF: N,N-dimethylformamide tBu: tert-butyl

TSTU: O—(N-succinimidyl)-1,1,3,3-tetramethyluronium tetrafluoroborate

THF: Tetrahydrofuran

EtOAc=AcOEt: Ethyl acetate

DIPEA: Diisopropylethylamine

HOAt: 1-Hydroxy-7-azabenzotriazole

TEA: triethyl amine

Su: succinimidyl=2,5-dioxo-pyrrolidin-1-yl

TFA: trifluoracetic acid

DCM: dichloromethane

DMSO: dimethyl sulphoxide

HOBt: 1-hydroxybenzotriazole

TRIS: Triisopropylsilane

EDAC: N-(3-dimethylaminopropyl)-N'-ethylcarbodiimide hydrochloride

NMP: 1-methyl-2-pyrrolidone

TLC: Thin Layer Chromatography
RT: room temperature
$R_t$: Retention time
MeOH: methanol
DCC: Dicyclohexylcarondiimide
AcOH: Acetic acid
DIC: Diisopropylcarbodiimide All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

HPLC-MS: The following instrumentation was used:
Hewlett Packard series 1100 G1312A Bin Pump
Hewlett Packard series 1100 Column compartment
Hewlett Packard series 1100 G1315A DAD diode array detector
Hewlett Packard series 1100 MSD
Sedere 75 Evaporative Light Scattering detector The instrument was controlled by HP Chemstation software.

The HPLC pump was connected to two eluent reservoirs containing:
A: 0.01% TFA in water
B: 0.01% TFA in acetonitrile The analysis is performed at 40 C by injecting an appropriate volume of the sample (preferably 1 μl) onto the column which is eluted with a gradient of acetonitrile.

The HPLC conditions, detector settings and mass spectrometer settings used are giving in the following:
Column: Waters Xterra MS C-18 X 3 mm id 5 μm
Gradient: 5%-100% acetonitrile linear during 7.5 min at 1.5 ml/min
Detection: 210 nm (analogue output from DAD)
ELS (analogue output from ELS)

After the DAD the flow was divided yielding approx 1 ml/min to the ELS and 0.5 ml/min to the MS.

HPLC-MS (method fast grad): The following instrumentation was used:
Hewlett Packard series 1100 G1312A Bin Pump
Hewlett Packard series 1100 Column compartment
Hewlett Packard series 1100 G1315A DAD diode array detector
Hewlett Packard series 1100 MSD
Sedere 75 Evaporative Light Scattering detector The instrument was controlled by HP Chemstation software.

The HPLC pump was connected to two eluent reservoirs containing:
A: 0.05% TFA in water
B: 0.05% TFA in acetonitrile The analysis is performed at 40 C by injecting an appropriate volume of the sample (preferably 1 μl) onto the column which is eluted with a gradient of acetonitrile.

The HPLC conditions, detector settings and mass spectrometer settings used are giving in the following:
Column: Waters Xterra MS C-18 X 3 mm id 5 μm
Gradient: 5%-95% acetonitrile linear during 3 min at 2.7 ml/min
Detection: 210 nm (analogue output from DAD)
ELS (analogue output from ELS)

After the DAD the flow was divided yielding approx 1 ml/min to the ELS and 0.5 ml/min to the MS.

HPLC-MS (50-99)

The same instruments and procedure as in the fast grad method is used. The only difference is that the gradient runs from 50-99% acetonitrile.

HPLC (Neutral)
Buffer A: 10 mMtris, 15 mM $(NH_4)_2SO_4$, pH adjusted to 7.3 with 4N $H_2SO_4$, 20% v/v acetonitrile
Buffer B: 80% v/v acetonitrile
Flow: 1.5 ml/min
Gradient: 0-20 min 10-50% B
Column: Phenomerex, Jupiter 4.6 mm×150 mm, $C_4$, 5μ, 300 Å
Column temperature: 40° C.

HPLC-MS (Sciex)

The following instrumentation is used:
Hewlett Packard series 1100 G1312A Bin Pump
Hewlett Packard series 1100 G13 15A DAD diode array detector
Sciex3000 triplequadropole mass spectrometer
Gilson 215 micro injector
Sedex55 evaporative light scattering detector Pumps and detectors are controlled by MassChrom 1.1.1 software running on a Macintosh G3 computer. Gilson Unipoint Version 1.90 controls the auto-injector.

The HPLC pump is connected to two eluent reservoirs containing:
A: 0.01% TFA in water
B: 0.01% TFA in acetonitrile The analysis is performed at room temperature by injecting an appropriate volume of the sample (preferably 10 μl) onto the column, which is eluted, with a gradient of acetonitrile. The eluate from the column passed through the UV detector to meet a flow splitter, which passed approximately 30 μl/min (1/50) through to the API Turbo ion-spray interface of API 3000 spectrometer. The remaining 1.48 ml/min (49/50) is passed through to the ELS detector.

The HPLC conditions, detector settings and mass spectrometer settings used are giving in the following table.

| | |
|---|---|
| Column | Waters X-Terra C18, 5μ, 50 mm × 3 mm id |
| Gradient | 5%-90% acetonitrile linearly during 7.5 min at 1.5 ml/min |
| Detection | 210 nm (analogue output from DAD) |
| MS | ionisation mode API Turbo ion-spray |
| ELS | Gain 8 and 40° C. |

Example 1

General Procedure A, Acylation Using desB30 Human Insulin $N^{\epsilon B29}$—[N—HOOC$(CH_2)_{14}$CO)—N-(carboxyethyl)-$CH_2$-para-$C_6H_4$CO] desB30 human insulin Step 1: Synthesis of 4-[(2-tert-Butoxycarbonylethylamino)methyl]benzoic acid

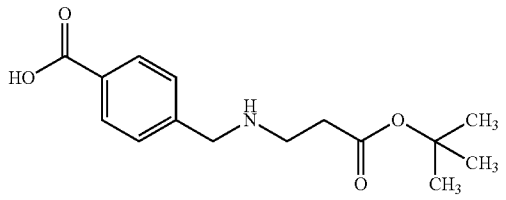

Tert-butyl 3-aminopropanoate hydrochloride (5 g, 27.7 mmol) was dissolved in methanol (150 mL). Diisopropylethylamin (4.73 mL, 27.7 mmol) was added followed by 4-carboxybenzaldehyd. The mixture is heated to reflux for 1 hour. After cooling to room temperature sodium cyanoborohydride (1.77 g, 22.1 mmol) was added under nitrogen and stirred for 1 hour at room temperature. Acetic acid (15 mL) was added and the mixture was stirred for an additional 1 hour. The mixture was poured into water (300 mL) and stirred at room temperature over night. The water solution was washed with ethyl acetate (3×250 mL). The organic phase dried ($Na_2SO_4$) and solvent removed in vacuo to yield the crude product as an oil which solidifies by standing. The crude product was used in the next step without further purification.

HPLC-MS: m/z=(280); $R_t$=2.09 min.

Step 2: Synthesis of 4-{[(2-tert-Butoxycarbonylethyl)-(15-tert-butoxycarbonyl-pentadecanoyl)amino]methyl}benzoic acid

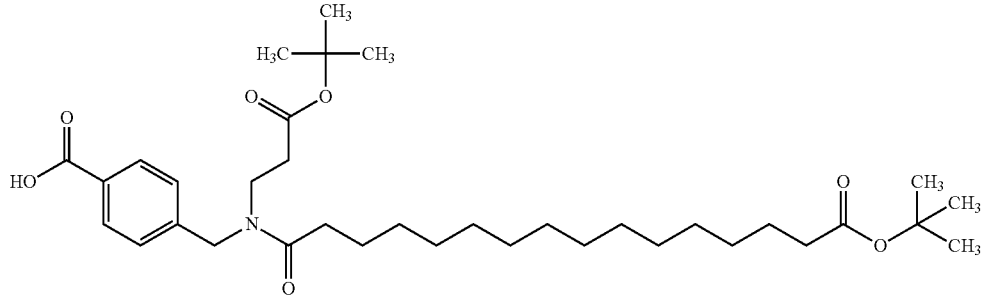

Hexadecanedioic acid mono-tert-butyl ester (0.3 g, 0.88 mmol) was dissolved in ethyl acetate. N-Ethyl-N-(3-dimethylaminopropyl)-carbodiimide hydrochloride (0.167 g, 0.88 mmol) and 1-hydroxy-7-azabenzotriazole (0.119 g, 0.88 mmol) was added and the mixture was stirred at 50° C. for 1 hour. After cooling to room temperature, diisopropylethylamin (0.45 mL, 2.63 mmol) was added followed by 4-[(2-tert-Butoxycarbonylethylamino)methyl]benzoic acid (0.489 g, 1.75 mmol). The mixture was stirred overnight under nitrogen at room temperature. The mixture was separated between ethyl acetate (100 mL) and water (2×50 mL). The organic phase was dried ($Na_2SO_4$), solvent removed in vacuo. The crude product was purified by RP-HPLC on C18-column, buffer A: 0.1% TFA, buffer B: MeCN+0.1% TFA; gradient 80-100% B to yield the title compound (145 mg, 27%).

$^1$H NMR (Acetone-$d_6$): δ 8.04 (dd, 2H), 7.40 (dd, 2H), 4.75 (d, 2H), 3.60 (q, 2H), 1.55 (m, 4H), 1.45-1.15 (m, 38H).

Step 3: Synthesis of 4-{[(2-tert-Butoxycarbonylethyl)-(15-tert-butoxycarbonyl-pentadecanoyl)amino]methyl}benzoic acid 2,5-dioxopyrrolidin-1-yl ester

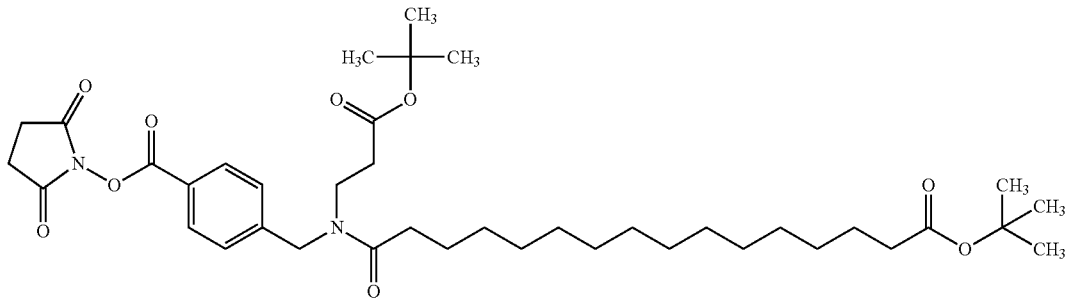

4-{[(2-tert-Butoxycarbonylethyl)-(15-tert-butoxycarbonyl-pentadecanoyl)amino]methyl}benzoic acid (70 mg, 0.12 mmol) was dissolved in THF (5 mL). The mixture was cooled with an ice bath. Diisopropylethylamin (0.024 mL, 0.14 mmol) and O—(N-succinimidyl)-N,N,N',N'-tetramethyluronium tetrafluoroborate (42 mg, 0.14 mmol) was added. The mixture was stirred under nitrogen at 0° C. After 30 minutes the ice cooling was removed and the mixture was stirred for an additional 3 hours. Solvent removed in vacuo flowed by reevaporation from toluene. The crude product was dissolved in ethyl acetate (25 mL), washed with water (10 mL). The organic phase dried ($Na_2SO_4$), solvent removed in vacuo to yield the title compound (73 mg, 87%) which was used in subsequent step.

HPLC-MS: m/z=(723 (M+Na)); $R_t$=6.24 min.

Step 4: Synthesis of B29N(esp)(4-{[(2-Carboxyethyl)-(15-carboxypentadecanoyl)amino]-methyl}benzoyl) desB30 human insulin

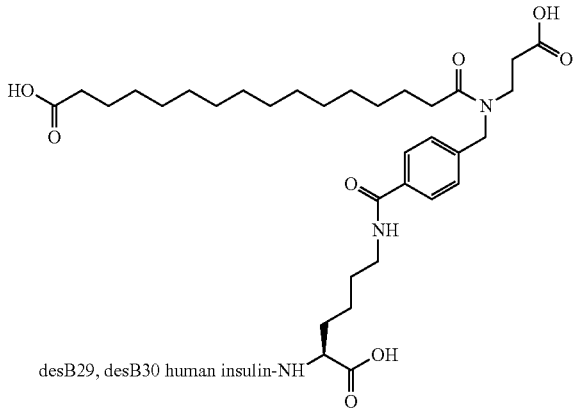

Human DesB30 insulin (594 mg, 0.104 mmol) was dissolved in aqueous $Na_2CO_3$ (100 mM, 5 mL). 4-{[(2-tert-Butoxycarbonylethyl)-(15-tert-butoxycarbonyl-pentadecanoyl)amino]methyl}benzoic acid 2,5-dioxopyrrolidin-1-yl ester (73 mg, 0.104 mmol) was dissolved in acetonitrile (3 mL) and added. The mixture was stirred very slowly for 1 hour at RT. pH was adjusted to 5.5 with aqueous HCl (1N) and the suspension was allowed to stand for 10 minutes at 0° C. The precipitate was isolated by centrifugation and treated with TFA/water (95:5, 12 mL) for 30 minutes. Poured into ice cooled diethylether (30 mL), and the crude product was isolated by centrifuge and purified with RP-HPLC on a Waters Prep LC2000, on C18, 5 cm×20 cm, flow 20 ml/min using acetonitrile/water 33-53% gradient containing 0.1% TFA. Fraktions containing product was collected and lyophilized. To the lyophilized material was added water (7.2 mL) and pH adjusted to 8.98 with 1 N+0.1 N NaOH. The pH was adjusted back to 5.2-5.5 with 0.1 N HCl. The product precipitated, isolated by centrifuge and lyophilized to give the title compound.

Example 2

General Procedure B. Acylation Using A1,B1-diBoc desB30 Human Insulin $N^{\epsilon B29}$—[N—(HOOC($CH_2$)$_{13}$CO)—N-(carboxyethyl)-$CH_2$-para-$C_6H_4$CO] desB30 human insulin Step 1: Synthesis of 4-{[(2-tert-Butoxycarbonylethyl)-(14-tert-butoxycarbonyl-tetradecanoyl)-amino]-methyl}-benzoic acid 2,5-dioxo-pyrrolidin-1-yl ester

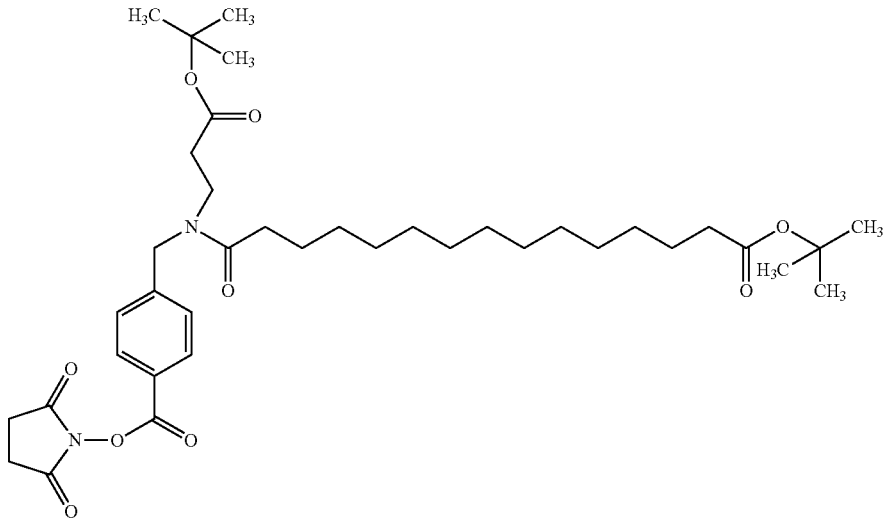

The compound was prepared similar as described in step 2 and step 3 in general procedure A using pentadecanedioic acid mono-tert-butyl ester instead.

HPLC-MS: m/z=(709 (M+Na)); $R_t$=6.03 min.

Step 2: Synthesis $N^{\epsilon B29}$ (4-{[(2-Carboxyethyl)-(14-carboxytetradecanoyl)amino]-methyl}benzoyl) desB30 human Insulin

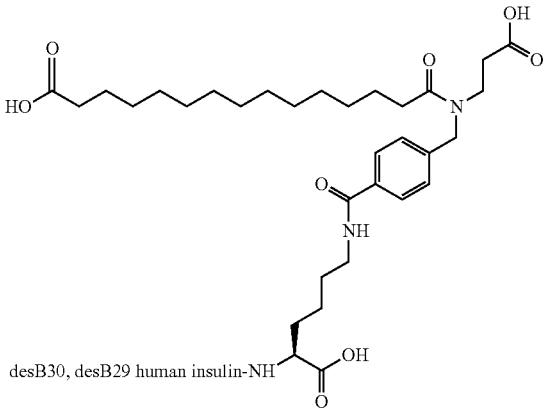

A1B1BocBoc desB30 insulin (Kurtzhals P; Havelund S; Jonassen I; Kiehr B; Larsen U D; Ribel U; Markussen J Biochemical Journal, 1995, 312, 725-731) (0.1 g, 0.017 mmol) was dissolved in DMSO (2 mL). Triethylamin (0.024 mL, 0.17 mmol) was added. 4-{[(2-tert-Butoxycarbonyl-ethyl)-(14-tert-butoxycarbonyl-tetradecanoyl)-amino]-methyl}-benzoic acid 2,5-dioxo-pyrrolidin-1-yl ester was dissolved in THF (1 mL) and added. The mixture was shaken at RT for 1 hour. The solution was cooled with an ice bath, and water (5 mL) was added. The pH was adjusted to 5.2 with 1N HCl. The mixture was allowed to precipitate for 1 hour at 5° C. The precipitate was isolated by centrifuge and treated with TFA 10 mL for 15 minutes. Poured into ice cooled diethylether (35 mL), and the crude product was isolated by centrifuge and purified on C-18 RP-HPLC 5 cm×20 cm, flow 20 ml/min using acetonitrile/water 25-45% gradient containing 0.1% TFA. Fractions containing product were collected, lyophilized. The lyophilized material was added water (7.2 mL) and pH adjusted to 8.98 with 1 N+0, 1 N NaOH. The pH was adjusted back to 5.2-5.5 with 0.1 N HCl. The product was precipitated, isolated by centrifugation and lyophilized to give the title compound.

HPLC-MS: m/z=1542 (m/4), 1234 (m/5); $R_t$=3.55 min.

Example 3

General Procedure B $N^{\epsilon B29}$—N—($HOOC(CH_2)_{16}CO$)—N(carboxyethyl)-$CH_2$-para-$C_6H_4CO$] desB30 human insulin Step 1: Synthesis of 4-{[(2-tert-Butoxycarbonyl-ethyl)-(17-tert-butoxycarbonylheptadecanoyl)amino] methyl}benzoic acid 2,5-dioxo-pyrrolidin-1-yl ester

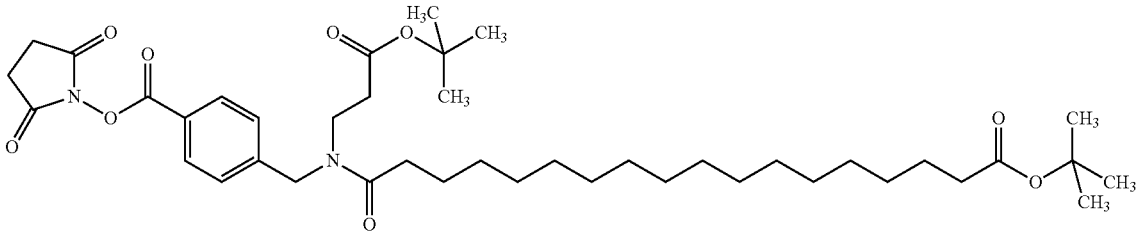

The compound was prepared similar as described in step 2 and step 3 in general procedure A using octadecanedioic acid mono-tert-butyl ester in stead.

HPLC-MS: m/z=(752 (M+Na)); $R_t$=6.62 min

Step 2: Synthesis of $N^{\epsilon B29}$-(4-{[(2-Carboxyethyl)-(17-carboxyheptadecanoyl)-amino]methyl}benzoyl) desB30 human insulin

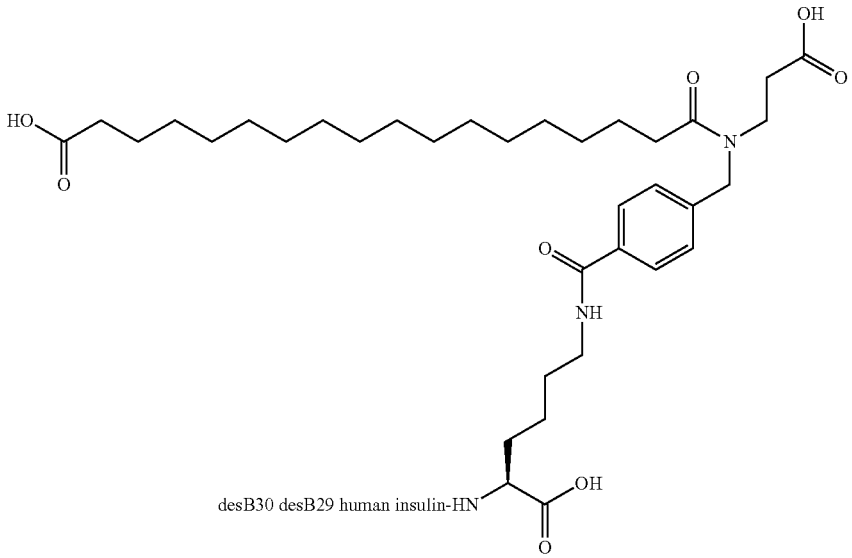

Compound from step 1 was reacted with from A1,B1-diBoc desB30 insulin as described in general procedure B. The work up was similar using a gradient 45-70% acetonitrile/water containing 0.1% TFA. The pooled fractions containing product were lyophilized and dissolved in 2.5% $NH_3$ 1 mL and diluted to 10 mL and subjected to purification on an AKTA purifier employing a reversed phase HPLC, Jupiter 5269, C4 250/20 mm, 15 μM, 300 Å. The buffer consisted of A-buffer 10 mM TRIS+15 mM $(NH_4)_2SO_4$ in 20% EtOH, pH 7.3 and a B-buffer 80% EtOH. The product was eluted with a gradient 15-60% B with 8 ml/min. The appropriate fraction were pooled and eluted on a sep pak with 70% $CH_3CN$ containing 0.1% TFA. Precipitated and lyophilized to yield the desired product.

Maldi: 6199.2

Example 4

General Procedure B $N^{\epsilon B29}$—N—(HOOC$(CH_2)_{15}$CO)—N-(carboxyethyl)-$CH_2$-para-$C_6H_4$CO] desB30 human insulin Step 1: Synthesis of heptadecanedioic acid mono-tert-butyl ester

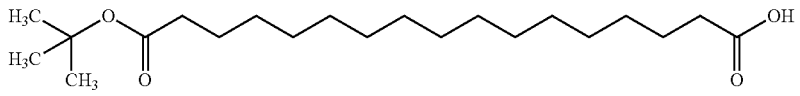

2-Methoxycarbonyl-heptadecanedioic acid 1-methyl ester

Sodium (1.11 g, 48.2 mmol) was dissolved in dry methanol (30 ml) and heated to 50° C. Dimethyl malonate (5.87 ml, 51.4 mmol) was added over 15 min. The mixture was heated to reflux and a suspension of 15-bromopentadecanoic acid (5 g, 15.6 mmol) in dry methanol (50 ml) was added over 45 min. The resulting mixture was refluxed for another 30 min. After cooling to RT, water was added and the mixture was concentrated. Water was added to the residue an made alkaline with 1 N NaOH and extracted with ether (1×50 ml). The aqueous layer was acidified with 1N HCl and extracted with ether (3×30 ml). The combined organic layers was dried ($Na_2SO_4$) and concentrated to give the title compound in 98% (5.7 g) yield.

HPLC-MS: 395 (M+Na), rt 5.38. $^1$H-NMR ($CDCl_3$): δ 1.2-1.35 (m, 22H), 1.65 (pent, 2H), 1.90 (m, 2H), 2.34 (t, 2H), 3.37 (t, 1H), 3.71 ppm (s, 6H).

Heptadecanedioic Acid:

2-Methoxycarbonyl-heptadecanedioic acid 1-methyl ester (4.63, 12.4 mmol g) was dissolved in 20% aqueous KOH (15 ml) by heating. The resulting solution was refluxed for 2.5 h. The cold reaction mixture was carefully concentrated. The residue was suspended in water (30 ml) on an ice bath and acidified with 10% aqueous HCl. The resulting slurry was refluxed for 2 h. After cooling the precipitate was isolated by filtration and dried over night in vacuo. The compound was decarboxylated by heating under stirring at 140° C. for 2 h. (the reaction should be followed, heating to 180° might be necessary). The crude product (4.0 g, 100%) was used without further purification. HPLC-MS: 323 (M+Na), $R_1$4.61. $^1$H-NMR (DMSO-$d_6$): δ 1.22 (br s, 22H) 1.47 (m, 4H), 2.18 (t, 4H).

Heptadecanedioic Acid Mono-Tert-Butyl Ester

The crude heptadecanedioic acid (0.99 g, 3.3 mmol) was dissolved in toluene (15 ml) at 115° C. N,N-dimethylformamide di-tert-butylacetale (0.79 ml, 3.3 mmol) was added dropwise over 10 min. After refluxing for 1 h more N,N-dimethylformamide di-tert-butylacetale (0.79 ml) was added over 10 min. After refluxing for another 1 h, a last eq of N,N-dimethylformamide di-tert-butylacetale (0.79 ml) was added over 10 min. Reflux was continued for 1 h. On cooling to RT a precipitate appeared, this was filtered off (diacid). The mother liqueour was extracted with water (25 ml) and DCM (25 ml). The organic layer was dried and concentrated. The residue was purified by flash chromatography using DCM/MeOH 15:1 as eluent. Heptadecanedioic acid mono-tert-butyl ester was isolated in 33% yield (0.330 g). HPLC-MS: 379 (M+Na), rt 6.11. $^1$H-NMR (DMSO-$d_6$): δ 1.22 (br s, 22H), 1.39 (s, 9H), 1.47 (m, 4H), 2.16 (t, 2H), 2.19 ppm (t, 2H).

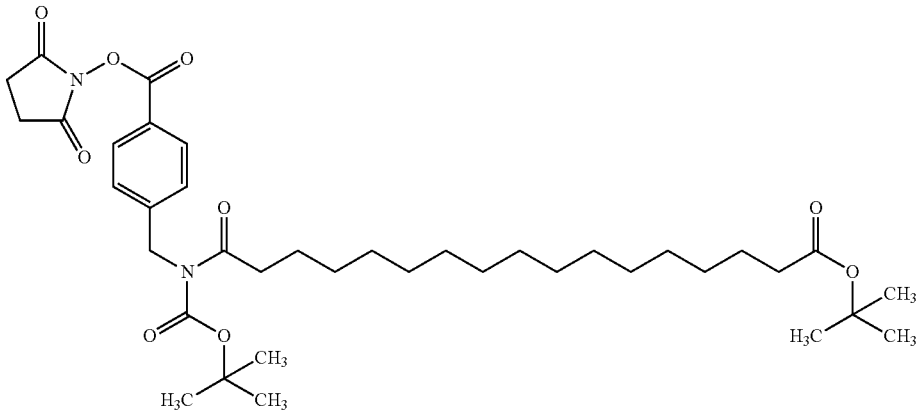

Step 2: Synthesis of 4-{[(2-tert-Butoxycarbonyl-ethyl)-(16-tert-butoxycarbonylhexadecanoyl)amino]methyl}benzoic acid 2,5-dioxopyrrolidin-1-yl ester The compound was prepared similar as described in step 2 and step 3 in general procedure A using heptadecanedioic acid mono-tert-butyl ester in stead.

Step 3: Synthesis of $N^{\epsilon B29}$-(4-{[(2-Carboxyethyl)-(16-carboxyhexadecanoyl)amino]-methyl}benzoyl) desB30 human insulin

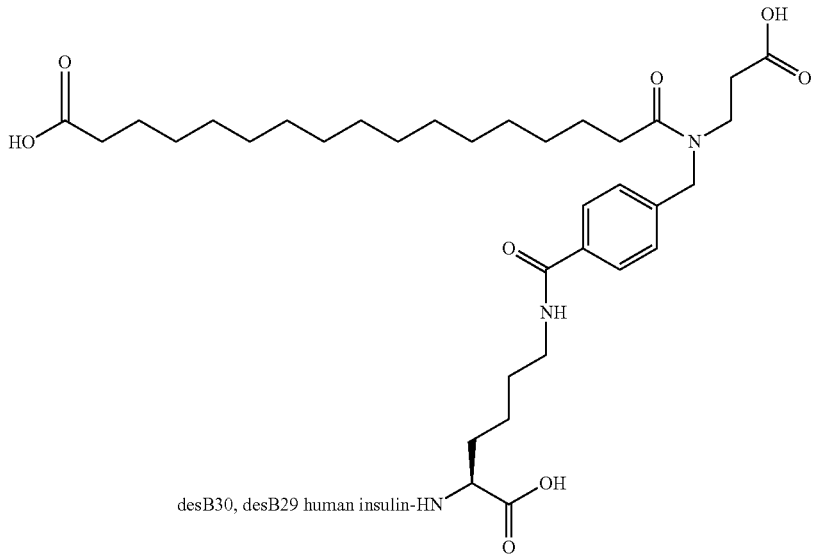

4-{[(2-tert-Butoxycarbonylethyl)-(16-tert-butoxycarbonylhexadecanoyl)-amino]methyl}benzoic acid 2,5-dioxopyrrolidin-1-yl ester was reacted with A1,B1-diBoc desB30 insulin as described in general procedure B. The work up was similar using a gradient 28-48% acetonitrile/water containing 0.1% TFA.

HPLC-MS: m/z=1549 (m/4), 1239 (m/5); $R_t$=3.53 min.

Example 5

General Procedure B $N^{\epsilon B29}$-[(5-{[(2-Carboxyethyl)-(15-carboxypentadecanoyl)amino]methyl}furan-2-carbonyl)desB30 human insulin Step 1: 5-[(2-tert-Butoxycarbonylethylamino) methyl]furan-2-carboxylic acid

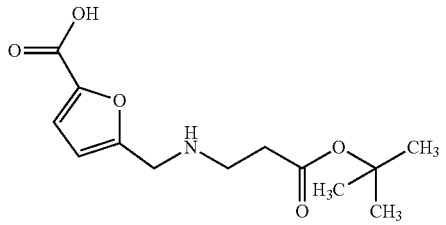

This compound was synthesized using a similar procedure as described in step 1 in general procedure A using 5-formylfuran-2-carboxylic acid instead of 4-carboxybenzaldehyd $^1$H NMR ($CDCl_3$): δ 7.12 (d, 1H), 6.65 (d, 1H), 4.37 (s, 2H), 3.35 (t, 2H), 2.80 (t, 2H), 1.45 (s, 9H).

Step 2: 5-{[(2-tert-Butoxycarbonylethyl)-(15-tert-butoxycarbonylpentadecanoyl)amino]-methyl}furan-2-carboxylic acid

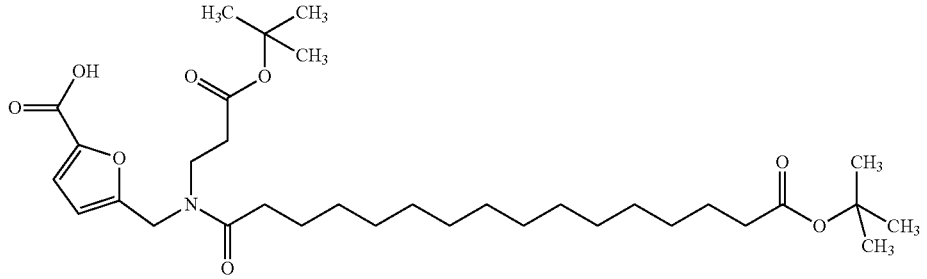

This compound was synthesized using a similar procedure as described in step 1 in general procedure A using 5-[(2-tert-Butoxycarbonylethylamino)methyl]furan-2-carboxylic acid instead of 4-[(2-tert-Butoxycarbonylethylamino) methyl]benzoic acid.

$^1$H NMR (DMSO-$d_6$): δ 7.15 (dd, 1H), 6.45 (dd, 1H), 4.57 (d, 2H), 2.43-2.10 (m, 6H), 1.60-1.20 (m, 42H).

HPLC-MS: m/z=(616 (M+Na), 538 (lose of tert-butyl, 482 (lose of two tert-butyl), $R_t$=6.17 min.

Step 3: 5-{[(2-tert-Butoxycarbonylethyl)-(15-tert-butoxycarbonylpentadecanoyl)-amino]methyl}-furan-2-carboxylic acid 2,5-dioxo-pyrrolidin-1-yl ester

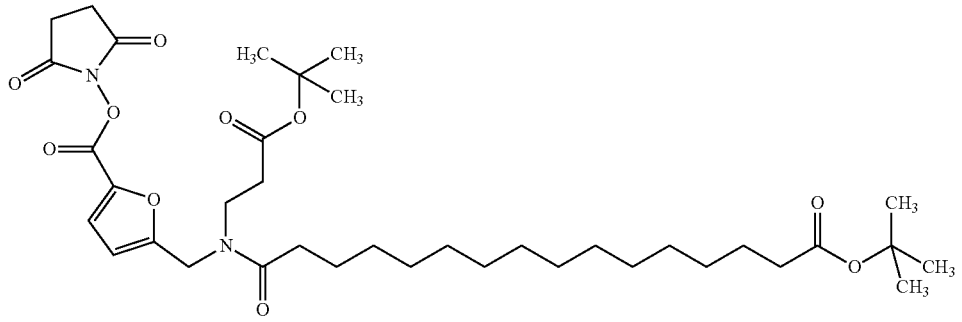

This compound was synthesized using a similar procedure as described in step 3 in general procedure A HPLC-MS: m/z=(713 (M+Na), $R_t$=6.4 min.

Step 4 $N^{\epsilon B29}$-[(5-{[(2-Carboxyethyl)-(15-carboxy-pentadecanoyl)amino]methyl}furan-2-carbonyl) desB30 human insulin

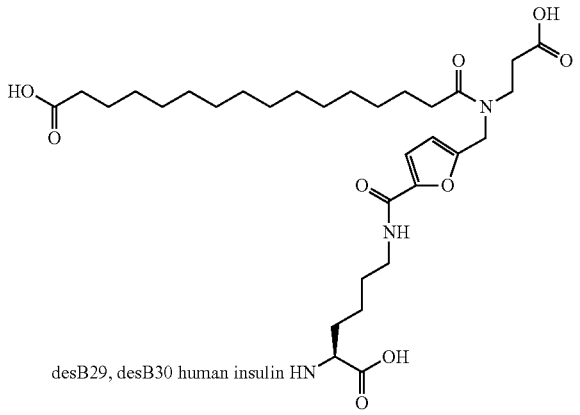

5-{[(2-tert-Butoxycarbonylethyl)-(15-tert-butoxycarbonylpentadecanoyl)amino]methyl}furan-2-carboxylic acid 2,5-dioxo-pyrrolidin-1-yl ester was reacted with A1,B1-diBoc desB30 insulin as described in general procedure B.

The work up was similar using a gradient 25-45% acetonitrile/water containing 0.1% TFA. The pooled fractions containing product was lyophilized and dissolved in 2.5% $NH_3$ 1 mL and diluted to 38 mL and subjected to purification on an AKTA purifier employing a reversed phase HPLC, Jupiter 5269, C4 250/20 mm, 15 μM, 300 Å. The buffer consisted of A-buffer 10 mM TRIS+15 mM $(NH_4)_2SO_4$ in 20% EtOH, pH7.3 and a B-buffer 80% EtOH. The product was eluted with a gradient 15-60% B with 8 ml/min. The appropriate fractions were pooled and eluted on a sep pak with 3 mL 70% $CH_3CN$ containing 0.1% TFA. Precipitated and lyophilized to yield the desired product.

MS. m/z=6169.

Example 6

General Procedure B $N^{\epsilon B29}$—[N—(HOOC$(CH_2)_{14}$CO—N-(carboxethyl)-$CH_2$-meta $C_6H_4$CO] desB30 human insulin Step 1: 3-[(2-tert-Butoxycarbonylethylamino) methyl]benzoic acid

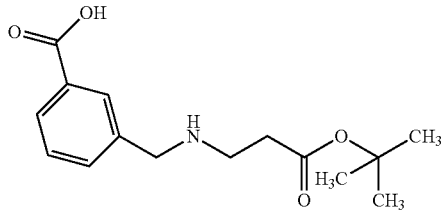

This compound was synthesized using a similar procedure as described in step 1 in general procedure A using 3-carboxybenzaldehyde instead of 4-carboxybenzaldehyde HPLC-MS (Method fast grad): m/z=(302, M+Na); $R_t$=1.1 min.

Step 2: 3-{[(2-tert-Butoxycarbonylethyl)-(15-tert-butoxycarbonylpentadecanoyl)amino] methyl}benzoic acid

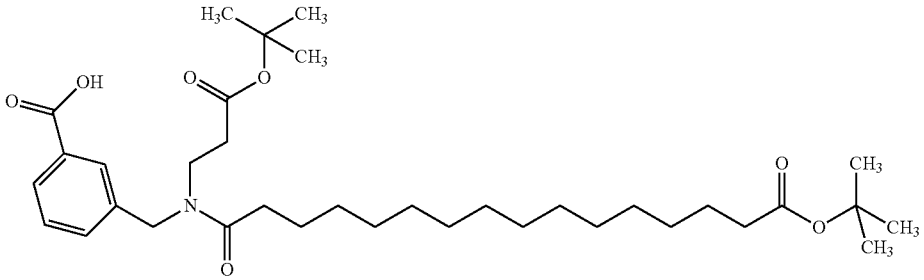

This compound was synthesized using a similar procedure as described in step 1 in general procedure A using 3-[(2-tert-Butoxycarbonylethylamino)methyl]benzoic acid instead of 4-[(2-tert-Butoxycarbonylethylamino)methyl] benzoic acid.

HPLC-MS (Method fast grad): m/z=(603, M+1); $R_t$=3.09 min.

Step 3: 2-{[(2-tert-Butoxycarbonyl-ethyl)-(15-tert-butoxycarbonyl-pentadecanoyl)-amino]-methyl}-benzoic acid 2,5-dioxo-pyrrolidin-1-yl ester

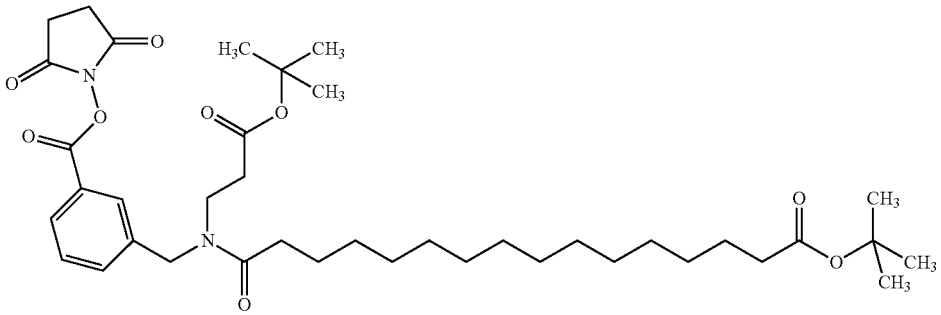

This compound was synthesized using a similar procedure as described in step 3 in general procedure A HPLC-MS (Method fast grad): m/z=723, (M+Na); $R_t$=3.15 min.

Step 4: Synthesis of $N^{\epsilon B29}$-(3-{[(2-Carboxyethyl)-(15-carboxypentadecanoyl)amino]-methyl}benzoyl) desB30 human insulin

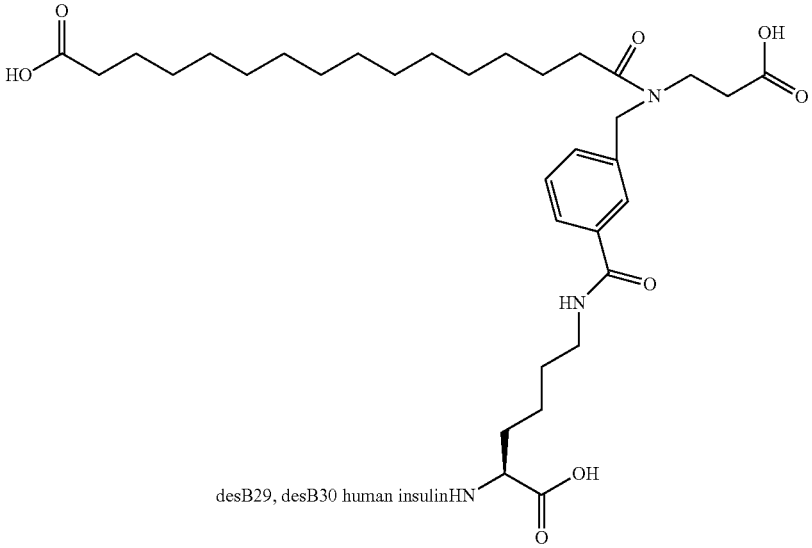

3-{[(2-tert-Butoxycarbonyl-ethyl)-(15-tert-butoxycarbonyl-pentadecanoyl)-amino]-methyl}-benzoic acid 2,5-dioxo-pyrrolidin-1-yl ester was reacted with A1B1BocBoc desB30 insulin as described in general procedure B. The work up was similar using a gradient 25-45% acetonitrile/water containing 0.1% TFA. The pooled fractions containing product were precipitated and lyophilized.

HPLC-MS: m/z=1236 (m/5), 1030 (m/6); $R_t$=3.7 min.

Example 7

General Procedure B $N^{\epsilon B29}$—[N—HOOC$(CH_2)_{14}$CO)—N-(carboxethyl)-$CH_2$-ortho $C_6H_4$CO] desB30 human insulin Step 1: 2-[(2-tert-Butoxycarbonylethylamino) methyl]benzoic acid

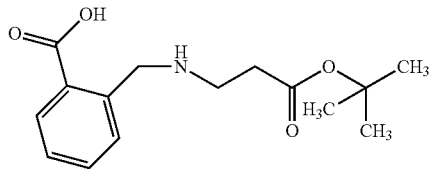

This compound was synthesized using a similar procedure as described in step 1 in general procedure A using 2-carboxybenzaldehyd instead of 4-carboxybenzaldehyd HPLC-MS (Method fast grad): m/z=280, (M+1); $R_t$=1.13 min.

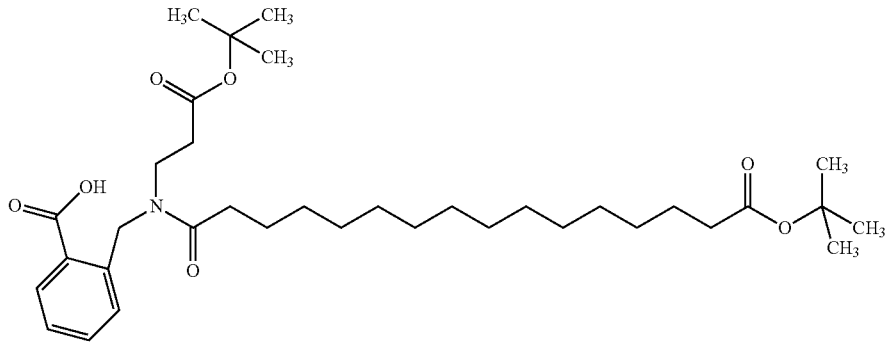

Step 2: 3-{[(2-tert-Butoxycarbonylethyl)-(15-tert-butoxycarbonylpentadecanoyl)amino] methyl}benzoic acid This compound was synthesized using a similar procedure as described in step 1 in general procedure A using 2-[(2-tert-Butoxycarbonylethylamino)methyl]benzoic acid instead of 4-[(2-tert-Butoxycarbonylethylamino)methyl] benzoic acid.

HPLC-MS (Method fast grad): m/z=604; $R_t$=3.09 min.

Step 3: 3-{[(2-tert-Butoxycarbonyl-ethyl)-(15-tert-butoxycarbonyl-pentadecanoyl)-amino]-methyl}-benzoic acid 2,5-dioxo-pyrrolidin-1-yl ester

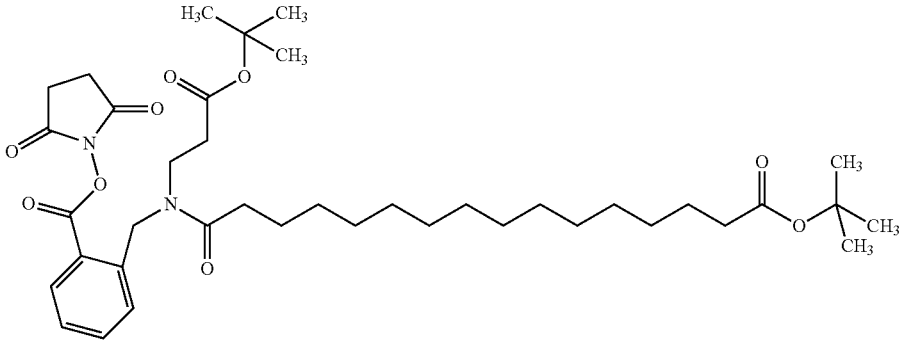

This compound was synthesized using a similar procedure as described in step 3 in general procedure A HPLC-MS (Method fast grad): m/z=(723, M+Na); $R_t$=3.15 min.

Step 4: Synthesis of $N^{\epsilon B29}$ (3-{[(2-Carboxyethyl)-(15-carboxypentadecanoyl)amino]-methyl}benzoyl) desB30 human insulin HPLC-MS (Method fast grad): m/z=(302, M+Na); $R_t$=1.1 min.

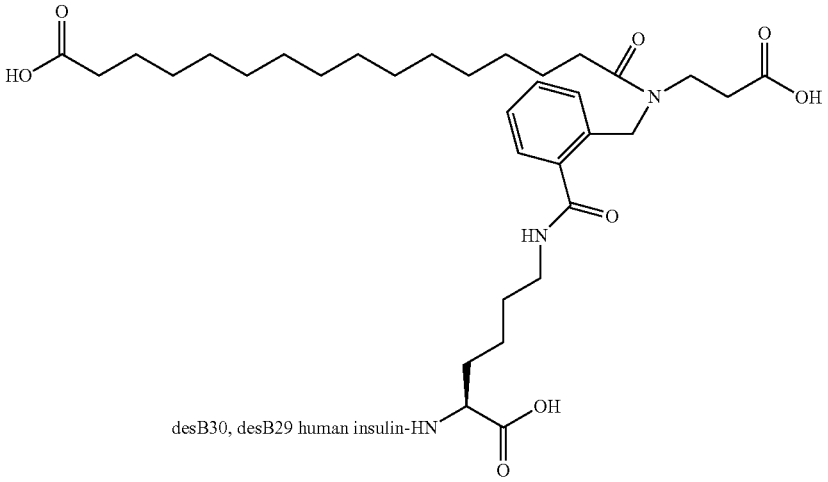

2-{[(2-tert-Butoxycarbonyl-ethyl)-(15-tert-butoxycarbonyl-pentadecanoyl)-amino]-methyl}-benzoic acid 2,5-dioxo-pyrrolidin-1-yl ester was reacted with A1,B1-diBoc des (B30) insulin as described in general procedure B. The work up was similar using a gradient 28-48% acetonitrile/water containing 0.1% TFA. The pooled fractions containing product was precipitated and lyophilized The pooled fractions containing product was lyophilized and dissolved in 2.5% $NH_3$ 1 mL and diluted to 38 mL and subjected to purification on an ÄKTA purifier employing a reversed phase HPLC, Jupiter 5269, C4 250/20 mm, 15 μM, 300 Å. The buffer consisted of A-buffer 10 mM TRIS+15 mM $(NH_4)_2SO_4$ in 10% Acetonitrile, pH7.3 and a B-buffer 70% Acetnotrile. The product was eluted with a gradient 27-33% B with 6 ml/min over 90 minutes The appropriate fractions were pooled and eluted on a sep pack with 3 mL 70% $CH_3CN$ containing 0.1% TFA, precipitated and lyophilized to yield the desired product.

Example 8

$N^{\epsilon B29}$—[N—(HOOC($CH_2$)$_{14}$CO)—N-(carboxyethyl)-para-$C_6H_4$CO] desB30 human insulin Step 1: 4-(15-tert-Butoxycarbonylpentadecanoylamino)benzoic acid methyl ester

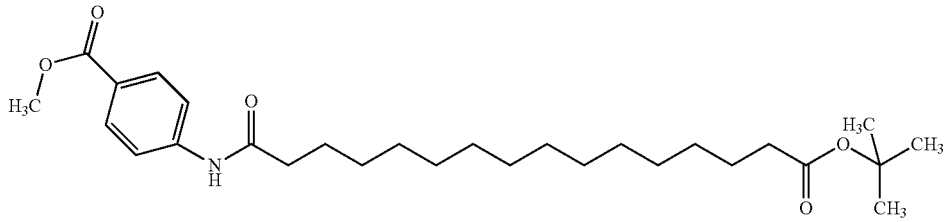

Hexadecanedioic acid mono-tert-butyl ester (0.4 g, 1.17 mmol) was dissolved in NMP (6 mL). N-Ethyl-N-(3-dimethylaminopropyl)-carbodiimide hydrochloride (0.223 g, 0.1.17 mmol) and 1-hydroxy-7-azabenzotriazole (0.159 g, 1.17 mmol) was added and the mixture was stirred at 50° C. for 1 hour and then allowed to cool to room temperature. Diisopropylethylamin (0.6 mL, 3.5 mmol) was added followed by methyl 4-aminobenzoate (0.353 g, 2.34 mmol). The mixture was stirred overnight under nitrogen at room temperature. The mixture was poured into saturated aqueous NaCl (50 mL), washed with diethylether (3×100 mL between ethyl acetate. The organic phases were collected, dried ($Na_2SO_4$) and solvent removed in vacuo. The crude material was purified on silica using ethyl acetate/heptane (50:50), to give pure 4-(15-tert-Butoxycarbonylpentadecanoylamino) benzoic acid methyl ester (235 mg, 42%)

$^1$H-NMR ($CDCl_3$) δ 8.00 (d, 2H), 7.61 (d, 2H), 7.32 (br s, 1H), 3.90 (s, 3H), 2.37 (t, 2H), 2.20 (t, 2H), 1.70 (m, 2H), 1.43 (s, 9H), 1.40-1.20 (m, 20H)

Step 2: 4-[tert-Butoxycarbonylmethyl-(15-tert-butoxycarbonylpentadecanoyl)amino]benzoic acid 4-(15-tert-Butoxycarbonylpentadecanoylamino)benzoic acid methyl ester (235 mg, 0.495 mmol) was evaporated twice from dry pyridine and once from dry acetonitrile, dissolved in dry DMF (4 mL) under nitrogen. 60% NaH (14 mg, 0.594 mmol) was added and the mixture was stirred for 20 minutes at room temperature under nitrogen. tert-Butyl bromoacetate (0.11 mL, 0.742 mmol) was added and the mixture was stirred for 1 hour, the reaction was quenched with ice and separated between water (50 mL) and diethylether (75 mL). The organic phase was dried ($Na_2SO_4$) and solvent remove in vacuo. The crude material was dissolved in ethanol (4 mL). NaOH (5 N, 0.15 mL) was added and the mixture was stirred for 1 hour. pH was adjusted to pH=5 with acetic acid and the mixture was separated between water and ethyl acetate. The organic phase was dried ($Na_2SO_4$) and solvent removed in vacuo to give the crude product which was purified on RP-HPLC, C-18 with acetonitrile/water gradient (75-95%) containing 0.1% TFA. To give pure 4-[tert-Butoxycarbonylmethyl-(15-tert-butoxycarbonylpentadecanoyl)amino]benzoic acid) (53 mg, 19%)

HPLC-MS (fast grad): m/z=598 (M+Na), Rt=3.02 min.

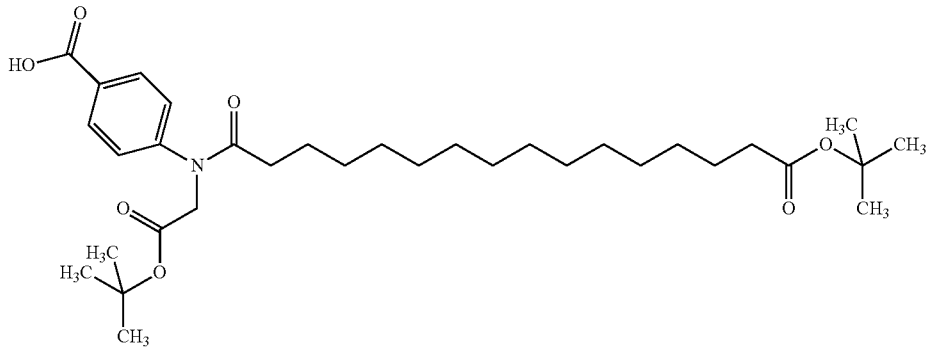

Step 3: 4-[tert-Butoxycarbonylmethyl(15-tert-butoxycarbonylpentadecanoyl)amino]benzoic acid 2,5-dioxopyrrolidin-1-yl ester
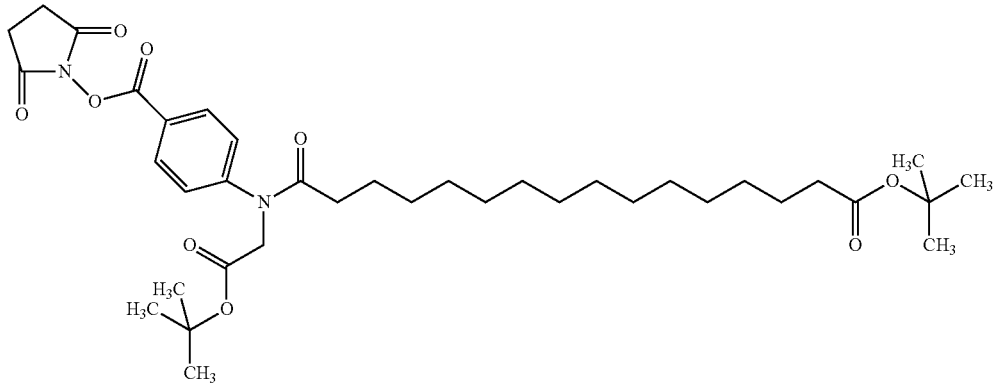
This compound was synthesized from 4-[tert-Butoxycarbonylmethyl-(15-tert-butoxycarbonylpentadecanoyl)amino] benzoic acid) using a similar procedure as described in step 3 in general procedure A.
$^1$H H-NMR ($CDCl_3$) δ 8.19 (d, 2H), 7.49 (d, 2H), 4.27 (s, 2H), 2.94 (s, 4H), 2.17 (m, 4H), 1.57 (m, 4H), 1.46 (s, 9H), 1.44 (s, 9H), 1.30-1.15 (m, 20H).
Step 4
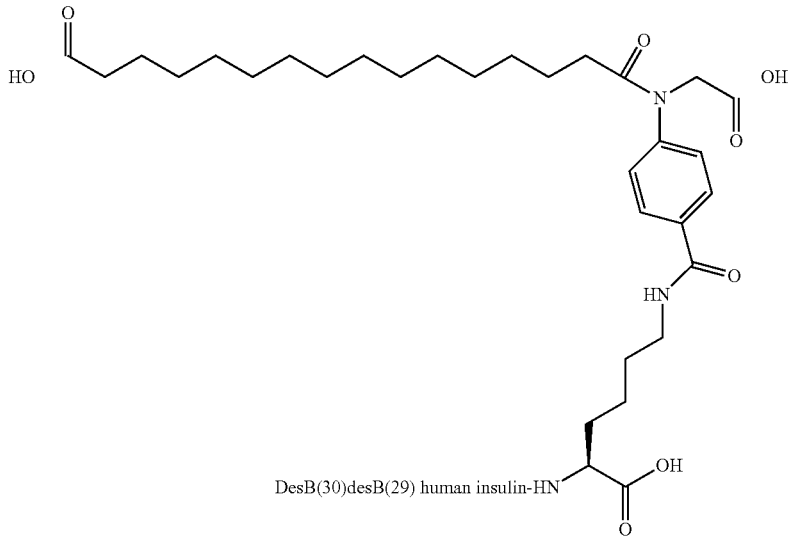

4-[tert-Butoxycarbonylmethyl(15-tert-butoxycarbonyl-pentadecanoyl)amino]benzoic acid 2,5-dioxopyrrolidin-1-yl ester was reacted with A1,B1-diBoc desB30 insulin as described in general procedure B.

HPLC-MS: m/z=1539 (m/4).

Example 9

$N^{\epsilon B29}$-(3-Carboxy-5-hexadecandioylaminobenzoyl) des(B30)insulin

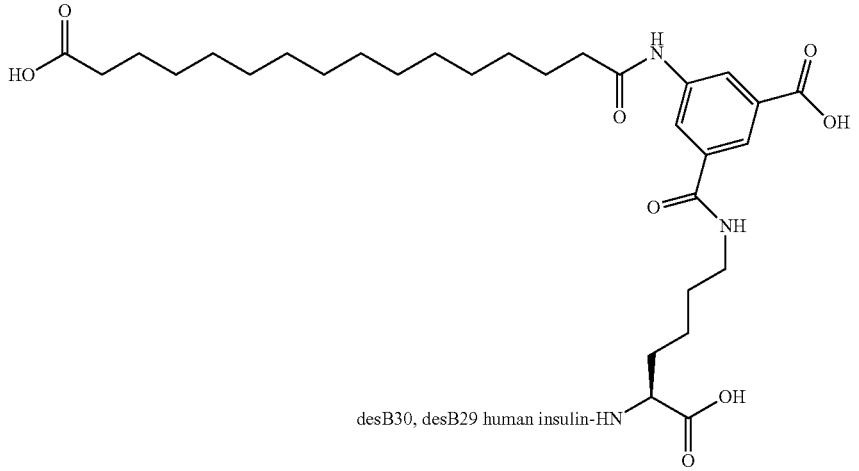

5-Nitro-isophthalic acid mono t-Butyl ester

To a suspension of 5-nitro-isophthalic acid (5.0 g, 23.7 mmol) in dry toluene (100 ml) at 110° C. was added dimethylformamid di-t-butylacetale (3.4 ml, 71 mmol) drop wise over 60 min. Heating was continued for 45 min and the reaction mixture was left at Rt over night. The precipitated starting material was removed by filtration. The filtrate was concentrated to give a yellow oil (7.88 g). This was purified by flash chromatography using EtOAc/Hept 1:2 and EtOAc/Hept 1:2+5% AcOH in two portions to give the title compound in 38% yield (2.38 g)

$^1$H-NMR ($CDCl_3$): δ 1.65 (s, 9H), 8.98 (s, 1H), 9.01 (s, 1H), 9.06 ppm (s, 1H).

5-Amino-isophthalic acid mono t-Butyl ester

5-Nitro-isophthalic acid mono t-Butyl ester (2.38 g, 8.9 mmol) was dissolved in EtOAc (50 ml). 10% Palladium on activated charcoal was added and the mixture was hydrogenated at 1 atm and room temperature. After 24 h, the mixture was filtered through a glas microfiber filter and the filtrate was concentrated to give the title compound as white crystals in 98% yield (2.07 g).

$^1$H-NMR (DMSO, d6): δ 1.54 (s, 9H), 5.59 (br, 2H, $NH_2$); 7.33 (s, 1H), 7.37 (s, 1H), 7.60 ppm (s, 1H).

5-(15-tert-Butoxycarbonyl-pentadecanoylamino)-isophthalic acid mono-tert-butyl ester To a solution of hexadecandioic acid mono t-butyl ester (100 mg, 0.29 mmol) in dry DCM (2 ml), HOAt (44 mg, 0.29 mmol) and DCC (72 mg, 32 mmol) was added. The mixture was stirred at 50° C. for 1 h. The oil bath was removed. 5-Amino-isophthalic acid mono t-butyl ester (69 mg, 0.29) and DIPEA (0.07 ml, 0.32 mmol) was added. The mixture was stirred at RT over night under nitrogen. The yellow suspension was filtered and the filtrate was concentrated. The residue was redissolved in EtOAc and extracted with 0.1N HCl (2×), brine (1×), dried ($Na_2SO_4$) and concentrated to give a white solid, which was purified twice by flash chromatography using EtOAc/Hept 1:2+5% AcOH. The title compound was obtained in 86% yield (0.140 g) as an oil containing an impurity.

1H NMR (400 MHz) δ :1.25 (s, 22H) 1.42-1.45 (m, 9H) 1.53-1.65 (m, 11H) 1.68-1.79 (m, 2H) 2.20 (s, 2H) 2.41 (s, 2H) 7.58 (brs, 1H) 8.35 (s, 1H) 8.39 (s, 2H)

5-(15-tert-Butoxycarbonyl-pentadecanoylamino)-isophthalic acid 1-tert-butyl ester 3-(2,5-dioxo-pyrrolidin-1-yl) ester 5-(15-tert-Butoxycarbonyl-pentadecanoylamino)-isophthalic acid mono-tert-butyl ester (140 mg, 0.25 mmol) was dissolved in dry THF (3.5 ml). TSTU (95 mg, 0.30 mmol) and DIPEA (70 ul, 0.30 mmol) were added. The mixture was stirred at RT under nitrogen over the week-end. The reaction mixture was almost dry. EtOAc was added and the precipitate was removed by filtration. The filtrate was extracted with 0.1 N HCl (2×), brine (1×), dried ($Na_2SO_4$) and concentrated to give the title compound as a syrup containing a trace of an impurity in a quantitative yield (0.165 mg).

1H NMR (400 MHz) δ: ppm 1.20-1.35 (m, 22H) 1.44 (s, 9H) 1.52-1.64 (m, 11H) 1.68-1.79 (m, 2H) 2.12-2.24 (m, 2H) 2.34-2.42 (m, 2H) 2.91 (s, 4H) 7.39 (s, 1H, NH) 8.34 (s, 1H) 8.43 (s, 1H) 8.54 (s, 1H)

$N^{\epsilon B29}$-(3-Carboxy-5-hexadecandioylamino-benzoyl) desB30 human insulin A1N, B1N-diBoc desB30 human insulin (100 mg, 0.017 mmol) was acylated with 5-(15-tert-Butoxycarbonyl-pentadecanoylamino)-isophthalic acid 1-tert-butyl ester 3-(2,5-dioxo-pyrrolidin-1-yl) ester (15 mg, 0.022 mmol) as described in general procedure B. The product was purified by preparative HPLC and hydrolysed as described in general procedure B to give the title compound, 9 mg.

MALDI-MS (SA): 6130.8. anal. HPLC (neut, Alrg), 96.5% purity, rt 6.11 min. (Column: C4 5μ 150×4.60 mm "phenomenex, Jupiter" Buffer A: 10 mM Tris, 15 mM $(NH_4)_2SO_4$, pH 7.3, 20% $CH_3CN$ in MQ water. Buffer B: 80% $CH_3CN$, 20% MQ-water, Flow: 1,5 ml/min; Gradient: 0 min 10% B→20 min 50% B→21 min 50% B→23 min 10% B→30 min 10% B) anal. HPLC (acidic), 100% purity, rt 12.24 min (Column: C4 5μ 150×4.60 mm "phenomenex, Jupiter" Buffer A: 0.1% TFA, 10% $CH_3CN$, 89.9% MQ-water Buffer B: 0.1% TFA, 80% $CH_3CN$, 19.9% MQ-water, Flow: 1.5 ml/min; Gradient: 0 min 20% B→17 min 90% B→21 min 90% B→23 min 20% B→30 min 20% B.

Example 10

$N^{\epsilon B29}$-(3-Carboxy-5-octadecandioylaminobenzoyl) des(B30) human insulin

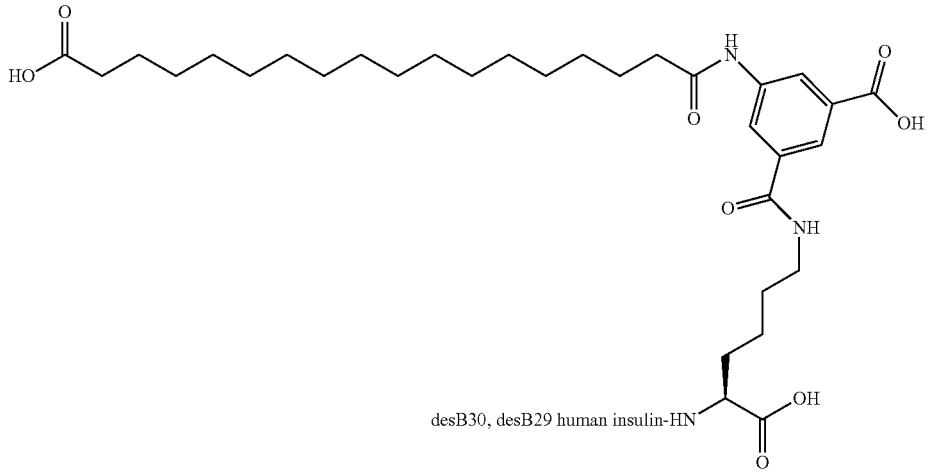

The title compound was prepared as described in example 9 using octadecanedioc acid monotertbutyl ester in stead of hexadecandioic acid. MALDI-MS (SA): 6160.9. anal. HPLC (neut), 96.0% purity, rt 8.93 min. (Column: C4 5μ 150×4.60 mm "phenomenex, Jupiter" Buffer A: 10 mM Tris, 15 mM $(NH_4)_2SO_4$, pH 7.3, 20% $CH_3CN$ in MQ water. Buffer B: 80% $CH_3CN$, 20% MQ-water, Flow: 1.5 ml/min; Gradient: 0 min 10% B→20 min 50% B→21 min 50% B→23 min 10% B→30 min 10% B). anal. HPLC (acidic), 100% purity, rt 13.62 min (Column: C4 5μ 150×4.60 mm "phenomenex, Jupiter" Buffer A: 0.1% TFA, 10% $CH_3CN$, 89.9% MQ-water Buffer B: 0.1% TFA, 80% $CH_3CN$, 19.9% MQ-water, Flow: 1.5 ml/min; Gradient: 0 min 20% B→17 min 90% B→21 min 90% B→23 min 20% B→30 min 20% B).

Example 11

Synthesis of $N^{\epsilon B29}$-ω-carboxypentadecanoyl-γ-L-glutamyl 4-aminomethyl-benzoyl) desB30 human insulin

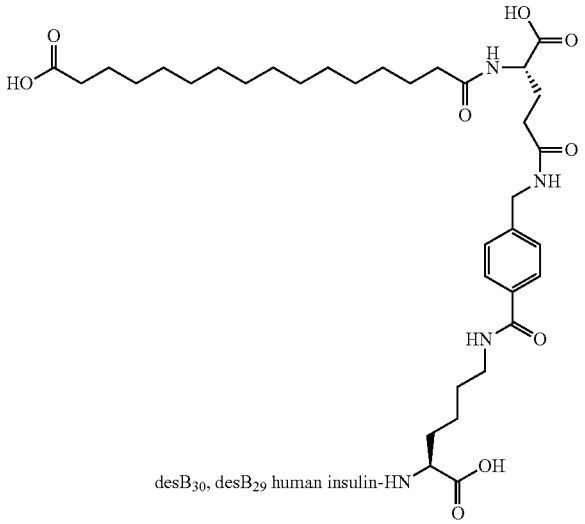

Mono-tert-butyl hexadecandioate

Hexadecadioic acid (40.0 g, 140 mmol) was suspended in toluene (250 ml) and the mixture was heated to reflux. N,N-dimethylformamide di-tert-butyl acetal (76.3 g, 375 mmol) was added drop-wise over 4 hours. The mixture was refluxed overnight. The solvent was removed in vacuo at 50° C., and the crude material was suspended in DCM/AcOEt (500 ml, 1:1) and stirred for 15 min. The solids were collected by filtration and triturated with DCM (200 ml). The filtrate was evaporated in vacuo to give crude mono-tert-butyl hexadecandioate, 30 grams. This material was suspended in DCM (50 ml), cooled with ice for 10 mins, and filtered. The solvent was removed in vacuo to leave 25 gram crude mono-tert-butyl hexadecandioate, which was recrystallized from heptane (200 ml) to give mono-tert-butyl hexadecandioate, 15.9 g (33%). Alternatively to recrystallization, the mono-ester can be purified by silica chromatography in AcOEt/heptane.

$^1$H-NMR ($CDCl_3$) δ: 2.35 (t, 2H), 2.20 (t, 2H), 1.65-1.55 (m, 4H), 1.44 (s, 9H), 1.34-1.20 (m, 20H).

Succinimidyl tert-butyl hexadecandioate

The mono tert-butyl ester (2 g, 5.8 mmol) was dissolved in THF (20 ml) and treated with TSTU (2.1 g, 7.0 mmol) and DIEA (1.2 ml, 7.0 mmol) and stirred overnight. The mixture was filtered, and the filtrate was evaporated in vacuo. The residue was dissolved in AcOEt and washed twice with cold 0.1 M HCl and water. Drying over $MgSO_4$ and evaporation in vacuo gave succinimidyl tert-butyl hexadecandioate, 2.02 g (79%).

$^1$H-NMR ($CDCl_3$) δ: 2.84 (s, 4H), 2.60 (t, 2H), 2.20 (t, 2H), 1.74 (p, 2H), 1.56 (m, 2H), 1.44 (s, 9H), 1.40 (m, 2H), 1.30-1.20 (m, 18H).

Tert-butyl hexadecandioyl-L-Glu-OtBu

Succinimidyl tert-butyl hexadecandioate (1 g, 2.27 mmol) was dissolved DMF (15 ml) and treated with L-Glu-OtBu (0.51 g, 2.5 mmol) and DIEA (0.58 ml, 3.41 mmol) and the mixture was stirred overnight. The solvent was evaporated in vacuo, and the crude product was dissolved in AcOEt, and washed twice with 0.2M HCl, with water and brine. Drying over $MgSO_4$ and evaporation in vacuo gave tert-butyl hexadecandioyl-L-Glu-OtBu, 1.2 g (100%).

$^1$H-NMR ($CDCl_3$) δ: 6.25 (d, 1H), 4.53 (m, 1H), 2.42 (m, 2H), 2.21 (m, 4H), 1.92 (m, 1H), 1.58 (m, 4H), 1.47 (s, 9H), 1.43 (s, 9H), 1.43-1.22 (m, 18H).

Tert-butyl hexadecandioyl-L-Glu(OSu)-OtBu

Tert-butyl hexadecandioyl-L-Glu-OtBu (1.2 g, 2.27 mmol) was dissolved in THF (15 ml) and treated with TSTU (0.82 g, 2.72 mmol) and DIEA (0.47 ml, 2.72 mmol) and stirred overnight. The mixture was filtered, and the filtrate was evaporated in vacuo. The residue was dissolved in AcOEt and washed twice with cold 0.1 M HCl and water. Drying over $MgSO_4$ and evaporation in vacuo gave tert-butyl hexadecandioyl-L-Glu(OSu)-OtBu, 1.30 g (92%).

$^1$H-NMR ($CDCl_3$) δ: 6.17 (d, 1H), 4.60 (m, 1H), 2.84 (s, 4H), 2.72 (m, 1H), 2.64 (m, 1H), 2.32 (m, 1H), 2.20 (m, 4H), 2.08 (m, 1H), 1.6 (m, 4H), 1.47 (s, 9H), 1.43 (s, 9H), 1.33-1.21 (m, 20H).

Tert-butyl hexadecandioyl-L-Glu ($NHCH_2PhCOOH$)-OtBu

Tert-butyl hexadecandioyl-L-Glu(OSu)-OtBu (100 mg, 0.16 mmol) i DMF (1 ml) was treated with 4-aminomethylbenzoic acid (27 mg, 0.18 mmol) and DIEA (41 μL, 0.24 mmol) and the mixture was stirred overnight. The solvent was evaporated and the residue was dissolved in AcOEt. The organic phase was washed with 2×0.2M HCl, water and brine.

Drying over $MgSO_4$ and evaporation in vacuo gave tert-butyl hexadecandioyl-L-Glu($NHCH_2PhCOOH$)-OtBu, 92 mg (87%).

$^1$H-NMR ($CDCl_3$) δ: 7.85 (d, 2H, J=8 Hz), 7.30 (d, 2H, J=8 Hz), 7.16 (t, 1H), 7.43 (d, 1H), 4.50, (m, 3H), 2.39 (t, 2H), 2.29 (m, 1H), 2.25 (t, 2H), 2.18 (t, 2H), 1.89 (m, 1H), 1.59 (m, 6H), 1.47 (s, 9H), 1.43 (s, 9H), 1.25 (m, 20H).

Tert-butyl hexadecandioyl-L-Glu ($NHCH_2PhCOOSu$)-OtBu tert-butyl hexadecandioyl-L-Glu($NHCH_2PhCOOH$)-OtBu (92 mg, 0.14 mmol) was dissolved in THF (1 ml) and treated with TSTU (50 mg, 0.17 mmol) and DIEA (29 μl, 0.177 mmol) and stirred overnight. The mixture was filtered, and the filtrate was evaporated in vacuo. The residue was dissolved in AcOEt and washed twice with cold 0.1 M HCl and water. Drying over $MgSO_4$ and evaporation in vacuo gave tert-butyl hexadecandioyl-L-Glu($NHCH_2PhCOOSu$)-OtBu, 95 mg (90%).

$^1$H-NMR ($CDCl_3$) δ: 8.07 (d, 2H, J=8 Hz), 7.45 (d, 2H, J=8 Hz), 7.37 (t, 1H), 6.38 (d, 1H), 4.53, (m, 2H), 4.40 (m, 1H), 2.89 (s, 4H), 2.32 (t, 2H), 2.20 (m, 6H), 1.86 (m, 2H), 1.59 (m, 6H), 1.46 (s, 9H), 1.44 (s, 9H), 1.25 (m, 20H).

$N^{\epsilon B29}$-ω-carboxypentadecanoyl-γ-L-glutannyl 4-aminomethyl-benzoyl) desB30 human insulin Des(B30) human insulin (500 mg, 0.090 mmol) was dissolved in 100 mM $Na_2CO_3$ (6.5 ml, pH 10.2) at room temperature. Tert-butyl hexadecandioyl-L-Glu ($NHCH_2PhCOOSu$)-OtBu (80 mg, 105 mmol) was dissolved in acetonitrile (6.5 ml) and added to the insulin solution. After 30 mins, 0 2 M methylamine (0.5 ml) was added. pH was adjusted by HCl to 5.5 by use of 1 M HCl, and the isoelectric precipitate was collected by centrifugation and dried in vacuo. The coupling yield was 84% (RP-HPLC, C4 column; Buffer A: 10% MeCN in 0.1% TFA-water, Buffer B: 80% MeCN in 0.1% TFA-water; gradient 20% to 90% B in 16 minutes). The protected product was dissolved in 95% TFA (15 ml), left 30 mins and evaporated in vacuo. The crude product was dissolved in water and lyophilized.

$N^{\epsilon B29}$-hexadecandioyl-gamma-Glu-(4-aminomethyl-benzoyl) desB30 insulin was purified by RP-HPLC on C4-column, buffer A: 20% EtOH+0.1% TFA, buffer B: 80% EtOH+0.1% TFA; gradient 15-60% B, followed by HPLC on C4-column, buffer A: 10 mM Tris+15 mM ammonium sulphate in 20% EtOH, pH 7.3, buffer B: 80% EtOH, gradient 15-60% B. The collected fractions were desalted on Sep-Pak with 70% acetonitrile+0.1% TFA, neutralized by addition of ammonia and freeze-dried. The unoptimized yield was 11 mg (2%). The purity as evaluated by HPLC was >98%. LCMS 6236, $C_{282}H_{418}N_{66}O_{82}S_6$ requires 6237.

Example 12

$N^{\epsilon B29}$-(3-Carboxy-4-(14-carboxytetradecyloxy)benzoyl) desB30 human insulin Step 1: 4-Hydroxy isophthalic acid dimethyl ester

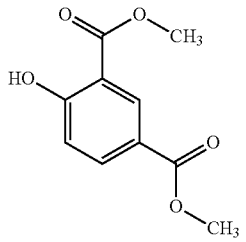

4-Hydroxy isophthalic acid (5 g, 27.5 mmol) was dissolved in 100 ml methanol, cooled to 0° C. under a flow of $N_2$, and thionyl chloride was added over ca. 5 min. The reaction was stirred at 0° C. for 30 min and then at room temperature for 1 h. The reaction was refluxed for 16 h. The solvent was removed under vacuum and the white solid was dissolved in AcOEt (100 ml). The solution was washed with water (2×50 ml), dried over $MgSO_4$ and concentrated under vacuum to yield a white crystalline solid (5.28 g, 92%).

$^1$H-NMR ($CDCl_3$, 300 MHz) δ: 11.20 (s, 1H), 8.57 (s, 1H), 8.12 (d, 1H), 7.02 (d, 1H), 3.99 (s, 3H), 3.91 (s, 3H)

Step 2: 4-Hydroxyisophthalic acid 1-methyl ester

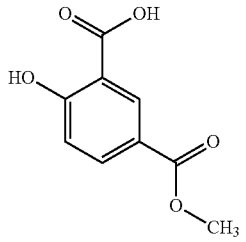

The compound was prepared in the manner described by Coutts, Ian G. C.; Edwards, Mark; Richards, David J. Synthesis 1981, 487. 4-Hydroxy isophthalic acid dimethyl ester (5.28 g, 25.1 mmol) was refluxed in pyridine under a flow of $N_2$. The reaction was monitored via TLC (20:10:1, heptane/AcOEt/AcOH) which indicated reaction completion after 8 h. The majority of the pyridine was removed under vacuum, and AcOEt (100 ml) was added. The solution was washed with 0.5 M HCl (3×50 ml). The acidic washes were then extracted with AcOEt (100 ml). The two organic phases were pooled, dried ($MgSO_4$) and concentrated to yield a white solid (4.85 g, 99%). The solid was recrystallized from toluene (200 ml) to yield white crystals (4.6 g, 92%).

$^1$H-NMR (DMSO, 400 MHz) δ: 8.39 (s, 1H), 8.05 (d, 1H), 7.07 (d, 1H), 3.84 (s, 3H).

$^{13}$C-NMR (DMSO, 400 MHz) δ 171.38, 165.59, 165.00, 136.26, 132.47, 120.91, 118.11, 113.72, 52.40.

Step 3: 4-Hydroxy isophthalic acid 3-tert-butyl ester 1-methyl ester

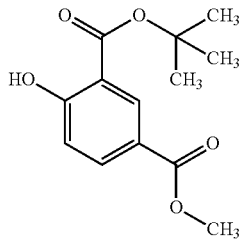

4-Hydroxyisophthalic acid 1-methyl ester (2 g, 10.2 mmol) was heated to 80° C. in toluene (50 ml) under a flow of $N_2$, and N,N-dimethylformamide di-tert-butyl acetal (4.88 ml, 20.4 mmol) was added over 30 sec. The reaction was stirred at 80° C., and monitored via TLC (20:10:1 (Heptane/AcOEt/AcOH). After 1 h more N,N-dimethylformamide di-tert-butyl acetal (4.88 ml, 20.4 mmol) was added, and once again after an additional hour. The reaction was stirred at 80° C. for 1 h., and the solvent was removed under vacuum. AcOEt (100 ml) was added and the solution was washed with water (3×50 ml), dried over $MgSO_4$, and concentrated under vacuum to yield light yellow crystals (2.64 g). The sample was recrystallized from heptane (10 ml) to yield off-white crystals (1.26 g, 49%).

$^1$H-NMR ($CDCl_3$, 300 MHz) δ: 11.55 (s, 1H), 8.47 (s, 1H), 8.08 (d, 1H), 6.98 (d, 1H), 3.91 (s, 3H), 1.64 (s, 9H), (also some contamination signals at 1.58 and 1.46).

Step 4: 15-Bromo-pentadecanoic acid tert-butyl ester

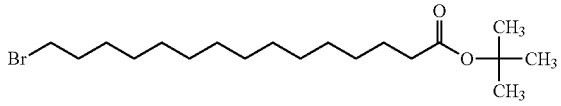

15-Bromo-pentadecanoic acid (5 g, 15.6 mmol) was heated to 70° C. under a flow of $N_2$ in toluene (50 ml). N,N-dimethylformamide di-tert-butyl acetal (18.7 ml, 77.8 mmol) was added over 10 min. The reaction was stirred at 55° C. for 16 h. The sample was concentrated under vacuum to a yellowish solid. The solid was dissolved in DCM (100 ml), washed with water (2×40 ml) and dried over $MgSO_4$ to yield a white residue (5.35 g). The sample was recrystallized from ethanol (50 ml), by initially cooling slightly and filtering off the first precipitate. The filtrate was then cooled on an ice bath to form the desired crystals, which were filtered off and dried to yield a white powder (1.37 g, 23%). Concentrating the filtrate to 20 ml and cooling yielded another batch of crystals (0.99 g, 15%).

HPLC-MS: m/z: 399+401 (M+23), Rt=7.04 min.

Step 5: 4-(14-tert-Butoxycarbonyl-tetradecyloxy)-isophthalic acid 3-tert-butyl ester 1-methyl ester

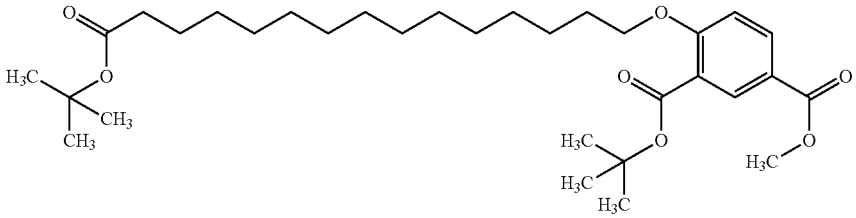

15-Bromo-pentadecanoic acid tert-butyl ester (598 mg, 1.59 mmol), 4-hydroxy isophthalic acid 3-tert-butyl ester 1-methyl ester (400 mg, 1.59 mmol) and $K_2CO_3$ (329 mg, 2.38 mmol) were placed in a flask with acetonitrile (25 ml) and refluxed under $N_2$. The reaction was followed via TLC (4:1 heptane/AcOEt). After 13 h the sample was concentrated under vacuum to near dryness. AcOEt (50 ml) and water (25 ml) were added to the residue. The phases were separated and the organic phase was washed with water and brine (25 ml each), dried over $MgSO_4$ and concentrated to yield an oil (841 mg, 97%).

HPLC-MS m/z: 571 (M+23) Rt=7.18 min.

Step 6: 4-(14-tert-Butoxycarbonyl tetradecyloxy) isophthalic acid 3-tert-butyl ester

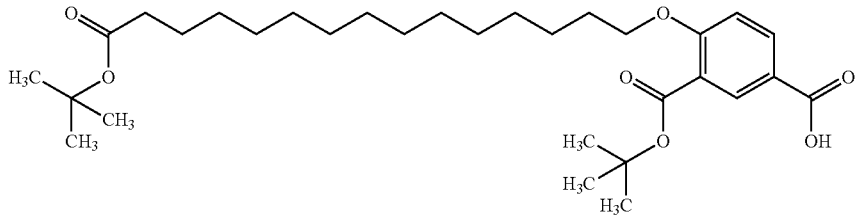

4-(14-tert-Butoxycarbonyl-tetradecyloxy)-isophthalic acid 3-tert-butyl ester 1-methyl ester (381 mg, 0.69 mmol) was dissolved in methanol (10 ml). The solution was cooled to 0° C. and 4 N NaOH (1 ml) was added. The solution was allowed to warm to rt and more methanol (15 ml) was added. The reaction was stirred at rt for 30 min under $N_2$, and at reflux for 2 h. The solution was cooled to 0° C. and 1 N HCl (1 ml) was added slowly. Water (25 ml) was added, and the solution was extracted with AcOEt (2×50 ml). The organic phases were pooled and washed with 1:1 water/sat. NaCl, dried over $MgSO_4$, and concentrated under vacuum to yield an oily solid (326 mg, 89%)

HPLC-MS m/z: 557 (M+23), Rt=6.5 min.

Step 7: 4-(14-tert-Butoxycarbonyl-tetradecyloxy) isophthalic acid 3-tert-butyl ester 1-(2,5-dioxo pyrrolidin-1-yl) ester

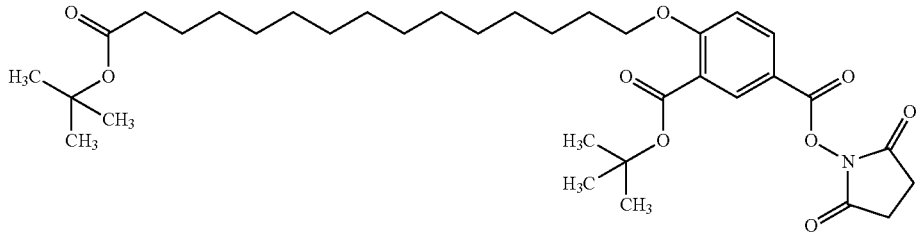

4-(14-tert-Butoxycarbonyl tetradecyloxy) isophthalic acid 3-tert-butyl ester (0.15 g, 0.28 mmol) was dissolved in THF (2 ml). DIEA (58 μl, 0.34 mmol) was added, and the solution was cooled to 0° C. TSTU (0.10 g, 0.28 mmol) was added. The reaction was stirred at 0° C. for 30 min and then at rt for 16 h. The sample was concentrated under vacuum to near dryness. AcOEt (20 ml) was added and the solution was washed with 0.2 N HCl and sat. $NaHCO_3$ (3×5 ml each), dried over $MgSO_4$ and concentrated to yield a residue (0.18 g). The residue was purified by flash chromatography (silica: AcOEt/heptane 3:7 (0.5 l), 1:1 (0.2 l)) yielding an oil with white solids (55 mg, 31%).

$^1$H-NMR (CDCl3, 400 MHz) δ: 8.43 (s, 1H), 8.16 (d, 1H), 7.00 (d, 1H), 4.10 (t, 2H), 2.90 (s, 4H), 2.20 (t, 2H), 1.86 (t, 2H), 1.58 (s, 12H=9H+$H_2O$), 1.49 (m, 2H), 1.44 (s, 9H), 1.26 (m, 20H).

Step 8: $N^{\epsilon B29}$-(3-Carboxy-4-(14-carboxytetradecyloxy)benzoyl)desB30 human insulin

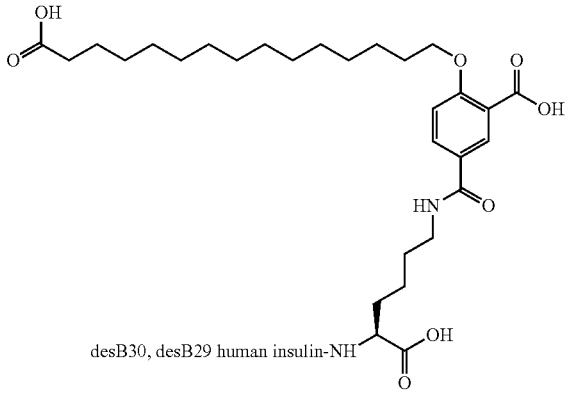

4-(14-tert-Butoxycarbonyl-tetradecyloxy)isophthalic acid 3-tert-butyl ester 1-(2,5-dioxo pyrrolidin-1-yl) ester (13 mg, 0.021 mmol) was coupled to A1,B1-d-Boc-desB30 human insulin (123 mg, 0.021 mmol), and treated with TFA analogous to method used in general procedure B, and purified as such to yield 38 mg product.

MS: m/z: 1528.8, calculated: 6111.1: (M+4)/4).

Example 13

$N^{\epsilon B29}$-(3-Carboxy-5-(14-carboxytetradecyloxy)benzoyl) desB30 human insulin

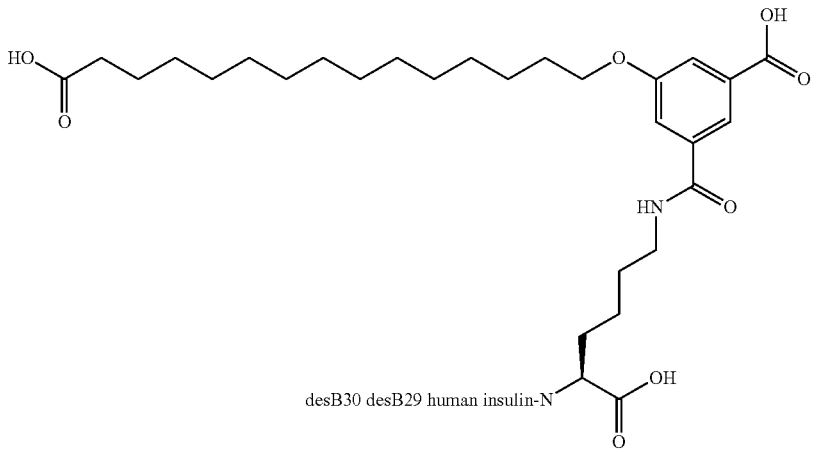

Step 1: 5-(14-tert-Butoxycarbonyltetradecyloxy) isophthalic acid dimethyl ester

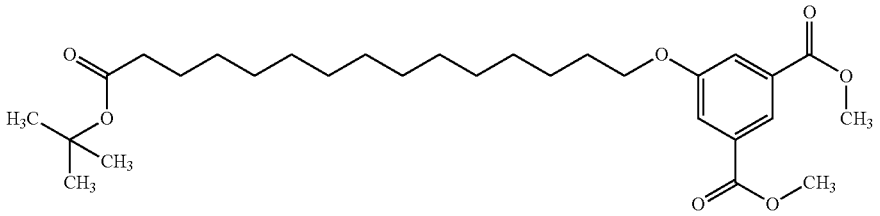

5-Hydroxy-isophthalic acid dimethyl ester (420 mg, 2 mmol), 15-bromo-pentadecanoic acid tert-butyl ester (755 mg, 2 mmol) and $K_2CO_3$ (415 mg, 3 mmol) were placed in a flask with acetonitrile (25 ml) and refluxed under $N_2$. The reaction was followed by TLC (4:1 heptane/AcOEt), which indicated reaction completion after 6 h. The sample was concentrated to near dryness. AcOEt (50 ml) and water (25 ml) were added to the residue. The phases were separated and the organic phase was washed with water and brine (25 ml each), dried over $MgSO_4$ and concentrated to yield a white crystalline solid (1.0 g, 100%).

HPLC-MS m/z: 529 (M+23), Rt=7.12 min.

$^1$H-NMR ($CDCl_3$, 300 MHz) δ: 8.26 (s, 1H), 7.74 (s, 2H), 4.03 (t, 2H), 3.94 (s, 6H), 2.20 (t, 2H), 1.80 (m, 2H), 1.57 (m, 2H), 1.44 (s, 9H), 1.26 (m, 20H).

Step 2: 5-(14-tert-Butoxycarbonyl-tetradecyloxy) isophthalic acid bis-(2,5-dioxo-pyrrolidin-1-yl) ester

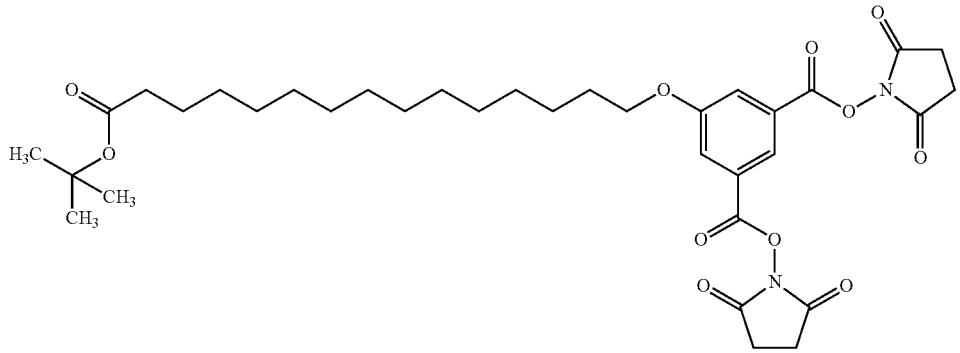

5-(14-tert-Butoxycarbonyltetradecyloxy) isophthalic acid dimethyl ester (965 mg, 1.91 mmol) was dissolved in methanol (50 ml) at 50° C. under a flow of $N_2$. After 30 min 1N NaOH (3.8 ml) was added and the solution was refluxed for 100 min. The solution was cooled and 1 N HCl (4.5 ml) was added. The sample was concentrated under vacuum, and the residue was taken up in AcOEt (20 ml) and water (25 ml). The phases were separated and the organic phase was washed with water (15 ml), died ($MgSO_4$) and concentrated to a white solid (900 mg).

This residue was dissolved in THF (10 ml) and placed in an ice bath. DIEA (386 μl, 2.26 mmol) was added, followed by TSTU (675 mg, 1.88 mmol). The reaction was stirred at 0° C. for 30 min and at rt for 16 h. The reaction mixture was concentrated under vacuum and AcOEt (50 ml) was added. The solution was washed with 0.2 N HCl (3×50 ml), water (50 ml) and sat. NaCl (30 ml), dried over $MgSO_4$, and concentrated under vacuum to yield an oil (1.12 g). The compound was purified by flash chromatography (silica: 2:3 AcOEt/heptane) to yield an oil containing some crystals (330 mg).

Some of this compound (290 mg) was dissolved in methanol (15 ml) and 1N NaOH (2.5 ml), and heated in an oil bath at 70° C. for 4.5 h. The sample was evaporated to dryness, and AcOEt (25 ml), water (15 ml) and 1N HCl (2.8 ml) were added. The phases were separated and the organic phase was washed with water (15 ml), dried over $MgSO_4$, and concentrated to a white residue (210 mg).

The residue was dissolved in THF (10 ml), DIPEA (75 μL, 0.44 mmol) was added, and the solution was cooled to 0° C. TSTU (173 mg, 0.48 mmol) was added and the reaction was stirred for 30 min at 0° C. and 16 h at rt. The reaction was evaporated to dryness, and AcOEt (25 ml) and 0.2 N HCl (26 ml) were added. The phases were separated and the organic phase was washed with 0.2 N HCl (2×25 ml), sat. NaHCO3 (3×25 ml) and sat. NaCl (25 ml), dried over $MgSO_4$ and concentrated under vacuum. DCM was added and the sample was concentrated to yield a residue. The residue wash purified by flash chromatography (silica: 7:3 AcOEt/heptane) to yield 90 mg, which was again purified by flash chromatography (silica: AcOEt/heptane 4:6 (100 ml) then 7:3 (100 ml)) to yield a white residue (19 mg, 8%)

HPLC-MS (Gradient) m/z: 696 (M+23); Rt: 6.04 min.

$^1$H-NMR ($CDCl_3$, 400 MHz) δ: 8.46 (s, 1H), 7.90 (s, 2H), 4.06 (t, 2H), 2.92 (s, 8H), 2.19 (t, 2H) 1.82 (m, 2H), 1.47 (m, 2H), 1.44 (s, 9H), 1.26 (m, 20H).

Step 3: $N^{\epsilon B29}$-(3-Carboxy-5-(14-carboxy-tetradecyloxy)-benzoyl)desB30 human insulin The 5-(14-tert-Butoxycarbonyl-tetradecyloxy)isophthalic acid bis-(2,5-dioxo-pyrrolidin-1-yl) ester was reacted with A1-B1-di-Boc-des-B30-insulin, treated with TFA and purified analogous to the general method B to yield the desired product.

Maldi-MS: m/z 6119.6: Calculated: 6111.1

Example 14

$N^{\epsilon B29}$-{4-Carboxy-4-[10-(4-carboxy-phenoxy)-decanoylamino]-butyryl}desB30 human insulin Step 1: 4-Hydroxy-benzoic acid tert-butyl ester

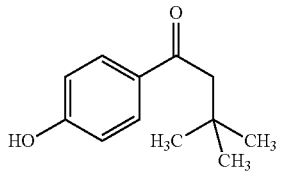

4-Hydroxy-benzoic acid (2 g, 14.5 mmol) was heated to 80° C. in dry toluene (3 Å molecular sieves) under a flow of $N_2$. N,N-dimethylformamide di-tert-butyl acetal (11.8 g, 57.92 mmol) is added over 5 min. The mixture was stirred at 80° C. for 50 min. The solution was washed with water, sat. $NaHCO_3$ and sat. NaCl (15 ml each), dried over $MgSO_4$, and concentrated to yield a yellow oil (2.92 g). Some of the oil (ca 1.7 g) was purified by küglerohr distillation (195°, 0.07 torr) to yield a colourless oil (1.18 g). $^1$H-NMR indicated the product contained approximately 30% of a by-product where the phenol group was protected with a tert-butyl group. The crude product was used in the subsequent reaction.

Step 2: 2-(10-Bromodecanoylamino) pentanedioic acid 5-benzyl ester 1-tert-butyl ester

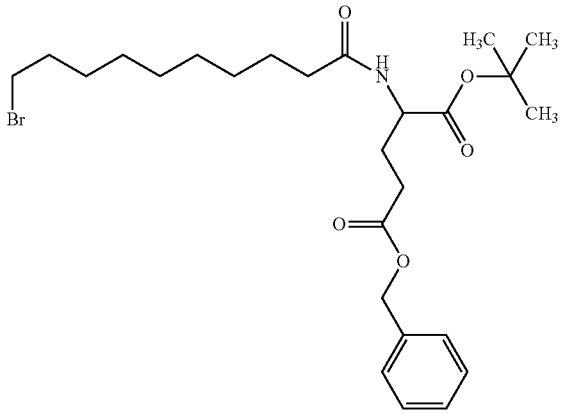

10-Bromodecanoic acid (3.20 g, 12.7 mmol) was dissolved in DMF (50 ml) and cooled to 0° C. under a flow of $N_2$. DIEA (3.92 g, 30.3 mmol) and EDAC (2.56 g, 13.3 mmol) were added, and the solution was stirred at 0° for 30 min. Glu-(OBn)-tBu HCl (2 g, 6.06 mmol) was added and the solution was stirred for 30 min at 0° C. and for 16 h at rt. The sample was concentrated under vacuum, and transferred to a reparatory funnel with AcOEt (100 ml). The solution was washed once with water and twice with 0.5 N NaOH and 5% AcOH (50 ml each), using some sat. NaCl and methanol to assist phase separation with the acidic washes. The organic phase was dried over $MgSO_4$, and concentrated to yield an oil (2.84 g). The oil was dissolved in 5 ml AcOEt and dispersed on a bed of silica in a glass filter. Eluting with AcOEt (150 ml), and concentrating under vacuum yielded a light brown oil (1.65 g, 52%)

HPLC-MS m/z: 550 ($M_+$23), Rt=5.19 min.

Step 3: 2-[10-(4-tert-Butoxycarbonylphenoxy)decanoylamino]pentanedioic acid 5-benzyl ester 1-tert-butyl ester

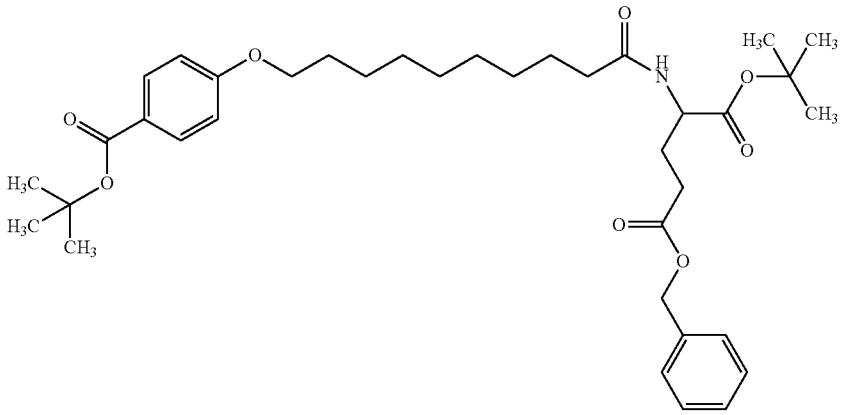

4-Hydroxy-benzoic acid tert-butyl ester (0.65 g, 3.08 mmol) was dissolved in acetonitrile (7.5 ml) and added to 2-(10-Bromodecanoylamino) pentanedioic acid 5-benzyl ester 1-tert-butyl ester (1.62 g, 3.08 mmol). Acetonitrile (90 ml) and $K_2CO_3$ (0.64 g, 4.62 mmol) was added and the mixture was refluxed for 16 h under a flow of $N_2$. The solvent was removed under vacuum. AcOEt (100 ml) was added and the solution was washed with water (2×50 ml) using sat. NaCl and methanol to aid phase separation, dried over $MgSO_4$, and concentrated to yield a light brown oil (2.18 g). The oil was purified by flash chromatography (silica, 95:5 DCM/AcOEt) to yield an oil (160 mg, 8%).

$^1$H-NMR ($CDCl_3$, 300 MHz) δ: (selected signals) 7.91 (d, 2H), 7.25 (s, 5H), 6.87 (d, 2H), 6.06 (d, 1H), 5.11 (s, 2H), 4.52 (m, 1H), 3.98 (d, 2H), 2.2-2.6 (m, 3H), 2.17 (t, 2H), 1.90-2.02 (m, 1H), 1.73-1.82 (m, 2H), 1.58 (s, 9H).

HPLC-MS (Fastgrad) m/z: 640 (M+1), Rt=3.0 min.

Step 4: 2-[10-(4-tert-Butoxycarbonylphenoxy)decanoylamino]pentanedioic acid 1-tert-butyl ester 5-(2,5-dioxopyrrolidin-1-yl) ester

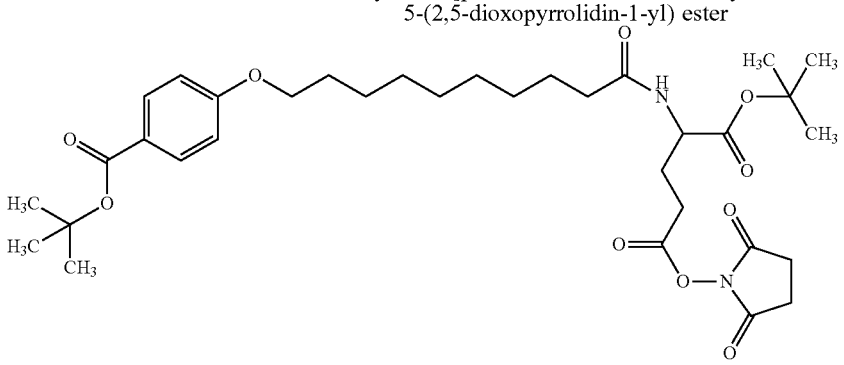

2-[10-(4-tert-Butoxycarbonylphenoxy)decanoylamino] pentanedioic acid 5-benzyl ester 1-tert-butyl ester (160 mg, 0.25 mmol) was dissolved in THF (10 ml) under a flow of $N_2$, and palladium (26 mg, 10% on carbon, 50% water) was added. The flask was evacuated and filled with $N_2$ four times, and a balloon filled with $H_2$ was connected to the system. The solution was stirred for 16 h at rt, and filtered through a bed of celite, washing with THF (100 ml). The filtrate was concentrated to yield the carboxylic acid (190 mg). The crude product was dissolved in THF (5 ml) and cooled to 0° C. DIEA (64 μl, 0.375 mmol) and TSTU (0.09 g, 0.3 mmol) were added. The mixture was stirred at 0° C. for 1 h and at rt for 16 h. AcOEt (50 ml) was added, and the solution was washed with 0.2 M HCl (3×15 ml) and sat. $NaHCO_3$ (2×15 ml), dried over $MgSO_4$, and concentrated to yield an oil (167 mg). Purification by flash chromatography (2:1 AcOEt/heptane) yielded a 107 mg of a colorless oil.

$^1$H-NMR ($CDCl_3$, 300 MHz) (selected signals) δ 7.92 (d, 2H), 6.87 (d, 2H), 6.22 (d, 1H), 4.61 (m, 1H) 3.99 (t, 2H), 2.83 (s, 4H), 2.62-2.75 (m, 2H), 2.30 (m, 1H), 2.22 (t, 2H), 2.10 (m, 1H), 1.58 (s, 9H).

Step 5: $N^{\epsilon B29}$-{4-Carboxy-4-[10-(4-carboxy-phenoxy)-decanoylamino]-butyryl} desB30 human insulin

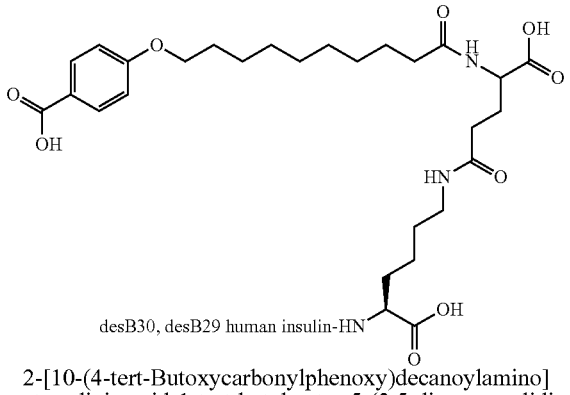

2-[10-(4-tert-Butoxycarbonylphenoxy)decanoylamino] pentanedioic acid 1-tert-butyl ester 5-(2,5-dioxopyrrolidin-1-yl) ester was coupled to desB30 human insulin in similar fashion as described in General Procedure A. The intermediate product was purified by preparative HPLC ($C_{18}$-5 cm dia.) before treating with TFA. The product was purified by preparative HPLC ($C_4$ 2 cm dia.) 15-65% acetonitrile) followed by ion exchange chromatography (Column: Amersham Resource Q-6 ml, Buffer A: 0.24% w/w tris, 0.25% w/w ammonium acetate, 42.5% w/w ethanol, pH 7.5 with acetic acid, Buffer B: 0.24% w/w tris, 2.5% w/w ammonium acetate, 42.5% w/w ethanol, pH 7.5 with acetic acid.

HPLC-MS: m/z: 1532.6 (M+4)/4), calculated: 6126

Example 15

$N^{\epsilon B29}$-[3-Carboxy-5-(octadecandioyl-N-carboxyethylglycin)aminobenzoyl] desB30 human insulin

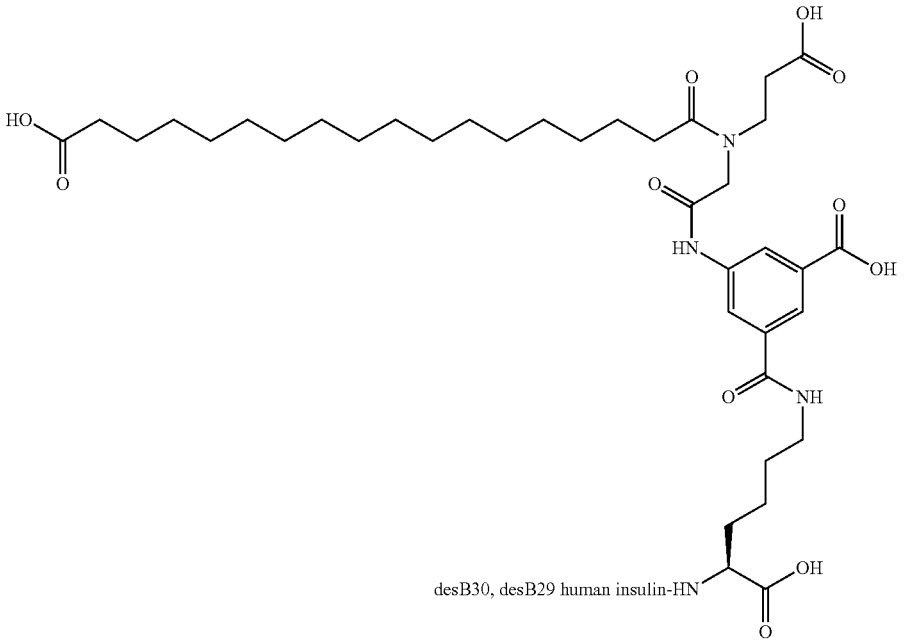

Step 1

Synthesis of 3-(Benzyloxycarbonylmethylamino)propionic acid tert-butyl ester

H-Gly-OBn, HCl (3.03 g, 15 mmol) was dissolved in dry DMF (15 ml) and cooled on an ice bath. TEA (2.10, 15 mmol) was added under precipitation of TEA-hydrochloride. The suspension was stirred for 5 min before t-butyl acrylate (2.20 ml, 15 mmol) was added. The cooling bath was allowed to reach RT slowly and stirring was continued under Nitrogen for 2 days. The reaction mixture was filtered and the filtrate was concentrated. The residue, still containing DMF, was dissolved in EtOAc and washed with sat aq $NaHCO_3$ (2×) and water (1×). The organic layer was filtered before drying ($Na_2SO_4$) and concentration to give an oil Purification by chromatography or preparative HPLC gave 3-(benzyloxycarbonylmethylamino)propionic acid tert-butyl as a clear oil (0.739 g, 17%).

$^1$H-NMR ($CDCl_3$) δ: ppm 1.46 (s, 9H) 2.50-2.61 (m, 2H) 2.82-2.99 (m, 2H) 3.31 (s, 2H) 5.14 (s, 2H) 7.29-7.43 (m, 5H).

Step 2

Synthesis of 17-[Benzyloxycarbonylmethyl-(2-tert-butoxycarbonyl-ethyl)-carbamoyl]-heptadecanoic acid tert-butyl ester 3-(Benzyloxycarbonylmethylamino)propionic acid tert-butyl ester (0,030 g, 0.1 mmol) and octadecanedioic acid tert-butyl ester 2,5-dioxo-pyrrolidin-1-yl ester (0,050 mg, 0.1 mmol) was suspended in dry DMF (1 ml). HOAt (0.014 g, 0.1 mmol) and DIPEA (0.21 ml, 1.2 mmol) was added. The yellow reaction mixture was stirred under nitrogen for 42 h. The reaction mixture was concentrated. The residue was redissolved in EtOAc and washed with 0.1 N HCl (2×), water (1×), dried ($Na_2SO_4$) and concentrated to give 17-[Benzyloxycarbonylmethyl-(2-tert-butoxycarbonyl-ethyl)-carbamoyl]-heptadecanoic acid tert-butyl ester in 85% yield (55 mg).

$^1$H-NMR ($CDCl_3$) δ: ppm 1.3 (m, 26H) 1.38 (s, 9H), 1.46 (s, 9H), 1.6 (m, 4H), 2.2 (m, 2H), 2.35 (m, 2H), 2.65 (m, 2H), 2.85 (s, 2H) 3.65 (m, 2H), 5.15 (s, 2H) 7.35 (m, 5H).

Step 3

Synthesis of 17-[(2-tert-Butoxycarbonyl-ethyl)-carboxymethyl-carbamoyl]-heptadecanoic acid tert-butyl ester 17-[Benzyloxycarbonylmethyl-(2-tert-butoxycarbonyl-ethyl)-carbamoyl]-heptadecanoic acid tert-butyl ester (0,054 g, 0.08 mmol) was dissolved in THF (2 ml). 10% Palladium on Charcoal was added and the mixture was hydrogenated at 1 atm and RT over the week-end. The dry reaction mixture was dissolved in EtOAc and filtered 3 times to remove the carbon. The filtrate was concentrated to give 17-[(2-tert-Butoxycarbonyl-ethyl)-carboxymethyl-carbamoyl]-heptadecanoic acid tert-butyl ester in 80% yield (37 mg).

$^1$H-NMR ($CDCl_3$) δ: ppm 1.3 (m, 26H) 1.40 (s, 9H), 1.46 (s, 9H), 1.6 (m, 4H), 1.75 (p, 2H), 2.2 (m, 2H), 2.35 (m, 2H), 2.63 (m, 2H), 2.83 (s, 2H).

Step 4

Synthesis of 5-{2-[(2-tert-Butoxycarbonyl-ethyl)-(17-tert-butoxycarbonyl-heptadecanoyl)-amino]-acetylamino}-isophthalic acid mono-tert-butyl ester 17-[(2-tert-Butoxycarbonyl-ethyl)-carboxymethyl-carbamoyl]-heptadecanoic acid tert-butyl ester (0.130 g) was dissolved in dry DCM (5 ml). HOAt (0.36 mg) and DIC (0.045 ml) was added the mixture was refluxed for 1 h under nitrogen. The reaction mixture was cooled to room temperature and 5-amino-isophthalic acid mono t-Butyl ester (60 mg) was added. After stirring for 1 h DIPEA (0.050 ml) was added, the orange reaction mixture turns yellow. After stirring for 2 days, the reaction mixture was concentrated. The residue was redissolved in EtOAc and extracted with 0.1 N HCl (2×) and brine (1×), dried ($Na_2SO_4$), and concentrated to give an sirup, which solidifies on standing. 5-{2-[(2-tert-Butoxycarbonyl-ethyl)-(17-tert-butoxycarbonyl-heptadecanoyl)-amino]-acetylamino}-isophthalic acid mono-tert-butyl ester was obtained in a quantitative yield (214 mg), contaminated with an impurity. HPLC/MS 775 (M), rt 7.64 min.

Step 5

Synthesis of 5-{2-[(2-tert-Butoxycarbonyl-ethyl)-(17-tert-butoxycarbonyl-heptadecanoyl)-amino]-acetylamino}-isophthalic acid 1-tert-butyl ester 3-(2,5-dioxo-pyrrolidin-1-yl) ester 5-{2-[(2-tert-Butoxycarbonyl-ethyl)-(17-tert-butoxycarbonyl-heptadecanoyl)-amino]-acetylamino}-isophthalic acid mono-tert-butyl ester (214 mg) was dissolved in dry THF and TSTU (0.105 mg) and DIPEA (0.1 ml) was added. The mixture was stirred at room temperature under nitrogen. After 20 h the reaction mixture was concentrated. The residue was redissolved in EtOAc and filteret. The filtrate was extracted with 0.1 N HCl (2×) and brine (1×), dried ($Na_2SO_4$) and concentrated to give 5-{2-[(2-tert-Butoxycarbonyl-ethyl)-(17-tert-butoxycarbonyl-heptadecanoyl)-amino]-acetylamino}-isophthalic acid 1-tert-butyl ester 3-(2,5-dioxo-pyrrolidin-1-yl) ester as a yellow sirup in 90% yield (218 mg).

Step 6

Synthesis of $N^{\epsilon B29}$-[3-Carboxy-5-(octadecandioyl-N-carboxyethylglycin)amino-benzoyl] desB30 insulin 5-{2-[(2-tert-Butoxycarbonyl-ethyl)-(17-tert-butoxycarbonyl-heptadecanoyl)-amino]-acetylamino}-isophthalic acid 1-tert-butyl ester 3-(2,5-dioxo-pyrrolidin-1-yl) ester was reacted with A1,B1-diBoc insulin as described in general procedure B. The product was purified by preperative HPLC to give the title compound. Over all yield for coupling and hydrolysis, 18% (21 mg).

MALDI-MS (SA): 6288.8. anal. HPLC (neut), 93.8.5% purity, rt 10.22 min. (Column: C4 5μ 150×4.60 mm "phenomerex, Jupiter" Buffer A: 10 mM Tris, 15 mM (NH4) 2SO4, pH 7.3, 20% $CH_3CN$ in MQ water. Buffer B: 80% $CH_3CN$, 20% MQ-water, Flow: 1.5 ml/min; Gradient: 0 min 5% B→20 min 55% B→22 min 80% B→24 min 80% B=25 min 5% B) anal. HPLC (acidic), 100% purity, rt 11.694 min (Column: C4 5μ 150×4.60 mm "phenomerex, Jupiter" Buffer A: 0.1% TFA, 10% $CH_3CN$, 89.9% MQ-water Buffer B: 0.1% TFA, 80% $CH_3CN$, 19.9% MQ-water, Flow: 1.5 ml/min; Gradient: 0 min 20% B→17 min 80% B→22 min 80% B→23 min 20% B→30 min 20% B.

Example 16

General Procedure A, Acylation Using desB30 Human Insulin $N^{\epsilon B29}$-{3-[(3,5-Bis-carboxymethoxy-benzyl)-(15-carboxypentadecanoyl)amino]-propionyl desB30 human insulin Step 1: Synthesis of Hexadecanedioic acid mono-(4-methoxy-benzyl) ester

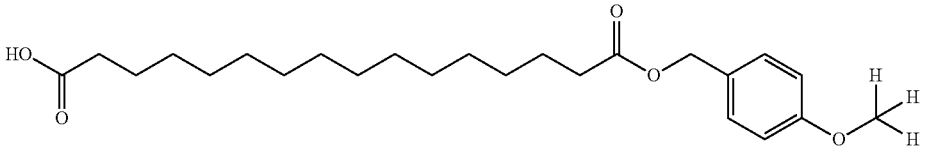

Hexadecandioic acid (2 g, 7 mmol) was dissolved in dry NMP (25 mL). Diisopropylamin (1.2 mL, 7 mmol) and 4-methoxybenzyl chloride (0.95 mL, 7 mmol) was added, followed by NaI (0.52 g, 3.5 mmol). The mixture was heated to 80° C. for 1 hour, poured into water (100 mL) and filtered. The precipate was washed with dichloromethane (150 mL), the dichoromethane phase was dried ($Na_2SO_4$) and solvent removed in vacuo to yield the crude product, which was recrystalized several times from heptane to yield hexadecanedioic acid mono-(4-methoxy-benzyl) ester.

$^1$H NMR ($CDCl_3$): δ 7.28 (d, 2H), 6.87 (d, 2H), 5.02 (s, 2H), 3.78 (s, 3H), 2.31 (m, 4H), 1.60 (m, 4H), 1.20 (m, 20H).

Step 2: Synthesis of (3-Tert-Butoxycarbonyl-methoxy-5-formylphenoxy)acetic acid tert-butyl ester

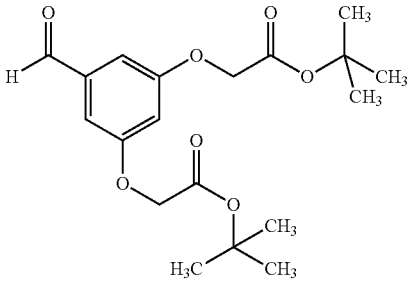

4,5 dihydroxybenzaldehyde (2.5 g, 18.1 mmol) was dissolved in NMP (120 mL). Potassium carbonate (10 g, 72.4 mmol) was added, followed by tert-butyl bromoacetate.

The mixture was stirred at room temperature, under nitrogen overnight. The reaction was filtered and separated between diethyl ether (400 mL) and water (400 mL). The organic phase was dried ($Na_2SO_4$) and solvent removed in vacuo to yield the crude product as an oil which solidifies by standing. The crude product was used in the next step without further purification.

HPLC-MS:m/z=(389, M+Na); $R_t$=4.50 min.

$^1$H NMR ($CDCl_3$): δ 9.85 (s, 1H), 7.00 (s, 2H), 6.75 (s, 1H), 4.58 (s, 4H), 1.44 (2, 18H)

Step 3: Synthesis of 3-(3,5-Bis-tert-butoxycarbonyl-methoxybenzylamino)propionic acid

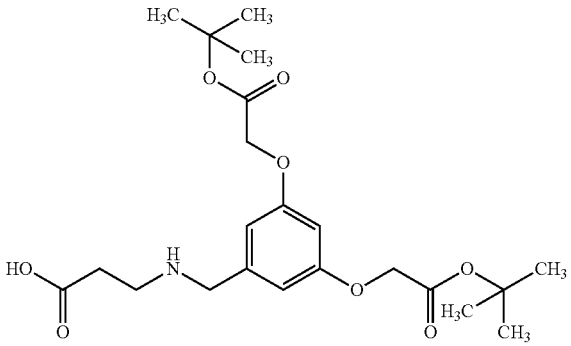

Beta-alanine (0.5 g, 5.68 mmol) was dissolved in methanol (20 mL). (3-Tert-Butoxycarbonylmethoxy-5-formylphenoxy)acetic acid tert-butyl ester (2.08 g, 5.58 mmol) was dissolved in methanol (2 mL) and added. The mixture was heated to reflux for 1 hour and allowed to cool to room temperature. Sodium cyanoborohydride (282 mg, 4.54 mmol) was added and the mixture stirred at room temperature, after 1 hour acetic acid was added (2 mL) and the mixture was stirred for an additional hour before being poured into water (50 mL) and stirred overnight. The water phase was washed with ethyl acetate (2×50 mL). The organic phase was dried ($Na_2SO_4$) and solvent removed in vacuo to yield the crude product. The crude product was used in the next step without further purification.

HPLC-MS:m/z=(440, M+Na); $R_t$=3.24 min.

Step 4: Synthesis of 15-[(3,5-Bis-tert-butoxycarbonylmethoxybenzyl)-(2-carboxyethyl)carbamoyl] pentadecanoic acid 4-methoxybenzyl ester

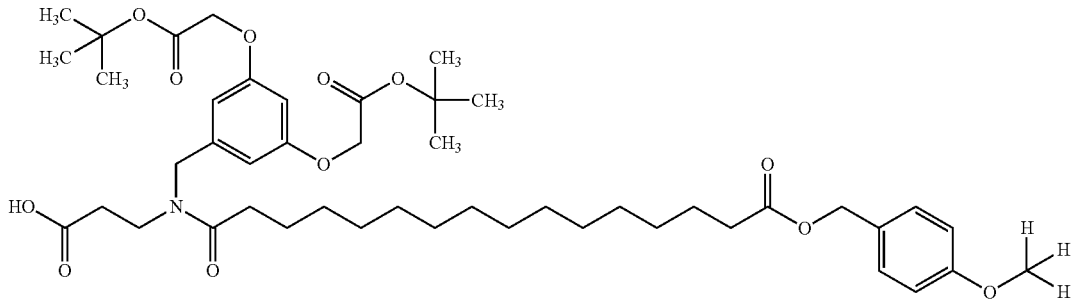

Hexadecanedioic acid mono-(4-methoxy-benzyl) ester (0.4 g, 0.98 mmol) was dissolved in ethyl acetate (10 mL). N-Ethyl-N-(3-dimethylaminopropyl)-carbodiimide hydrochloride (0.187 g, 0.98 mmol) and 1-hydroxy-7-azabenzotriazole (0.134 g, 0.98 mmol) was added and the mixture was stirred at 50° C. for 1 hour. After cooling to room temperature, diisopropylethylamin (0.50 mL, 2.95 mmol) was added followed by 3-(3,5-Bis-tert-butoxycarbonylmethoxybenzylamino)propionic acid (0.432 g, 0.98 mmol). The mixture was stirred overnight under nitrogen at room temperature. The mixture was separated between ethyl acetate (200 mL) and water (2×100 mL). The organic phase was dried ($Na_2SO_4$), solvent removed in vacuo. The crude product was purified by RP-HPLC on C18-column, buffer A: 0.1% TFA, buffer B: MeCN+0.1% TFA; gradient 80-100% B to yield the title compound.

HPLC-MS:m/z=(547, M+Na); $R_t$=6.17 min.

Step 5: Synthesis of 15-{(3,5-Bis-tert-butoxycarbonylmethoxybenzyl)-[2-(2,5-dioxo-pyrrolidin-1-yloxycarbonyl)ethyl]carbamoyl}pentadecanoic acid 4-methoxy-benzyl ester

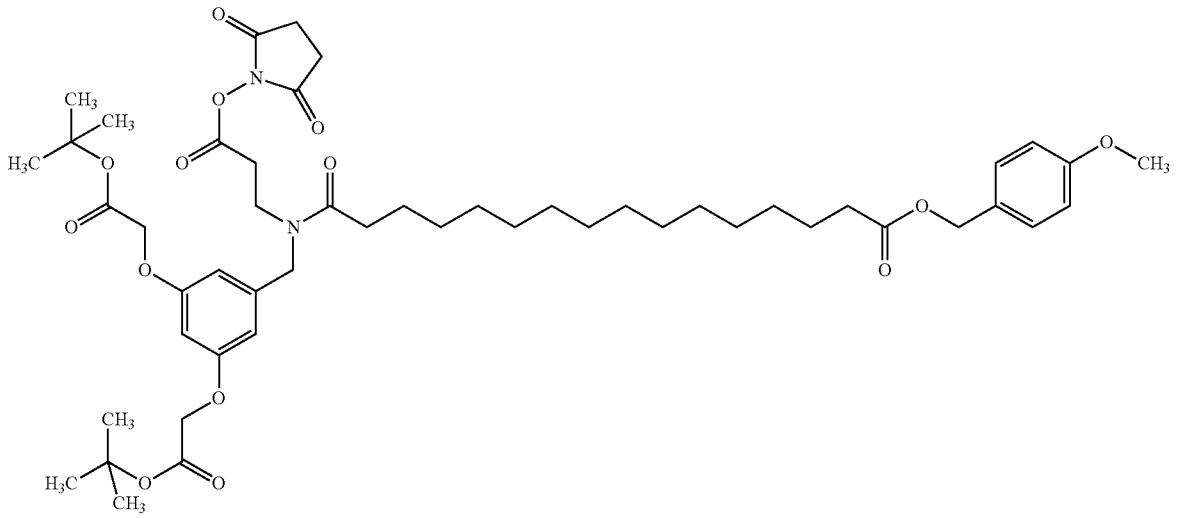

15-[(3,5-Bis-tert-butoxycarbonylmethoxybenzyl)-(2-carboxyethyl)carbamoyl]pentadecanoic acid 4-methoxybenzyl ester (190 mg, 0.23 mmol) was dissolved in THF (5 mL). The mixture was cooled with an ice bath. Diisopropylethylamin (0.047 mL, 0.28 mmol) and O—(N-succinimidyl)-N,N,N',N'-tetramethyluronium tetrafluoroborate (83 mg, 0.28 mmol) was added. The mixture was stirred under nitrogen at 0° C. After 30 minutes the ice cooling was removed and the mixture was stirred for an additional 3 hours. Solvent removed in vacuo. The crude product was dissolved in ethyl acetate (50 mL), washed with aqueous phosphate buffer (pH=5.5) (3×25 mL). The organic phase was dried ($Na_2SO_4$), solvent removed in vacuo to yield the title compound (163 mg) which was used in subsequent step.

HPLC-MS: m/z=924; $R_t$=6.5 min.

Step 6: Synthesis of $N^{\epsilon B29}${3-[(3,5-Bis-carboxymethoxy-benzyl)-(15-carboxy-pentadecanoyl)-amino]-propionyl desB30 human insulin

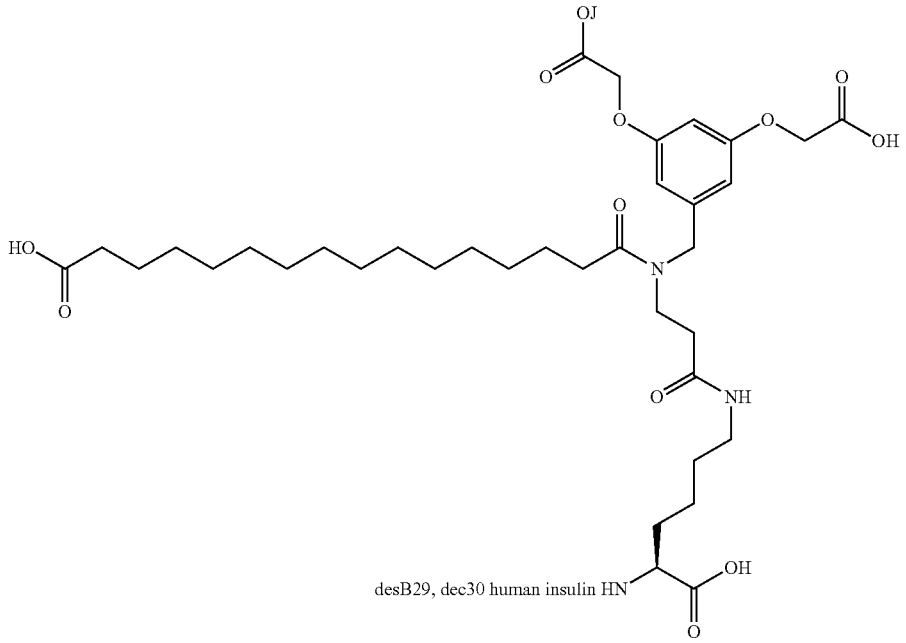

DesB30 human insulin (742 mg, 0.13 mmol) was dissolved in aqueous $Na_2CO_3$ (100 mM, 14.7 mL). 15-{(3,5-Bis-tert-butoxycarbonylmethoxybenzyl)-[2-(2,5-dioxo-pyrrolidin-1-yloxycarbonyl)ethyl]carbamoyl}pentadecanoic acid 4-methoxy-benzyl ester (120 mg, 0.13 mmol) was dissolved in acetonitrile (7.4 mL) and added. The mixture was stirred very slowly for 1 hour at RT. pH was adjusted to 5.5 with aqueous HCl (1 N) and the suspension was allowed to stand for 10 minutes at 0° C. The precipitate was isolated by centrifugation and treated with mixture of p-cresol (0.750 mL) and TFA (14.25 mL) for 10 minutes. Poured into ice cooled diethylether (30 mL), and the crude product was isolated by centrifuge and purified with RP-HPLC on a Waters Prep LC2000, on C18, 5 cm×20 cm, flow 20 ml/min using acetonitrile/water 15-55% gradient containing 0.1% TFA. Fractions containing product was collected and lyophilized. To the lyophilized material was added water (7.2 mL) and pH adjusted to 8.98 with 1 N+0.1 N NaOH. The pH was adjusted back to 5.2-5.5 with 0.1 N HCl. The product precipitated, isolated by centrifugation and lyophilized to give the title compound. HPLC-MS: m/z=1257 (m/5), $R_t$=3.27 min.

Example 17

$N^{\epsilon B29}$-3-[4'-(2-Carboxyethyl)biphenyl-4-yl]propionyl-γ-L-glutamyl desB30 insulin

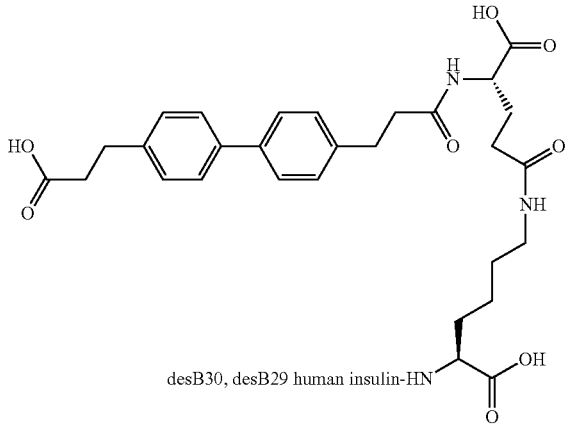

Step 1: Synthesis of tert-butyl 3-(4-bromophenyl)propionate 3-(4-Bromophenyl)propionic acid (1.0 g, 4.4 mmol) was dissolved in toluene (15 ml) and treated with N,N-dimethylformamide ditert-butyl acetal (1.8 g, 8.7 mmol). The mixture was heated to 90° C. for 5 hours, and then treated with more N,N-dimethylformamide ditert-butyl acetal (1.8 g, 8.7 mmol). The mixture was left at 90° C. overnight. Ethyl acetate was added (25 ml) and the organic phase was washed with 2×0.1 M HCl, 2×5% $Na_2CO_3$ and water. Drying over $MgSO_4$ and evaporation in vacuo gave tert-butyl 3-(4-bromophenyl)propionate, 0.735 g (59%).

$^1$H-NMR ($CDCl_3$) δ: 7.47 (d, 2H), 7.08 (d, 2H), 2.87 (t, 2H), 2.52 (t, 2H), 1.42 (s, 9H).

Step 2: Synthesis of tert-butyl 3-[4'-(2-Carboxy-ethyl)-biphenyl-4-yl]-propionate Tert-butyl 3-(4-bromophenyl)propionate (433 mg, 1.52 mmol) in acetonitrile-water (3:1, 13 ml) under argon atmosphere was treated with 4-(2-carboxyethyl)benzeneboronic acid (294 mg, 1.52 mmol), $K_2CO_3$ (251 mg, 1.82 mmol) and $(Ph_3P)_4Pd$ (87 mg, 73 μmol), and the stirred mixture was heated at 90° C. for 4 hours. Excess ethyl acetate and 2 M HCl was added and the organic phase was washed with 2×2 M HCl and 2× water. Drying over $MgSO_4$ and evaporation in vacuo gave the crude product, which was purified by chromatography on silica column eluted with ethyl acetate/hexane/acetic acid 50:50:1 to provide tert-butyl 3-[4'-(2-Carboxy-ethyl)-biphenyl-4-yl]-propionate, 330 mg (62%).

$^1$H-NMR ($CDCl_3$) δ: 7.50 (dd, 4H), 7.26 (dd, 4H), 3.00 (t, 2H), 2.94 (t, 2H), 2.72 (t, 2H), 2.57 (t, 2H), 1.42 (s, 9H).

Step 3: Synthesis of tert-butyl 3-[4'-(2-O-succinimidyl-carboxy-ethyl)-biphenyl-4-yl]-propionate Tert-butyl 3-[4'-(2-Carboxy-ethyl)-biphenyl-4-yl]-propionate (330 mg, 0.93 mmol) was dissolved in THF (5 ml) and treated with TSTU (336 mg, 1.12 mmol) and DIEA (191 μL, 1.12 mmol), and the mixture was stirred at room temperature overnight. The mixture was filtered, the solvent was evaporated in vacuo, and the crude product was dissolved in ethyl acetate, and washed with 2×0.1 M HCl, 2×5% $Na_2CO_3$ and water. Drying over $MgSO_4$ and evaporation in vacuo gave tert-butyl 3-[4'-(2-O-succinimidyl-carboxy-ethyl)-biphenyl-4-yl]-propionate, 374 mg (89%).

$^1$H-NMR ($CDCl_3$) δ: 7.50 (dd, 4H), 7.27 (dd, 4H), 3.10 (t, 2H), 2.95 (m, 4H), 2.84 (s, 4H), 2.57 (t, 2H), 1.42 (s, 9H).

Step 4: Synthesis of tert-butyl 3-[4'-(2-O-succinimidyl-carboxy-ethyl)-biphenyl-4-yl]-propionate-L-glutamyl α-tert-butyl ester Tert-butyl 3-[4'-(2-O-succinimidyl-carboxy-ethyl)-biphenyl-4-yl]-propionate (100 mg, 0.22 mmol) was dissolved in DMF (1.0 ml) and treated with L-Glu-OtBu (50 mg, 0.25 mmol) and DIEA (56 μL, 0.33 mmol) and stirred at room temperature overnight. The solvent was removed in vacuo, and the residue was dissolved in ethyl acetate and washed with 2×0.2 M HCl, water and brine. Drying over $MgSO_4$ and evaporation in vacuo gave tert-butyl 3-[4'-(2-O-succinimidyl-carboxy-ethyl)-biphenyl-4-yl]-propionate-L-glutamyl α-tert-butyl ester, 119 mg (100%).

$^1$H-NMR ($CDCl_3$) δ: 7.48 (dd, 4H), 7.24 (dd, 4H), 6.30 (bd, 1H), 4.54 (m, 1H), 2.95 (m, 4H), 2.56 (m, 4H), 2.31 (m, 2H), 2.16 (m, 1H), 1.86 (m, 1H), 1.44 (s, 9H), 1.42 (s, 9H).

Step 5: Synthesis of tert-butyl 3-[4'-(2-O-succinimidyl-carboxy-ethyl)-biphenyl-4-yl]-propionate-L-glutamyl-γ-O-succinimidyl α-tert-butyl ester Tert-butyl 3-[4'-(2-O-succinimidyl-carboxy-ethyl)-biphenyl-4-yl]-propionate-L-Glu-OtBu (120 mg, 0.22 mmol) in THF (2 ml) and reacted with TSTU (80 mg, 0.27 mmol) and DIEA (46 μL, 0.27 mmol) as described in step 3 above to provide tert-butyl 3-[4'-(2-O-succinimidyl-carboxy-ethyl)-biphenyl-4-yl]-propionate-L-glutamyl-γ-O-succinimidyl α-tert-butyl ester, 136 mg (96%).

$^1$H-NMR ($CDCl_3$) δ: 7.50 (dd, 4H), 7.25 (dd, 4H), 6.21 (d, 1H), 4.60 (m, 1H), 3.00 (t, 2H), 2.94 (t, 2H), 2.78 (s, 4H), 2.56 (m, 6H), 2.36 (m, 1H), 2.04 (m, 1H), 1.46 (s, 9H), 1.43 (s, 9H).

Step 5: Synthesis of $N^{\epsilon B29}$-3-[4'-(2-Carboxy-ethyl)-biphenyl-4-yl]-propionyl-γ-L-glutamyl desB30 insulin DesB30 human insulin (500 mg, 88 μmol) was reacted with tert-butyl 3-[4'-(2-O-succinimidyl-carboxy-ethyl)-biphenyl-4-yl]-propionate-L-glutamyl-γ-O-succinimidyl α-tert-butyl ester (67 mg, 105 μmol), and the product was isolated, deprotected and HPLC-purified as described for example 11. LCMS: 6114.0, $C_{276}H_{399}N_{65}O_{81}S_6$ requires 6116.0.

Example 18

General procedure A, Acylation using desB30 human insulin $N^{\epsilon B29}$-ω-carboxypentadecanoy-(4-aminomethylbenzoyl)-γ-L-glutamyl desB30 human insulin-Glu-desB30 insulin Step 1: Synthesis of 4-[(15-tert-Butoxycarbonylpentadecanoylamino)methyl]benzoic acid

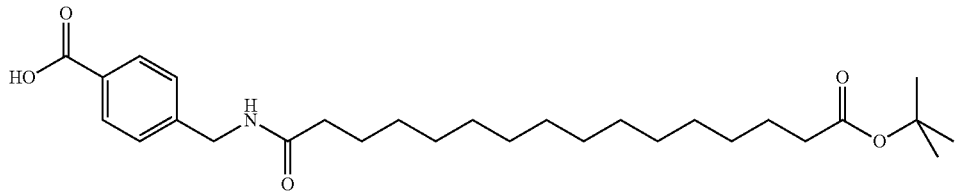

To 4-(Aminomethyl)benzoic acid (0.2 g, 1.32 mmol) was added in NMP (5 mL). Hexadecanedioic acid tert-butyl ester 2,5-dioxo-pyrrolidin-1-yl ester (0.58 g, 1.32 mmol) was added and the mixture was stirred at room temperature overnight. The mixture was poured into water (100 mL), the precipitate was isolated by filtration and dried in vacuo. The crude material was recrystalized from toluene to give 4-[(15-tert-butoxycarbonylpentadecanoylamino)methyl]benzoic acid (413 mg).

$^1$H NMR (DMSO-$d_6$): δ 12.77 (br s, 1H), 8.36 (t, 1H), 7.87 (d, 2H), 7.32 (d, 2H), 4.32 (d, 2H), 2.15 (q, 4H), 1.48 (m, 4H), 1.38 (s, 9H), 1.28-1.18 (br s, 20H)

Step 2: Synthesis of (S)-2-{4-[(15-tert-Butoxycarbonyl-pentadecanoylamino)-methyl]-benzoylamino}-pentanedioic acid 1-tert-butyl ester

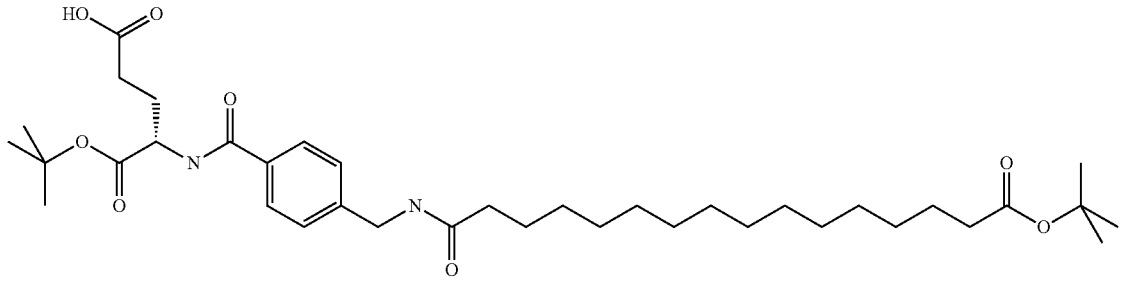

4-[(15-tert-butoxycarbonylpentadecanoylamino)methyl] benzoic acid (413 mg, 0.868 mmol) was dissolved in THF (5 mL), the solution was cooled with an icebath. DIPEA (0.33 mL, 1.91 mmol) and TSTU (314 mg, 1.04 mmol) were added. The mixture was stirred under nitrogen while cooling was maintained. After 30 minutes the icebath was removed and the mixture was stirred for additional 3 hours at room temperature. The mixture was diluted with NMP (5 mL) and H-GluOtBu (0.21 g, 1.04 mmol) was added, the mixture was stirred overnight at room temperature. The mixture was separated between ethyl acetate (100 mL) and water (100 mL), the organic phase dried ($Na_2SO_4$) and solvent removed in vacuo. The crude material was purified on silica using DCM/ethanol (90:10) to give (S)-2-{4-[(15-tert-Butoxycarbonyl-pentadecanoylamino)-methyl]-benzoylamino}-pentanedioic acid 1-tert-butyl ester.

$^1$H NMR ($CDCl_3$): δ 7.63 (d, 2H), 7.20 (m, 3H), 6.52 (t, 1H), 4.62 (m, 1H), 4.40 (d, 2H), 2.50 (m, 2H), 2.30-2.10 (m, 6H), 1.70-1.55 (m, 4H), 1.50 (s, 9H), 1.45 (s, 9H), 1.35-1.20 (m, 20H)

Step 3: Synthesis of $N^{\epsilon B29}$-ω-carboxypentadecanoyl-(4-aminomethylbenzoyl)-γ-L-glutamyl desB30 human insulin

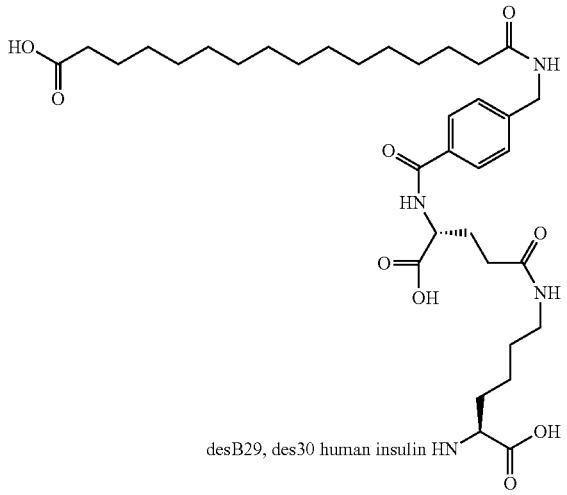

The compound was prepared similar as described in step 3 and step 4 in general procedure B using (S)-2-{4-[(15-tert-Butoxycarbonyl-pentadecanoylamino)-methyl]-benzoylamino}-pentanedioic acid 1-tert-butyl ester.

Example 19

$N^{\epsilon B29}$ (4-{[(2-Carboxy-ethyl)-(15-carboxy-pentadecanoyl)amino]methyl}benzoyl)-γ-D-glutamyl desB30 human insulin Step 1: Synthesis of resin bound Fmoc-D-Glu-OtBu 1 g of polystyrene resin functionalized with a 2-chlorotrityl chloride linker (1.4 mmol/g) was vortexed with NMP (10 mL) and 1,2-dichloropropane (10 mL) for 1 hour. The resin was filtered and washed with dichloromethane (20 mL). Fmoc-D-Glu-OtBu (596 mg, 1.4 mmol) was dissolved together with diisopropylethylamine (0.96 mL, 5.6 mmol) in dichloromethane (20 mL) and added to the resin. After shaking the suspension for 2 hours at 25° C., the resin was isolated by filtration and washed with NMP (2×20 mL)

Step 2: Synthesis of resin bound 4-Formylbenzoyl-D-Glu-OtBu

To the above resin bound Fmoc-D-Glu-OtBu was treated with a 20% solution of piperidine in NMP (2×20 mL in 2×5 min), after the resin was drained and washed with NMP (6×20 mL). NMP (10 mL) and diisopropylethylamin (0.96 mL) was added to the resin. 4-formylbenzoic acid (0.841 g, 5.6 mmol) and 1-hydroxybenzotriazole (0.757 g, 5.6 mmol) were dissolved in NMP (10 mL), followed by diispropylcarbodiimide (0.867 mL, 5.6 mmol) and stirred for The for 10 minutes before added to the resin. The mixture was shaken for 2 hours at 25° C. followed by filtration and washing of the resin with N-methyl-2-pyrrolidinone (3×20 mL).

Step 3: Synthesis of resin bound 4-[(2-tertbutoxycarbonylethylamino)-methyl]benzoyl-D-Glu-OtBu The above resin bound 4-Formylbenzoyl-D-Glu-OtBu was treated with tert-Butyl beta-alanine hydrochloride (0.902 g, 5 mmol) and diisopropylamine (0.856 mL, 5 mmol) in a mixture of NMP and trimethylorthoformate (1:1 10 mL) and glacial aceitic acid (1 mL) for 1 hour at 25° C. Sodium cyanoborohydride (314 mg, 5 mmol) was dissolved in a mixture of N-methyl-2-pyrrolidin-one and methanol (1:1, 5 mL) and added. The mixture was vortexed at 25° C. for 4 hours followed by filtration and washing with a mixture of NMP and methanol (1:1, 2×20 mL), NMP (3×20 mL) and a mixture of 1,2-dichloropropane and diisopropylethylamine (7:1, 2×20 mL).

Step 4: Synthesis of resin bound 4-{[(2-tert-butoxy-carbonylethyl)-(15-tert butoxycarbonylpentade-canoyl)-amino]-methyl}benzoyl-D-Glu-OtBu The above resin bound 4-[(2-tertbutoxycarbonylethyl-amino)-methyl]benzoyl-D-Glu-OtBu was added solution of hexadecanedioic acid mono-tert-butyl ester (685 mg, 2 mmol) in NMP, 1,2-dichloropropane, DIPEA (4.5:4.5:1, 10 mL) followed by a solution of bromo-tris-pyrrolidino-phosphonium hexafluorophosphate (PyBrop) (0.93 g, 2 mmoL) dissolved in 1,2-dichloropropane (10 mL). The mixture was vortexed at 50° C. for 3 hours followed by filtration and washing with NMP (4×20 mL) and DCM (10×20 mL).

Step 5: Synthesis of 4-{[(2-tert-butoxycarbonyl-ethyl)-(15-tert butoxycarbonylpentadecanoyl)-amino]-methyl}benzoyl-D-Glu-OtBu

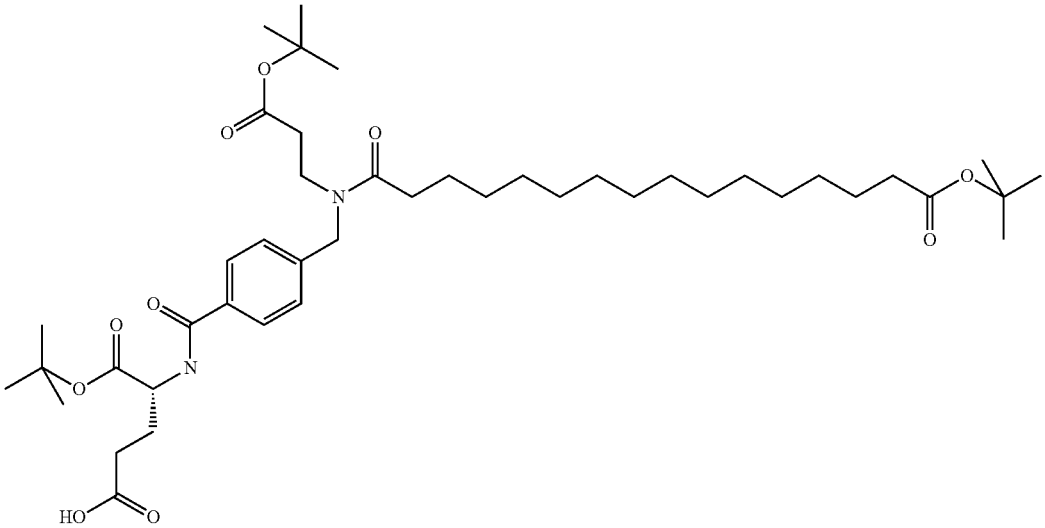

The resin bound 4-{[(2-tert-butoxycarbonylethyl)-(15-tert butoxycarbonylpentadecanoyl)-amino]-methyl}benzoyl-D-Glu-OtBu was treated with DCM containing 1 TFA (2×20 mL, 2×10 min). After filtration the DCM/TFA fraction were collected and washed with $NaHCO_3$ 5% (20 mL). The organic fase was dried (Na2SO4), solvent removed in vacuo and crude material was purified on silicagel column eluted with DCM/EtOH 95:5 to give 4-{[(2-tert-butoxycarbonylethyl)-(15-tert butoxycarbonylpentadecanoyl)-amino]-methyl}benzoyl-D-Glu-OtBu $^1$H-NMR ($CDCl_3$): δ 7.80 (dd, 2H), 7.30-7.08 (m, 3H), 4.72-4.60 (m, 3H), 3.60-3.50 (m, 2H), 2.57-2.40 (m, 5H), 2.37-2.04 (m, 5H), 1.70-1.53 (m, 4H), 1.50 (s, 9H), 1.45 (m, 18H), 1.25 (m, 20H). H PLC-MS (Method 50-99): m/z=811 (M+Na); $R_t$=2.32 min.

Step 6: Synthesis of Synthesis of (R)-2-(4-{[(2-tert-Butoxycarbonyl-ethyl)-(15-tert-butoxycarbonyl-decanoyl)-amino]-methyl}-benzoylamino)-pen-tanedioic acid 1-tert-butyl ester 5-(2,5-dioxopyrrolidin-1-yl) ester

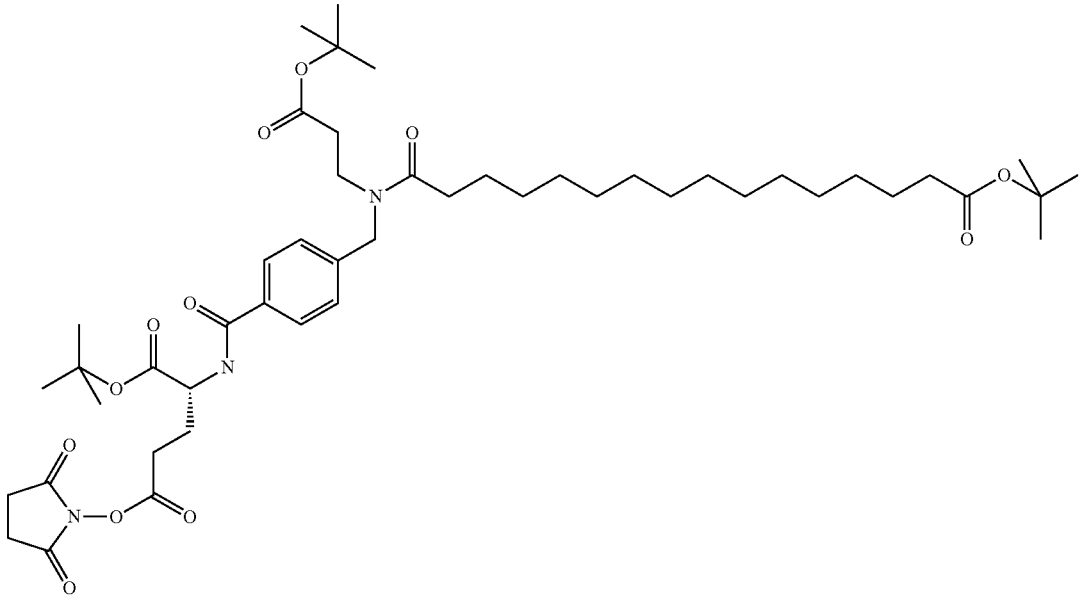

The compound was prepared similar as described in step 3 in general procedure A using (R)-2-{4-[(15-tert-Butoxy-carbonyl-pentadecanoylamino)-methyl]-benzoylamino}-pentanedioic acid 1-tert-butyl ester.

HPLC-MS (Method 50-99): m/z=(908, M+Na); $R_t$=2.37 min.

Step 7: Synthesis of $N^{\epsilon B29}$ (4-{[(2-Carboxy-ethyl)-(15-carboxy-pentadecanoyl)amino]methyl}benzoyl)-γ-D-glutamyl desB30 human insulin

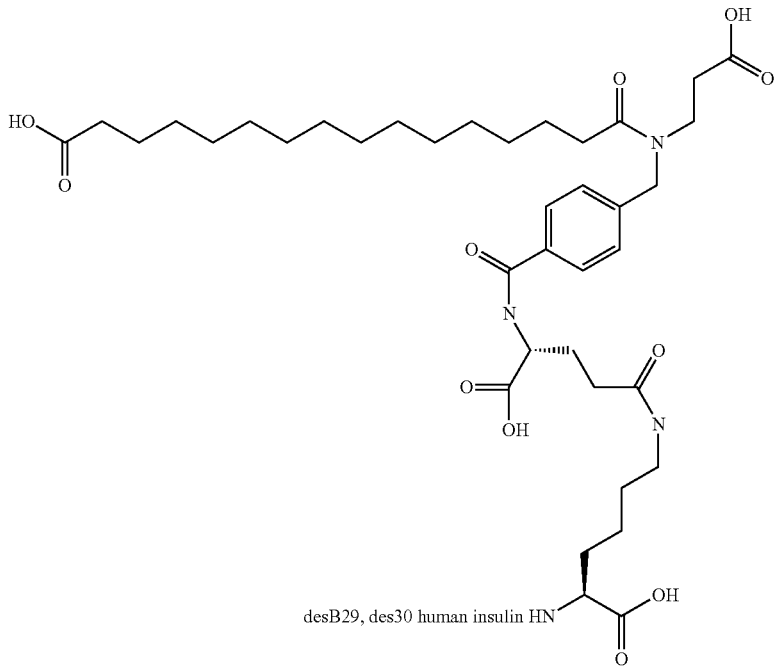

Des-B30 human insulin (386 mg, 0.068 mmol) was dissolved in DMSO (3.5 mL) together with triethylamin (0.094 mL, 0.677 mmol). (R)-2-(4-{[(2-tert-Butoxycarbonyl-ethyl)-(15-tert-butoxycarbonyl-decanoyl)-amino]-methyl}-benzoylamino)-pentanedioic acid 1-tert-butyl ester 5-(2,5-dioxo-pyrrolidin-1-yl) ester (60 mg, 0.068 mmol) was dissolved in THF (1 mL) and added. The mixture was stirred at room temperature for 30 minutes. Cooled on an icebath and dilted with Milli-Q water (7 mL). The pH was adjusted to 5.5 with 1 N HCl, which lead to precipitation. The tube was centrifuged and the solvent was decanted from the solid. The solid was washed once with Milli-Q water (7 mL), and centrifuged again. Solvent was decanted from the solid and to the solid was added TFA (10 mL). The mixture was stirred for 30 minutes and poured into diethylether (35 mL) and centrifuged, after drying in vacuo The crude material was purified Äkta purifier simelar to what has been described above.

HPLC-MS (Method Sciex): m/z=1578 (m/4), 1262 (m/5); $R_1$=3.38 min

Example 20

$N^{\epsilon B29}$-4-{[(2-Carboxyethyl)-(15-carboxypentadecanoyl)amino]methyl}benzoyl)-γ-L-glutamyl desB30 human insulin General Procedure A, Acylation using desB30 Human Insulin Step 1: Synthesis of (S)-2-(4-{[(2-tert-Butoxycarbonyl-ethyl)-(15-tert-butoxycarbonyl-decanoyl)-amino]-methyl}-benzoylamino)-pentanedioic acid 1-tert-butyl ester

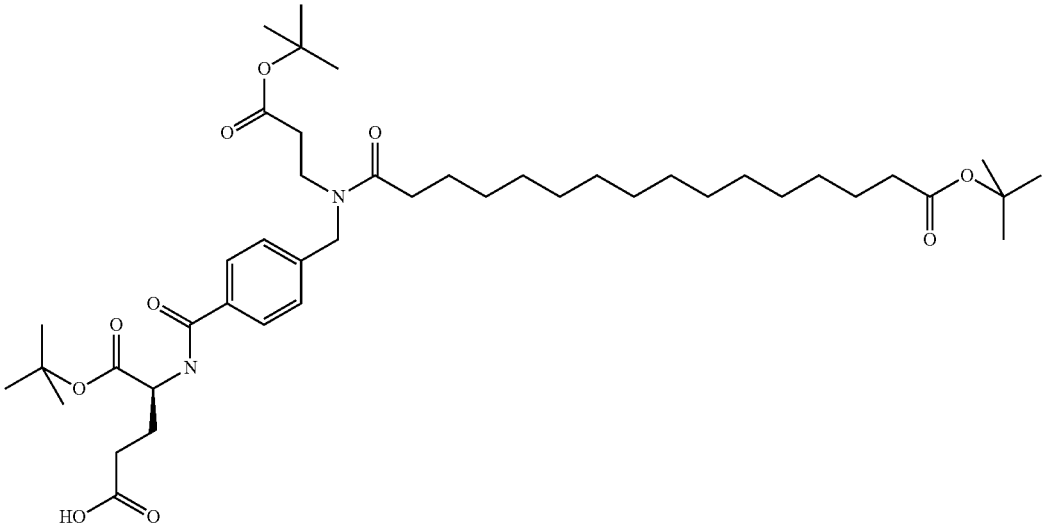

To H-Glu-OtBu, HCl (30.5 mg, 0.128 mmol) in DMF (1 mL) was added DIPEA (0.022 mL, 0.128 mmol), 4-{[(2-tert-Butoxycarbonylethyl)-(15-tert-butoxycarbonyl penta-decanoyl)amino]methyl}benzoic acid 2,5-dioxopyrrolidin-1-yl ester (45 mg, 0.064 mmol) was dissolved in DMF (1 mL) and added. The mixture was stirred under nitrogen at room temperature overnight, separated between ethylacetate and water. The organic phase was dried ($MgSO_4$) and solvent removed in vacuo.

HPLC-MS (Method fast grad): m/z=(789, M+1); $R_1$=2.39 min.

Step 2: Synthesis of (S)-2-(4-{[(2-tert-Butoxycarbonyl-ethyl)-(15-tert-butoxycarbonyl-decanoyl)-amino]-methyl}-benzoylamino)-pentanedioic acid 1-tert-butyl ester 5-(2,5-dioxo-pyrrolidin-1-yl) ester

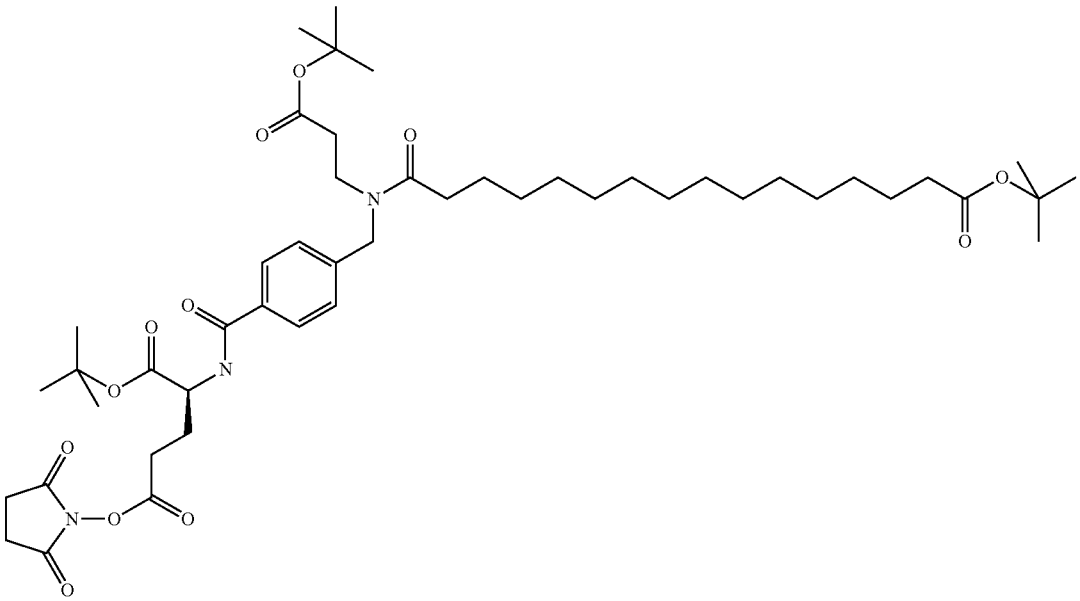

The compound was prepared similar as described in step 3 in general procedure A using (S)-2-{4-[(15-tert-Butoxycarbonyl-pentadecanoylamino)-methyl]-benzoylamino}-pentanedioic acid 1-tert-butyl ester.

HPLC-MS (Method fast grad): m/z=(908, M+Na); $R_t$=2.51 min.

Step 3: Synthesis of $N^{\epsilon B29}$-4-{[(2-Carboxyethyl)-(15-carboxypentadecanoyl)amino]methyl}benzoyl)-γ-L-glutamyl desB30 human insulin

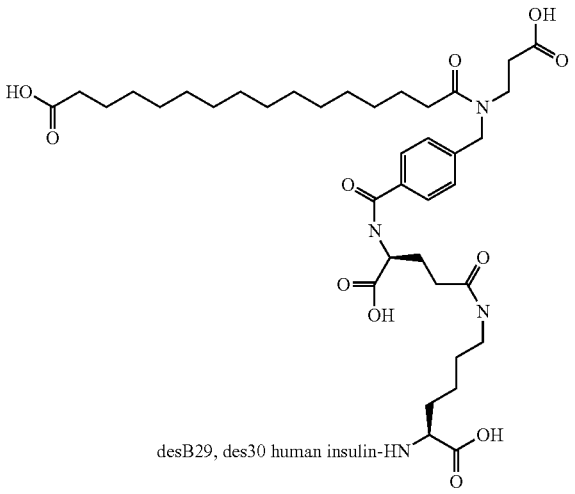

The compound was prepared similar as described in step 4 in general procedure B using (S)-2-(4-{[(2-tert-Butoxycarbonyl-ethyl)-(15-tert-butoxycarbonyl-decanoyl)-amino]-methyl}-benzoylamino)-pentanedioic acid 1-tert-butyl ester 5-(2,5-dioxo-pyrrolidin-1-yl) ester.

Example 21

General Procedure A $N^{\epsilon B29}$-{4-[2-(4-carboxymethylphenyl)ethyl] phenyl}acetyl-γ-L-glutamyl desB30 human insulin Step 1: Synthesis of 2-(2-{4-[2-(4-tert-Butoxycarbonylmethyl-phenyl)-ethyl]-phenyl}-acetylamino)-pentanedioic acid 5-tert-butyl ester 1-(2,5-dioxopyrrolidin-1-yl) ester

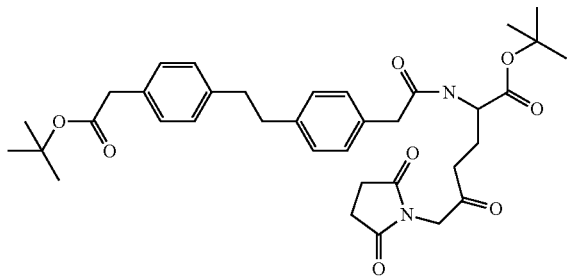

The compound was prepared similar as described in example 11 step 1 to 4 (for tert-butyl hexadecandioyl-L-Glu (OSu)-OtBu) starting from 4,4-dimethylbis(Phenylacetic acid) (purchased from Sigma-Aldrich Library of Rare Chemicals).

Step 2: Synthesis of $N^{\epsilon B29}$-{4-[2-(4-carboxymethyl-phenyl)ethyl]phenyl}acetyl-γ-L-glutamyl desB30 human insulin

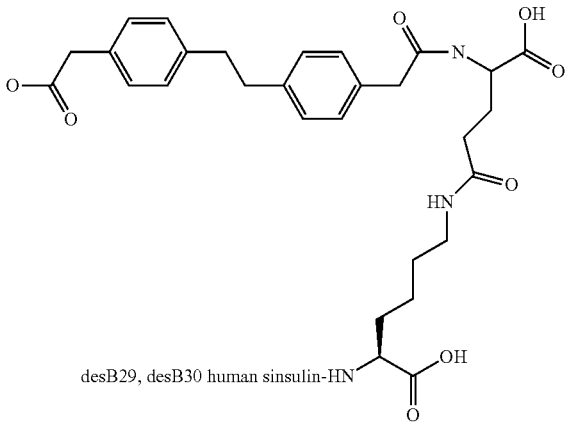

2-(2-{4-[2-(4-tert-Butoxycarbonylmethyl-phenyl)-ethyl]-phenyl}-acetylamino)-pentanedioic acid 5-tert-butyl ester 1-(2,5-dioxo-pyrrolidin-1-yl) ester was reacted with Human des(B30) insulin followed by TFA treatment similar as described in general procedure A. Purification by RP-HPLC was performed on a Gilson 215 system using a SP 250/21 Nucleosil 300-7 C4 column and a water/acetonitrile 30-80% gradient containing 0.1% TFA. Fractions containing product were collected and lyophilized.

MALDI-MS: (SA); m/z: 6117.57. Acidic HPLC: Rt=9.61 min; 98.8% purity. Run time 30 min. Column: C4 5μ 150×4_60 mm "phenomenex, Jupiter". A-Buffer: 0.1% TFA, 99.9% MQ-water, B-buffer: 0.1% TFA, 99.9% Acetonitrile. Flow: 1,5 ml/min. Gradient: 0-17 min, 20-90% B, 17-21 min 90% B, 21-23 min 90-20% B, 23-30 min 20% B. Neutral HPLC: Rt=4.20 min; 99.44% purity. Run time: 30 min. Column: C4 5μ 150×4_60 mm "phenomenex, Jupiter". A-buffer: 10 mM Tris, 15 mM $(NH_4)_2SO_4$, 20% acetonitrile in Mili Q water, pH 7.3 B-buffer: 20.0% MQ-water in acetonitrile. Flow: 1.5 ml/min, 1-20 min: 10-50% B, 20-22 min: 50-60% B, 22-23 min: 60-10% B, 23-30 min 10% B 30-31 min 10% B flow: 0.15 ml/min. 214 nm.

Example 22

$N^{\epsilon B29}$-(3-carboxy-4-hexdecandioylaminobenzoyl) desB30 human insulin

Step 1: 4-Nitro-isophthalic acid

Potassium permanganate (13.07 g) was dissolved in water (80 ml) in a flask fitted with a termometer and a reflux condenser. 4-Nitro-m-xylene (2.23 ml) was added. The mixture was cautiously heated to 85° C. Cooling to maintain the reaction mixtue at 85° C. was not necessarry. After 20 min. the mixture was refluxed gently for 3 h (the purple colour had dissapeared and the mixture was almost black). The warm mixture was filtered through celite. The cold filtrate was acidified with concentrated sulfuric acid and a milky suspention was obtained. Extraction with EtOAc (3×). The combined organic layes was dried ($Na_2SO_4$) and concentrated to give a white crystaline compound. Purification by flash chromatography using EtOAc/Heptane/AcOH 10:10:1 as eluent gave a white crystaline compound in 44% yield (1.55 g).

$^1$H-NMR (DMSO-$d_6$) δ: 8.07 (d, 1H) 8.26 (d, 1H) 8.33 ppm (s, 1H).

Step 2: 3-tert-Butyl 4-Nitro-isophthalate

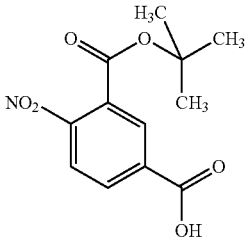

4-Nitro-isophthalic acid (1.0 g) was dissolved in hot toluene (30 ml) and DMF (2 ml). Dimethylformamid-di-t-butyl acetale (3.4 ml) was added dropwise over 1 h min at 100° C. Stirring at 100° C. was continued for 135 min. The cold reaction mixture was concentrated to give a crude mixture of starting material, 4-nitro-isophthalic acid di-tert-butyl ester, 1-tert-butyl 4-nitro-isophthalate and 3-tert-butyl 4-nitroisophthalate. Purification by flash chromatography using EtOAc/Heptane/AcOH 5:15:1 or DCM/AcOH 20:1 resulted in isolation of 3-tert-Butyl 4-Nitro-isophthalate contaminated with 1-tert-Butyl 4-Nitro-isophthalate (10:1). The isomers were determined by NOE-experiments.

$^1$H-NMR ($CDCl_3$) δ: 1.55 (s 9H), 7.89 (d, 1H) 8.32 (d, 1H) 8.49 ppm (s, 1H). HPLC-MS: 268 (M+1).

Step 3: 3-tert-Butyl 4-amino-isophthalate

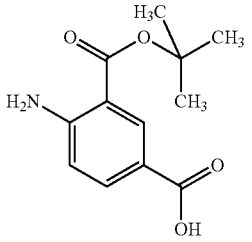

3-tert-Butyl 4-Nitro-isophthalate (100 mg) was dissolved in EtOAc (3 ml) and 10% Pd/C was added. The mixture was hydrogenated at 1 atm for 2 h. The mixture was filtered and concentrated to give the title compound as a white foam in quantitative yield (90 mg).

$^1$H-NMR ($CDCl_3$) δ: 1.60 (s 9H), 6.32 (d, 1H) 7.86 (d, 1H) 8.58 ppm (s, 1H). HPLC-MS: 238 (M+1).

Step 4: 4-(15-tert-Butoxycarbonyl-pentadecanoylamino)-isophthalic acid 3-tert-butyl ester

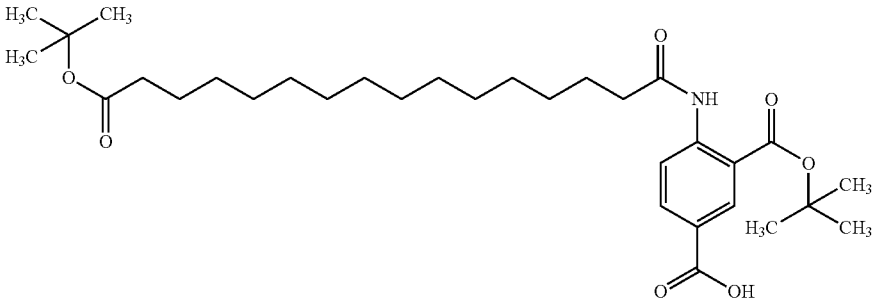

Hexadecanedioic acid mono-t-Bu ester (60 mg) was dissolved in dry THF (1 ml). N,N,N',N'-Tetramethylfluorformamidiniumhexafluorophosphate (46 mg) was added. The mixture was stirred at RT under Nitrogen. A fine precipitate was observed after a while. After 75 min 3-tert-Butyl 4-amino-isophthalate (9:1 mixture, 45 mg) and DIPEA (0.05 ml) was added. After 5 days the mixture was concentrated. The residue was dissolved in EtOAc and extracted with 0.1 M HCl (2×), washed with brine (1×), dried ($Na_2SO_4$) and concentrated to give a sirup, which was purified by flash chromatography using EtOAc/Hept/AcOH 4:16:1 to give the product contaminated with hexadecanedioic acid mono-t-Bu ester 1:4. (63 mg).

HPLC-MS: 562 (M+1).

Step 5: 4-(15-tert-Butoxycarbonyl-pentadecanoylamino)-isophthalic acid 3-tert-butyl ester 1-(2,5-dioxo-pyrrolidin-1-yl) ester

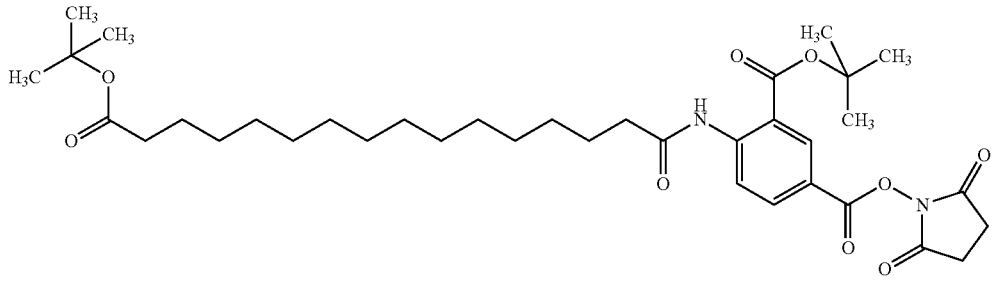

The compound was prepared similar as described in example 1 (general procedure A) step 3 using 4-(15-tert-Butoxycarbonyl-pentadecanoylamino)-isophthalic acid 3-tert-butyl ester instead.

HPLC-MS: 659 (M+1).

Step 6: $N^{\epsilon B29}$-(3-carboxy-4-hexdecandioylaminobenzoyl) desB30 human insulin

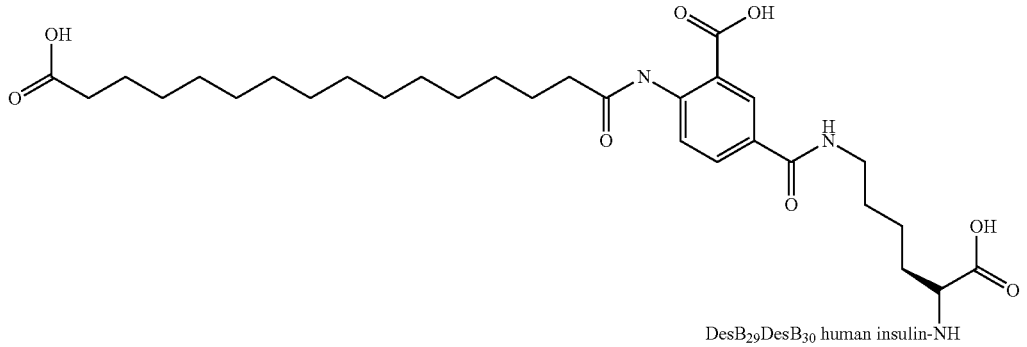

(15-tert-Butoxycarbonyl-pentadecanoylamino)-isophthalic acid 3-tert-butyl ester 1-(2,5-dioxo-pyrrolidin-1-yl) ester was reacted with A1,B1,BOC,BOC-human desB30 insulin followed by TFA treatment similar as described in general procedure B. Purification by RP-HPLC was performed on a Gilson 215 system using a SP 250/21 Nucleosil 300-7 C4 column and a water/acetonitril 20-80% gradient containing 0.1% TFA. Fractions containing product were collected and lyophilized.

MALDI-MS: (SA); m/z: 6140.3. Acidic HPLC: Rt=11.27 min; 83.4% purity. Rub time: 30 min. Column:C4 5μ 150×4_60 mm "phenomenex, Jupiter". A-Buffer: 0.1% TFA, 99.9% MQ-water, B-buffer: 0.1% TFA, 99.9% Acetonitrile. Flow: 1.5 ml/min. Gradient: 0-17 min, 20-90% B, 17-21 min 90% B, 21-23 min 90-20% B, 23-30 min 20% B. Neutral HPLC: Rt=9.10 min; 92.6% purity: Run time: 30 min Column: C4 5μ 150×4_60 mm "phenomenex, Jupiter". A-buffer: 10 mM Tris, 15 mM $(NH_4)_2SO_4$, 20% acetonitrile in Mili Q water, pH 7.3 B-buffer: 20.0% MQ-water in acetonitrile. Flow: 1.5 ml/min 1-20 min: 5% B til 50% B, 20-22 min: 50-60% B, 22-23 min: 60% B til 5% B, 23-30 min 5 til 0% B 30-31 min 0-5% B, flow: 0.15 ml/min. 214 nm.

Example 23

$N^{\epsilon B29}$-10-(4-carboxyphenylsulfanyl)decanoyl-γ-L-glutamyl desB30 human insulin

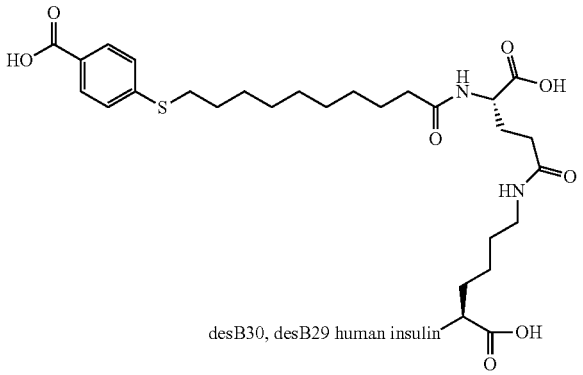

Step 1: 4-(9-Methoxycarbonyl nonylsulfanyl) benzoic acid

4-Mercaptobenzoic acid (2.0 g, 13 mmol) was placed in THF (25 ml). DIEA (3.7 g, 28.5 mmol) was added followed by a solution of methyl 10-bromodecanoate (3.44 g, 13 mmol) in THF (10 ml). After 1 h the solvent was removed under vacuum to yield a slurry, which was stored at rt for 3 days. AcOEt (100 ml) and 1 N HCl (50 ml) were added, but the precipitate did not dissolve very well. Sat. NaCl was added and then methanol in order to aid phase separation. The aqueous phase was removed, and DCM was added to the organic phase, but the precipitates still did not dissolve. The organic phase was concentrated under vacuum and dried with toluene by adding and evaporating twice. Drying under vacuum yielded a white solid (4.4 g, quantitative yield).

HPLC-MS (fast grad) m/z: 361 (M+23), $R_t$=2.34 min.

$^1$H-NMR (DMSO, 300 MHz) δ 12.86 (br, 1H), 7.84 (d, 2H), 7.37 (d, 2H), 3.57 (s, 3H), 3.03 (t, 2H), 2.28 (t, 2H), 1.33-1.69 (m, 6H), 1.24 (s, 8H).

Step 2: 4-(9-Methoxycarbonyl nonylsulfanyl) benzoic acid tert-butyl ester 4-(9-Methoxycarbonyl nonylsulfanyl) benzoic acid (4.4 g, 13 mmol) was suspended in dry toluene (150 ml), under $N_2$. The mixture was refluxed and a solution of N,N-dimethylformamide di-tert-butyl acetal (7.93 g, 39 mmol) in toluene (50 ml) was added over ca. 15 min. After refluxing 16 h, the reaction was allowed to cool and some precipitation occured. TLC (1:2 AcOEt/heptane) indicated ca. 50% completion. The reaction was heated to 70° C. and another portion of N,N-dimethylformamide di-tert-butyl acetal (7.93 g, 39 mmol) in toluene (50 ml) was added over 1.5 h. After stirring an additional hour at 70° C., the sample was concentrated under vacuum to yield an brown oil. Purification by flash chromatography (15 cm×40 mm dia., 1:2 AcOEt/heptane) yielded a yellow oil (3.65 g, 71%)

HPLC-MS (fast grad) m/z: 417 (M+23), $R_t$=3.03 min.

$^1$H-NMR ($CDCl_3$, 300 MHz) δ 7.88 (d, 2H), 7.26 (d, 2H), 3.66 (s, 3H), 2.96 (t, 2H), 2.30 (t, 2H), 1.60-1.75 (m, 4H), 1.59 (s, 9H), 1.43 (t-br, 2H), 1.29 (s, 8H).

Step 3: 4-(9-Carboxynonylsulfanyl) benzoic acid tert-butyl ester 4-(9-Methoxycarbonyl nonylsulfanyl) benzoic acid tert-butyl ester (2.46 g, 6.2 mmol) was dissolved in THF (25 ml). 1 N NaOH (6.2 ml, 6.2 mmol) was added and the mixture was stirred under $N_2$ for 1 d. 1 N HCl (6.5 ml) diluted with water (100 ml) was added, and then AcOEt (100 ml) was added. The organic phase was dried over $MgSO_4$ and concentrated under vacuum to yield a white solid (2.5 g).

HPLC-MS (fast grad) m/z: 403 (M+23), $R_t$=2.69 min.

$^1$H-NMR (DMSO, 300 MHz) δ 11.99 (br, 1H), 7.79 (d, 2H), 7.36 (d, 2H), 3.03 (t, 2H), 2.18 (t, 2H), 1.60 (m, 2H), 1.53 (s, 9H), 1.32-1.51 (m, 4H), 1.24 (s, 8H).

Step 4: (S)-2-[10-(4-tert-Butoxycarbonylphenylsulfanyl) decanoylamino]pentanedioic acid 5-benzyl ester 1-tert-butyl ester4-(9-Carboxynonylsulfanyl) benzoic acid tert-butyl ester (1 g, 2.6 mmol) was dissolved in THF (10 ml), EDAC (0.53 g, 2.8 mmol), HOBt (0.39 g, 2.9 mmol) and DIEA (1.0 g, 7.8 mmol) were added. The solution was stirred under $N_2$. A precipitate formed, and DMF (10 ml) was added and a clear solution was obtained. After stirring at rt for 30 min, H-Glu (OBzl)-OtBu (0.87 g, 2.6 mmol) was added. The solution was stirred under $N_2$ for 16 h at rt. The sample was concentrated under vacuum. AcOEt (100 ml) was added, and the solution was washed with water (50 ml), and 0.2 M HCl (2×50 ml), and dried over $MgSO_4$, and concentrated under vacuum to yield a light oil. Purification by flash chromatography (15 cm×40 mm dia., 1:2 AcOEt/heptane) yielded a colorless oil (401+525 mg, 54% yield).

HPLC-MS (50-99) m/z: 656 (M+1), $R_t$=2.44 min.

$^1$H-NMR ($CDCl_3$, 300 MHz) δ 7.87 (d, 2H), 7.35 (s, 5H), 7.25 (d, 2H), 6.07 (d, 1H), 4.52 (m, 1H), 2.95 (t, 2H), 2.31-2.35 (m, 2H), 2.11-2.27 (m, 3H), 1.88-2.03 (m, 1H), 1.53-1.71 (m, 13H), 1.46 (s, 9H), 1.42 (m, 2H), 1.28 (m, 8H).

Step 5: (S)-2-[10-(4-tert-Butoxycarbonylphenylsulfanyl) decanoylamino]pentanedioic acid 1-tert-butyl ester(S)-2-[10-(4-tert-Butoxycarbonylphenylsulfanyl)decanoylamino] pentanedioic acid 5-benzyl ester 1-tert-butyl ester (385 mg, 0.587 mmol) was dissolved in THF. 1 N NaOH (587 μl, 0.587 mmol) was added and the solution was stirred for 16 h at rt under $N_2$. The solvent had evaporated, so more THF (3 ml) was added. AcOEt (40 ml) and dilute HCl (1 ml 1N HCl in 25 ml water) was added. The phases were separated and the aqueous phase was extracted with AcOEt (15 ml). The organic phases were pooled and washed with sat. NaCl, dried over $MgSO_4$. The solution was concentrated under vacuum to yield a light brown oil. The oil was purified by flash chromatography (7.5 cm×40 mm dia., 20:20:1 AcOEt/heptane/AcOH) and after concentrating the appropriate fractions under vacuum, toluene was added and removed under vacuum a few times to remove residual AcOH to yield a colorless oil (160 mg, 48% yield).

HPLC-MS (50-99) m/z: 566 (M+1), $R_t$=1.65 min.

$^1$H-NMR ($CDCl_3$, 300 MHz) δ 7.87 (d, 2H), 7.26 (d, 2H), 6.25 (d, 1H), 4.52 (m, 1H), 2.96 (t, 2H), 2.38-2.47 (m, 2H), 2.12-2.30 (m, 3H), 1.82-1.99 (m, 1H), 1.60-1.75 (m, 4H), 1.58 (s, 9H), 1.47 (s, 9H), 1.36-1.45 (m, 2H), 1.28 (s, 8H).

Step 6: (S)-2-[10-(4-tert-Butoxycarbonylphenylsulfanyl) decanoylamino]pentanedioic acid 5-tert-butyl ester 1-(2,5-dioxopyrrolidin-1-yll) ester(S)-2-[10-(4-tert-Butoxycarbonylphenylsulfanyl)decanoylamino]pentanedioic acid 1-tert-butyl ester (156 mg, 0.276 mmol) was dissolved in THF (3 ml). DIEA (47 μl, 0.276 mmol) was added and the solution was cooled to 0° C. TSTU (99 mg, 0.276 mmol) was added and the solution was stirred under nitrogen at 0° C. for 30 min, and then at rt for 16 h. The sample was concentrated under vacuum and partitioned between AcOEt and 0.2 N HCl. The organic phase was dried over $MgSO_4$ and concentrated under vacuum to yield a residue (194 mg).

HPLC-MS (50-99) m/z: 686 (M+23), $R_t$=1.46 min.

$^1$H-NMR (DMSO, 400 MHz) δ 8.12 (d, 1H), 7.79 (d, 2H), 7.36 (d, 2H), 4.16 (m, 1H), 3.03 (t, 2H), 2.81 (s, 4H), 2.61-2.78 (m, 4H), 2.10 (t, 2H), 1.99-2.07 (m, 1H), 1.80-1.94 (m, 1H), 1.42-1.66 (m, 11H), 1.38 (s, 9H), 1.24 (s, 8H). (singlet at 2.69, ca. 2H possible impurity).

Step 7: $N^{\epsilon B29}$-10-(4-carboxyphenylsulfanyl)decanoyl-γ-L-glutamyl desB30 human insulin General Coupling and Deprotection Method A:

Des-B30 insulin (125 mg, 0.022 mmol) was dissolved by adding 100 mM $Na_2CO_3$ (1.5 ml) and acetonitrile (1.5 ml) in a 10 ml round bottom-flask. (S)-2-[10-(4-tert-Butoxycarbonylphenylsulfanyl)decanoylamino]pentanedioic acid 5-tert-butyl ester 1-(2,5-dioxopyrrolidin-1-yll) ester (14.5 mg, 0.022 mmol) was added in acetonitrile (750 ul) and $Na_2CO_3$ (750 ul) was added so the final solution was 50:50 100 mM $Na_2CO_3$/acetonitrile. The solution was stirred at rt for 1 h. The solution was transferred to a 15 ml centrifuge tube, washing with Milli-Q water (6 ml). The solution was cooled on ice, and the pH was adjusted to 5.1 by adding 1N HCl, which lead to precipitation. The tube was centrifuged at 5000 rpm for 10 min at 10° C. The solvent was decanted from the solid. 95:5 TFA/water (2.5 ml) was added to the solid. The solution was poured into a flask, washing with more 95:5 TFA/water (2.5 ml). The solution was stirred for 30 min at rt, and concentrated under vacuum. DCM was added and removed twice, and the flask was dried under vacuum at rt. The product was purified by preparative HPLC (2 cm dia. $C_{18}$ column, acetonitrile/water/0.05% TFA). The relevant fractions were pooled (two batches) and diluted 1:1 with water. The solutions were cooled on ice, and precipitation was induced by adjusting the pH to ca. 5 with 1 N NaOH. The samples were centrifuged (5000 rpm, 10 min, 5° C.). The liquid was decanted off and the pellets were lyophilized to yield a white solid (30 mg+5 mg).

HPLC-MS (Sciex) m/z: 1536.7 (M/4+1=1536.5), $R_t$=3.2 min.

HPLC (neutral) $R_t$=5.60 min.

Example 24

$N^{\epsilon B29}$-11-(4-carboxyphenylsulfanyl)undecanoyl-γ-L-glutamyl desB30 human insulin

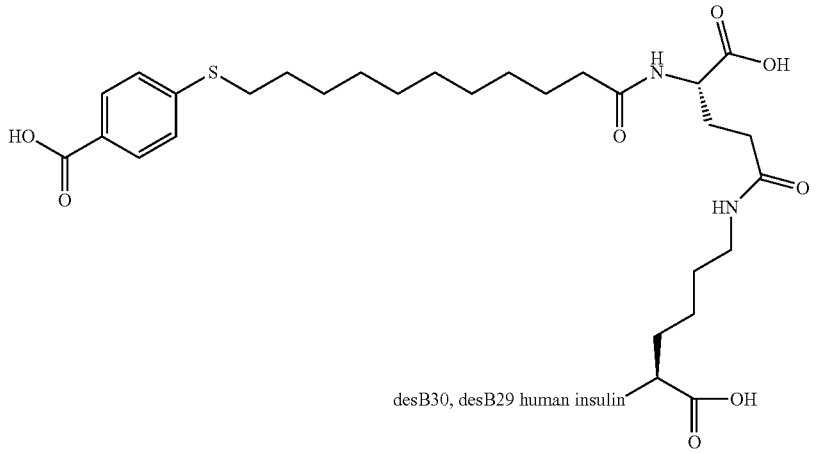

The following steps in the synthesis of $N^{\epsilon B29}$-11-(4-carboxyphenylsulfanyl)undecanoyl-γ-L-glutamyl desB30 human insulin were performed in a similar fashion as those described for $N^{\epsilon B29}$-10-(4-carboxyphenylsulfanyl)decanoyl-γ-L-glutamyl desB30 human insulin.

Step 1:
4-(10-Methoxycarbonyldecylsulfanyl)benzoic acid

HPLC-MS (fast grad) m/z: 375 (M+23), $R_t$=2.44 min.

$^1$H-NMR (DMSO, 300 MHz) δ 12.85 (br, 1H), 7.83 (d, 2H), 7.36 (d, 2H), 3.57 (s, 3H), 3.03 (t, 2H), 2.28 (t, 2H), 1.60 (m, 2H), 1.58 (m, 2H), 1.40 (m, 2H), 1.23 (s, 10H).

Step 2:
4-(10-Methoxycarbonyldecylsulfanyl)benzoic acid tert-butyl ester $^1$H-NMR ($CDCl_3$, 300 MHz) δ 7.87 (d, 2H), 7.26 (d, 2H), 3.67 (s, 3H), 2.96 (t, 2H), 2.30 (t, 2H), 1.57-1.75 (m, 13H), 1.45 (m, 2H), 1.28 (s, 10H).

Step 3: 4-(10-Carboxydecylsulfanyl)benzoic acid tert-butyl ester

HPLC-MS (50-99) m/z: 417 (M+23), $R_t$=1.82 min.

$^1$H-NMR ($CDCl_3$, 300 MHz) δ 7.87 (d, 2H), 7.26 (d, 2H), 2.96 (t, 2H), 2.35 (t, 2H), 1.55-1.74 (m, 13H), 1.43 (m, 2H), 1.28 (s, 10H).

Step 4: (S)-2-[11-(4-tert-Butoxycarbonylphenylsulfanyl)undecanoylamino]pentanedioic acid 5-benzyl ester 1-tert-butyl ester $^1$H-NMR ($CDCl_3$, 300 MHz) δ 7.86 (d, 2H), 7.35 (s, 5H), 7.26 (d, 2H), 6.06 (d, 1H), 5.11 (s, 2H), 4.52 (m, 1H), 2.96 (t, 2H), 2.39 (m, 2H), 2.11-2.28 (m, 3H), 1.88-2.06 (m, 1H), 1.60-1.73 (m, 4H), 1.58 (s, 9H), 1.46 (s, 9H), 1.35-1.43 (m, 2H), 1.26 (s, 10H).

Step 5: (S)-2-[11-(4-tert-Butoxycarbonylphenylsulfanyl)undecanoylamino]pentanedioic acid 1-tert-butyl ester HPLC-MS (50-99) m/z: 602 (M+23), $R_t$=1.80 min.

$^1$H-NMR ($CDCl_3$, 400 MHz) δ 7.87 (d, 2H), 7.26 (d, 2H), 6.25 (d, 1H), 4.52 (m, 1H), 2.96 (t, 2H), 2.40 (m, 2H), 2.14-2.31 (m, 3H), 1.80-1.98 (m, 1H), 1.60-1.75 (m, 4H), 1.58 (s, 9H), 1.47 (s, 9H), 1.36-1.45 (m, 2H), 1.26 (s, 10H).

Step 6: (S)-2-[11-(4-tert-Butoxycarbonylphenylsulfanyl)undecanoylamino]pentanedioic acid 5-tert-butyl ester 1-(2,5-dioxo-pyrrolidin-1-yl) ester HPLC-MS (50-99) m/z: 699 (M+23), R=2.05 min.

$^1$H-NMR ($CDCl_3$, 400 MHz) δ 7.87 (d, 2H), 7.26 (d, 2H), 6.19 (d, 1H), 4.60 (m, 1H), 2.96 (t, 2H), 2.84 (s, 4H), 2.68-2.78 (m, 1H), 2.56-2.67 (m, 1H), 2.27-2.39 (m, 1H), 2.22 (t, 2H), 2.01-2.14 (m, 1H), 1.59-1.75 (m, 4H), 1.58 (s, 9H), 1.48 (s, 9H), 1.37-1.46 (m, 2H), 1.28 (s, 10H).

Step 7:
B29N(eps)-11-(4-carboxy-phenylsulfanyl)undecanoyl gamma-Glu desB30 insulin HPLC-MS (Sciex) m/z: 1539.8 (M/4+1=1540) Rt: 3.5 min.

HPLC (neutral) $R_t$=5.93.

Example 25

$N^{\epsilon B29}$-10-(4-Carboxyphenoxy)decanoyl beta-Asp desB30 insulin

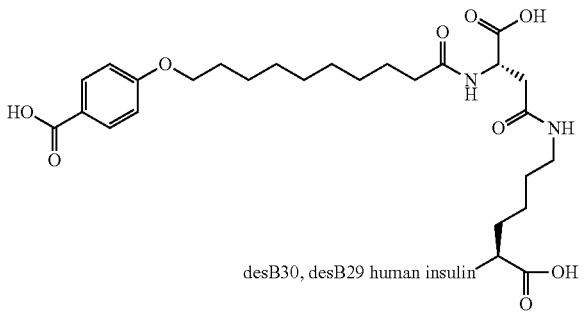

Step 1: 4-(9-Methoxycarbonylnonyloxy)benzoic acid tert-butyl ester 4-Hydroxybenzoic acid tert-butyl ester (500 mg, 2.57 mmol) and 10-bromodecanoic acid methyl ester (683 mg, 2.57 mmol) were dissolved in acetonitrile, and $K_2CO_3$ was added. The mixture was refluxed under nitrogen for 16 h. The solids were filtered off, and the filtrate was concentrated under vacuum. The residue was dissolved in AcOEt (50 ml) and water (25 ml). The phases were separated and the organic phase was dried over $MgSO_4$ and concentrated to yield a colorless oil (874 mg, 90% yield).

HPLC-MS (50-99) m/z: 402 (M+23), $R_t$=1.65 min.

$^1$H-NMR ($CDCl_3$, 400 MHz) δ7.92 (d, 2H), 6.87 (d, 2H), 3.99 (t, 2H), 3.67 (s, 3H), 2.31 (t, 2H), 1.78 (m, 2H), 1.62 (m, 2H), 1.58 (s, 9H), 1.45 (m, 2H), 1.31 (s, 8H).

Step 2: 4-(9-Carboxynonyloxy)benzoic acid tert-butyl ester4-(9-Methoxycarbonylnonyloxy)benzoic acid tert-butyl ester (858 mg, 2.27 mmol) was dissolved in THF (5 ml). 1 N NaOH (2.27 ml) was added and the mixture was covered lightly with a rubber septum, and stirred for 16 h at rt. AcOEt (40 ml) and 1.05 eq 1N HCl in water (25 ml) were added. The phases were separated, and the organic phase was dried over $MgSO_4$, and concentrated under vacuum to yield a white solid (781 mg, 95% yield).

HPLC-MS (50-99) m/z: 387 (M+23), $R_t$=1.46 min.

$^1$H-NMR ($CDCl_3$, 400 MHz) δ 7.92 (d, 2H), 6.87 (d, 2H), 3.99 (t, 2H), 2.35 (t, 2H), 1.75 (m, 2H), 1.64 (m, 2H), 1.58 (s, 9H), 1.45 (m, 2H), 1.32 (s, 8H).

Step 3: 4-[9-(2,5-Dioxopyrrolidin-1-yloxycarbonyl)nonyloxy]benzoic acid tert-butyl ester4-(9-Carboxynonyloxy) benzoic acid tert-butyl ester (779 mg, 2.14 mmol) was dissolved in THF (15 ml), and DIEA (366 μl, 2.14 mmol) was added. The solution was cooled to 0° C., and placed under nitrogen. TSTU (768 mg, 2.14 mmol) was added. The solution was stirred at 0° C. for 30 min then at rt for 16 h. The sample was concentrated under vacuum. AcOEt (40 ml) was added, and the solution was washed with 0.2 N HCl (2×25 ml), dried over $MgSO_4$, and concentrated under vacuum to yield a yellowish solid. The solid was recrystallized from AcOEt to yield a white powder (276 mg, 28%).

HPLC-MS (50-99) m/z: 484 (M+23), $R_t$=1.71 min.

$^1$H-NMR ($CDCl_3$, 400 MHz) δ 7.92 (d, 2H), 6.87 (d, 2H), 3.99 (t, 2H), 2.83 (s, 4H), 2.61 (t, 2H), 1.67-1.88 (m, 4H), 1.58 (s, 9H), 1.27-1.52 (m, 10H).

Step 4: (S)-2-[10-(4-tert-butoxycarbonylphenoxy)decanoylamino]succinic acid 1-tert-butyl ester4-[9-(2,5-Dioxopyrrolidin-1-yloxycarbonyl)nonyloxy]benzoic acid tert-butyl ester (264 mg, 0.57 mmol) was dissolved in DMF (2.5 ml). H-Asp-OtBu was added, and more DMF (2.5 ml). After 1 h DIEA (1 eq., 98 ul) was added, and after 30 min more, DMF (5 ml) was added. There was still a lot of undissolved solids. After 1 d at rt the solvent was removed under vacuum. AcOEt (40 ml) was added and the solution was washed with 0.2 N HCl (2×25 ml), dried over $MgSO_4$ and concentrated under vacuum to yield an opaque oil (283 mg, 92% yield).

HPLC-MS (50-99) m/z: 558 (M+23), $R_t$=1.57 min.

$^1$H-NMR (DMSO, 300 MHz) δ 12.40 (br, 1H), 8.14 (d, 1H), 7.82, (d, 2H), 6.99 (d, 2H), 4.44 (q, 1H), 4.02 (t, 2H), 2.52-2.92 (m, 2H), 2.08 (t, 2H), 1.71 (t, 2H), 1.20-1.55 (m, 28H).

Step 5: (S)-2-[10-(4-tert-Butoxycarbonylphenoxy)decanoylamino]succinic acid 4-tert-butyl ester 1-(2,5-dioxopyrrolidin-1-yl) ester(S)-2-[10-(4-tert-butoxycarbonylphenoxy)decanoylamino] succinic acid 1-tert-butyl ester (261 mg, 0.49 mmol) was dissolved in THF (5 ml). The solution was cooled to 0° C., and DIEA (100 μl, 0.59 mmol) and TSTU (175 mg, 0.49 mmol) were added. The mixture was stirred for 16 h in a small ice bath, such that it could warm to RT after ca. 1 h. The sample was concentrated under vacuum. AcOEt (40 ml) was added, and the solution was washed with 0.2 N HCl (2×25 ml), dried over $MgSO_4$, and concentrated under vacuum to yield a colorless oil containing some white solid. The product was purified by flash chromatography (35 g silica, 400 ml 1:1 AcOEt/heptane and 100 ml 7:3 AcOEt/heptane) to yield a white solid (200 mg, 65% yield).

HPLC-MS (Sciex) m/z: 633 (M+1), $R_t$=6.09 min.

$^1$H-NMR ($CDCl_3$, 300 MHz) δ 7.91 (d, 2H), 6.87 (d, 2H), 6.51 (d, 1H), 4.83 (m, 1H), 3.99 (t, 2H), 3.24 (m, 2H), 2.83 (s, 4H), 2.25 (t, 2H), 1.78 (m, 2H), 1.62-1.70 (m, 2H), 1.58 (s, 9H), 1.47 (s, 9H), 1.36-1.46 (m, 2H), 1.31 (s, 8H).

Step 6: $N^{\epsilon B29}$-10-(4-Carboxyphenoxy)decanoyl beta-Asp desB30 insulin The compound was prepared using the General Coupling and Deprotection Method A to yield a white solid (26 mg and 8 mg).

HPLC-MS (Sciex) m/z: 1529.3 (M/4+1=1529), Rt=3.4 min.

HPLC (neutral) $R_t$=5.31 min.

Example 26

$N^{\epsilon B29}$-11-(4-Carboxy-phenoxy) undecanoyl γ-L-glutamyl desB30 insulin

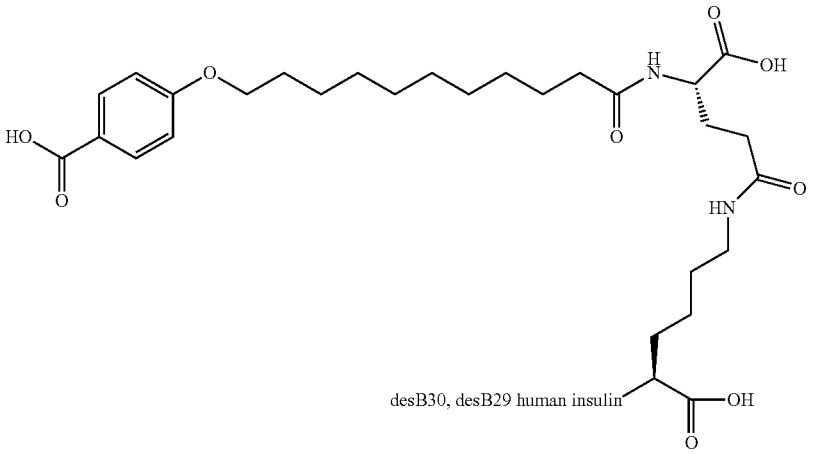

The following steps in the synthesis of $N^{\epsilon B29}$-11-(4-Carboxyphenoxy) undecanoyl γ-L-glutamyl desB30 insulin were performed in a similar fashion as those described for $N^{\epsilon B29}$-10-(4-Carboxyphenoxy)decanoyl beta-Asp desB30 insulin.

Step 1: 4-(10-Methoxycarbonyldecyloxy)benzoic acid tert-butyl ester

HPLC-MS (50-99) m/z: 415 (M+23), $R_t$=2.31 min.

$^1$H-NMR ($CDCl_3$, 300 MHz) δ 7.92 (d, 2H), 6.87 (d, 2H), 3.99 (t, 2H), 3.67 (s, 2.30 (t, 2H), 1.79 (m, 2H), 1.62 (m, 2H), 1.58 (s, 9H), 1.43 (m, 2H), 1.30 (s, 10H).

Step 2: 4-(10-Carboxydecyloxy)benzoic acid tert-butyl ester

HPLC-MS (fast grad) m/z: 401 (M+23), $R_t$=2.71 min.

$^1$H-NMR ($CDCl_3$, 300 MHz) δ 7.92 (d, 2H), 6.87 (d, 2H), 3.98 (t, 2H), 2.34 (t, 2H), 1.78 (m, 2H), 1.62 (m, 2H), 1.58 (s, 9H), 1.44 (m, 2H), 1.30 (s, 10H).

Step 3: 4-[10-(2,5-Dioxopyrrolidin-1-yloxycarbonyl)decyloxy]benzoic acid tert-butyl ester HPLC-MS (50-99) m/z: 498 (M+23), $R_t$=1.89 min.

$^1$H-NMR ($CDCl_3$, 400 MHz) δ 7.92 (d, 2H), 6.88 (d, 2H), 3.99 (t, 2H), 2.84 (s, 4H), 2.60 (t, 2H), 1.66-1.90 (m, 4H), 1.58 (s, 9H), 1.43 (m, 2H), 1.32 (s, 10H).

Step 4: (S)-2-[11-(4-tert-Butoxycarbonylphenoxy) undecanoylamino]pentanedioic acid 1-tert-butyl ester HPLC-MS (50-99) m/z: 564 (M+1), $R_t$=1.68 min.

$^1$H-NMR ($CDCl_3$, 400 MHz) δ 7.92 (d, 2H), 6.87 (d, 2H), 4.50 (br, 1H), 3.98 (t, 2H), 2.38 (br, 2H), 2.24 (t, 2H), 2.04-2.20 (br, 1H), 1.82-1.98 (br, 1H), 1.69-1.82 (m, 2H), 1.59-1.67 (m, 2H), 1.57 (s, 9H), 1.38-1.50 (m, 11H), 1.29 (s, 10H).

Step 5: (S)-2-[11-(4-tert-Butoxycarbonylphenoxy) undecanoylamino]pentanedioic acid 1-tert-butyl ester 5-(2,5-dioxopyrrolidin-1-yl) ester HPLC-MS (50-99) m/z: 683 (M+23), $R_t$=1.91 min.

$^1$H-NMR ($CDCl_3$, 300 MHz) δ 7.92 (d, 2H), 6.87 (d, 2H), 6.20 (d, 1H), 4.60 (m, 1H), 3.99 (t, 2H), 2.84 (s, 4H), 2.54-2.80 (m, 2H), 2.26-2.42 (m, 1H), 2.22 (t, 2H), 2.04-2.15 (m, 1H), 1.72-1.88 (m, 2H), 1.60-1.70 (m, 2H), 1.58 (s, 9H), 1.48 (s, 9H), 1.39-1.46 (m, 2H), 1.30 (s, 10H).

Step 6: $N^{\epsilon B29}$-11-(4-Carboxy-phenoxy)undecanoyl γ-L-glutamyl desB30 insulin HPLC-MS (Sciex) m/z: 1536.4 (M/4+1=1536.0), $R_t$=3.92 min.

HPLC (neutral) $R_t$=5.18 min.

Example 27

Insulin Receptor Binding of the Insulin Derivatives of the Invention

The affinity of the insulin derivatives of the invention for the human insulin receptor was determined by a SPA assay (Scintillation Proximity Assay) microtiterplate antibody capture assay. SPA-PVT antibody-binding beads, anti-mouse reagent (Amersham Biosciences, Cat No. PRNQ0017) were mixed with 25 ml of binding buffer (100 mM HEPES pH 7.8; 100 mM sodium chloride, 10 mM $MgSO_4$, 0.025% Tween-20). Reagent mix for a single Packard Optiplate (Packard No. 6005190) is composed of 2.4 μl of a 1:5000 diluted purified recombinant human insulin receptor—exon 11, an amount of a stock solution of A14 Tyr[$^{125}$I]-human insulin corresponding to 5000 cpm per 100 μl of reagent mix, 12 μl of a 1:1000 dilution of F12 antibody, 3 ml of SPA-beads and binding buffer to a total of 12 ml. A total of 100 μl was then added and a dilution series is made from appropriate samples. To the dilution series was then added 100 μl of reagent mix and the samples were incubated for 16 hours while gently shaken. The phases were the then separated by centrifugation for 1 min and the plates counted in a Topcounter. The binding data were fitted using the nonlinear regression algorithm in the GraphPad Prism 2.01 (GraphPad Software, San Diego, Calif.).

| Product | Receptor binding (% of human insulin) |
|---|---|
| Human insulin | 100 |
| $N^{\epsilon B29}$—[N—(HOOC($CH_2$)$_{14}$CO)—N-(carboxyethyl)-$CH_2$-para-$C_6H_4$CO] desB30 human insulin | 18 |
| $N^{\epsilon B29}$—[N—(HOOC($CH_2$)$_{13}$CO)—N-(carboxyethyl)-$CH_2$-para-$C_6H_4$CO] desB30 human insulin | 28 |
| $N^{\epsilon B29}$—[N—(HOOC($CH_2$)$_{14}$CO)—N-(carboxymethyl)-para-$C_6H_4$CO] desB30 human insulin | 17 |
| $N^{\epsilon B29}$—[N—(HOOC($CH_2$)$_{14}$CO)—N-(carboxyethyl)-$CH_2$-ortho-$C_6H_4$CO] desB30 human insulin | 11 |
| $N^{\epsilon B29}$—[N—(HOOC($CH_2$)$_{14}$CO)-γ-Glutamyl-N—$CH_2$-para-$C_6H_4$CO] desB30 human insulin | 14 |
| $N^{\epsilon B29}$-(3-Carboxy-5-hexadecandioylamino-benzoyl)desB30 insulin | 12 |
| $N^{\epsilon B29}$—[N—(HOOC($CH_2$)$_{16}$CO)—N-(carboxyethyl)-$CH_2$-para-$C_6H_4$CO] desB30 human insulin | 15 |
| $N^{\epsilon B29}$- [(5-{[(2-Carboxyethyl)- (15-carboxypentadecanoyl)amino]methyl}furan-2-carbonyl)desB30 human insulin | 13 |
| $N^{\epsilon B29}$-(3-Carboxy-5-octadecandioylamino-benzoyl) des(B30) human insulin | 19 |
| $N^{\epsilon B29}$-{4-Carboxy-4-[10-(4-carboxy-phenoxy)-decanoylamino]-butyryl}desB30 human insulin | 46 |
| $N^{\epsilon B29}$-10-(4-carboxy-phenylsulfanyl) decanoyl-γ-L-glutamyl desB30 insulin | 101 |
| $N^{\epsilon B29}$-10-(4-Carboxyphenoxy) decanoyl beta-Asp desB30 insulin | 42 |
| $N^{\epsilon B29}$-11-(4-Carboxy-phenoxy) tuldecanoyl-γ-L-glutamyl desB30 insulin | 55 |

Example 28

Preparation of Monoclonal mIR Antibodies

Specific antibodies (F12) were produced by monoclonal technique: RBF mice were immunized by injecting 50 μg of purified mIR in FCA subcutaneously followed by two injections with 20 μg of mIR in FIA. Highresponder mice were boosted intravenously with 25 μg of mIR and the spleens were harvested after 3 days. Spleen cells were fused with the myeloma Fox cell line (Köhler, G & Milstein C. (1976), European J. Immunology, 6:511-19; Taggart R T et al (1983), Science 219:1228-30). Supernatants were screened for antibody production in a mIR specific ELISA. Positive wells were cloned and tested in Western blotting.

Example 29

Hydrophobicity Data on Insulin Derivatives According to the Invention

The hydrophobicity (hydrophobic index) of the insulin derivatives of the invention relative to human insulin, $k'_{rel}$, were measured on a LiChrosorb RP18 (5 μm, 250×4 mm) HPLC column by isocratic elution at 40° C. using mixtures of A) 0.1 M sodium phosphate buffer, pH 7.3, containing 10% acetonitrile, and B) 50% acetonitrile in water as eluents. The elution was monitored by following the UV absorption of the eluate at 214 nm. Void time, $t_0$, was found by injecting 0.1 mM sodium nitrate. Retention time for human insulin, $t_{human}$, was adjusted to at least $2t_0$ by varying the ratio between the A and B solutions. $k'_{rel}=(t_{denvative}-t_0)/(t_{human}-t_0)$. $k'_{rel}$. found for a number of insulin derivatives according to the invention.

Data on receptor binding and hydrophobicity data of insulin derivatives according to the present invention are shown in the following tables:

| Insulin derivative | $k'_{rel}$ |
|---|---|
| $N^{\epsilon B29}$—[N—(HOOC($CH_2$)$_{14}$CO)—N-(carboxyethyl)-$CH_2$-para-$C_6H_4$CO] desB30 human insulin | 1.19 |
| $N^{\epsilon B29}$—[N—(HOOC($CH_2$)$_{13}$CO)—N-(carboxyethyl)-$CH_2$-para-$C_6H_4$CO] desB30 human insulin | 0.81 |
| $N^{\epsilon B29}$—[N—(HOOC($CH_2$)$_{14}$CO)—N-(carboxymethyl)-para-$C_6H_4$CO] desB30 human insulin | 1.08 |
| $N^{\epsilon B29}$—[N—(HOOC($CH_2$)$_{14}$CO)-γ-Glu-N-$CH_2$-para-$C_6H_4$CO] desB30 human insulin | 1.12 |
| $N^{\epsilon B29}$-(3-Carboxy-5-hexadecandioylamino-benzoyl)desB30 insulin | 1.7 |
| $N^{\epsilon B29}$—[N—(HOOC($CH_2$)$_{15}$CO)—N-(carboxyethyl)-$CH_2$-para-$C_6H_4$CO] desB30 human insulin | 1.23 |
| $N^{\epsilon B29}$—[N—(HOOC($CH_2$)$_{16}$CO—N-(carboxyethyl)-$CH_2$-para-$C_6H_4$CO] desB30 human insulin | 2.03 |
| $N^{\epsilon B29}$-[(5-{[(2-Carboxyethyl)-(15-carboxypentadecanoyl)-amino]methyl}furan-2-carbonyl)desB30 human insulin | 1.19 |
| $N^{\epsilon B29}$—[N—(HOOC($CH_2$)$_{14}$CO)—N-(carboxyethyl)-$CH_2$-meta $C_6H_4$CO] desB30 human insulin | 1.63 |
| $N^{\epsilon B29}$—[N—(HOOC($CH_2$)$_{14}$CO)—N-(carboxyethyl)-$CH_2$-ortho $C_6H_4$CO] desB30 human insulin | 0.905 |
| $N^{\epsilon B29}$—[N—(HOOC($CH_2$)$_{14}$CO)—N-(carboxyethyl)-para-$C_6H_4$CO] desB30 human insulin | 1.08 |
| $N^{\epsilon B29}$-(3-Carboxy-5-octadecandioylamino-benzoyl) des(B30) human insulin | 2.97 |
| $N^{\epsilon B29}$-(3-Carboxy-4-(14-carboxy-tetradecyloxy)-benzoyl) desB30 human insulin | 1.51 |
| $N^{\epsilon B29}$-(3-Carboxy-5-(14-carboxy-tetradecyloxy)-benzoyl) desB30 human insulin | 1.175 |
| $N^{\epsilon B29}$-{4-Carboxy-4-[10-(4-carboxy-phenoxy)-decanoylamino]-butyryl}desB30 human insulin | 0.388 |
| $N^{\epsilon B29}$-[3-Carboxy-5-(octadecandioyl-N-carboxyethyl-glycin)amino-benzoyl] desB30 human insulin | 0.662 |
| $N^{\epsilon B29}${3-[(3,5-Bis-carboxymethoxy-benzyl)-(15-carboxy-pentadecanoyl)-amino]-propionyl desB30 human insulin | 0.45 |
| $N^{\epsilon B29}$-3-[4'-(2 Carboxy-ethyl)-biphenyl-4-yl]-propionyl-γ-L-glutamyl desB30 insulin | 0.276 |
| $N^{\epsilon B29}$-hexadecandioyl-(4-aminomethyl-benzoyl)-γ-L-glutamyl desB30 human insulin | 1.18 |
| $N^{\epsilon B29}$-4-{[(2-Carboxyethyl)-(15-carboxypentadecanoyl)amino]-methyl}benzoyl)-γ-L-glutamyl desB30 human insulin | 0.399 |
| $N^{\epsilon B29}$-{4-[2-(4-carboxymethyl-phenyl)-ethyl]-phenyl}-acetyl-γ-L-glutamyl desB30 human insulin | 0.291 |
| $N^{\epsilon B29}$-(3-carboxy-4-hexdecandioylamino-benzoyl) desB30-insulin | 1.075 |
| $N^{\epsilon B29}$-10-(4-carboxy-phenylsulfanyl) decanoyl-γ-L-glutamyl desB30 human insulin | 0.475 |
| $N^{\epsilon B29}$-10-(4-Carboxyphenoxy) decanoyl beta-Asp desB30 insulin | 0.348 |
| $N^{\epsilon B29}$-11-(4-Carboxy-phenoxy) undecanoyl-γ-L-glutamyl desB30 human insulin | 0.482 |

The invention claimed is:

1. An insulin derivative having the formula

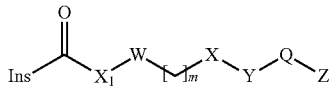

wherein Ins is the parent insulin moiety which via the α-amino group of the N-terminal amino acid residue of the B chain or an ϵ-amino group of a Lys residue present in the B chain of the insulin moiety is bound to the CO— group in the side chain via an amide bond;

$X_1$ is a bond;

W is an arylene;

m is *0 or* 1;

X is a bond;

Y is —($CR_1R_2$)$_q$—NR—CO—, where $R_1$ is H, $R_2$ is H, q is 1; and R —($CH_2$)$_p$—COOH where p is *1 or* 2;

Q is —$(CH_2)_r$— where r is *13,* 14*, 15 or 16*; and

Z is —COOH;

and any $Zn^{2+}$ complex thereof.

2. An insulin derivative according to claim 1, wherein W is phenylene.

3. An insulin derivative according to claim 1, wherein the parent insulin moiety is a des(B30) human insulin or an analogue thereof.

4. An insulin derivative according to claim 1, wherein the parent insulin moiety is selected from the group consisting of human insulin; des(B1) human insulin; desB30 human insulin; GlyA21 human insulin; GlyA21 des(B30)human insulin; AspB28 human insulin; porcine insulin; LysB28ProB29 human insulin; GlyA21ArgB31ArgB32 human insulin; and LysB3GluB29 human insulin.

5. An insulin derivative according to claim 1 selected from the group consisting of [$N^{\epsilon B29}$—[N—(HOOC$(CH_2)_{14}$CO)—N-(carboxymethyl)-$CH_2$—$C_6H_4$CO] des(B30) human insulin; $N^{\epsilon B29}$—[N—(HOOC$(CH_2)_{13}$CO)—N-(carboxymethyl)-$CH_2$—$C_6H_4$CO] des(B30) human insulin; $N^{\epsilon B29}$—[N—(HOOC$(CH_2)_{15}$CO)—N-(carboxymethyl)-$CH_2$—$C_6H_4$CO] des(B30) human insulin; $N^{\epsilon B29}$—[N—(HOOC$(CH_2)_{16}$CO)—N-(carboxymethyl)-$CH_2$—$C_6H_4$CO] des(B30) human insulin;] *$N^{\epsilon B29}$—[N—(HOOC$(CH_2)_{14}$CO)—N-(carboxyethyl)-$CH_2$—$C_6H_4$CO] des(B30) human insulin; $N^{\epsilon B29}$—[N—(HOOC$(CH_2)_{13}$CO)—N-(carboxyethyl)-$CH_2$—$C_6H_4$CO] des(B30) human insulin; $N^{\epsilon B29}$—[N—(HOOC$(CH_2)_{15}$CO)—N-(carboxyethyl)-$CH_2$—$C_6H_4$CO] des(B30) human insulin; $N^{\epsilon B29}$—[N—(HOOC$(CH_2)_{16}$CO)—N-(carboxyethyl)-$CH_2$—$C_6H_4$CO] des(B30) human insulin;* and $N^{\epsilon B29}$—[N—(HOOC$(CH_2)_{14}$CO)—N-(carboxymethyl)-$CH_2$—$C_6H_4$CO] des(B30) human insulin.

6. A pharmaceutical composition for the treatment of diabetes in a patient in need of such treatment, comprising a therapeutically effective amount of an insulin derivative according to claim 1 together with a pharmaceutically acceptable carrier.

7. A pharmaceutical composition for the treatment of diabetes in a patient in need of such treatment, comprising a therapeutically effective amount of an insulin derivative according to claim 1 in mixture with an insulin or an insulin analogue which has a rapid onset of action, together with a pharmaceutically acceptable carrier.

8. A method of treating diabetes in a patient in need of such a treatment, comprising administering to the patient a therapeutically effective amount of an insulin derivative according to claim 1 together with a pharmaceutically acceptable carrier.

9. A method of treating diabetes in a patient in need of such a treatment, comprising administering to the patient a therapeutically effective amount of an insulin derivative according to claim 1 in mixture with an insulin or an insulin analogue which has a rapid onset of action, together with a pharmaceutically acceptable carrier.

* * * * *